US009920296B2

(12) United States Patent
Brown et al.

(10) Patent No.: US 9,920,296 B2
(45) Date of Patent: Mar. 20, 2018

(54) *PAENIBACILLUS ALVEI* STRAIN TS-15 AND ITS USE IN CONTROLLING PATHOGENIC ORGANISMS ON CROPS

(71) Applicant: The United States of America, as represented by the Secretary, Department of Health & Human Services, Washington, DC (US)

(72) Inventors: Eric W. Brown, Taneytown, MD (US); Jie Zheng, Columbia, MD (US); Alexander Enurah, Richmond, VA (US)

(73) Assignee: The United States of America, as represented by the Secretary, Department of Health & Human Servic, Washington, DC (US)

( * ) Notice: Subject to any disclaimer, the term of this patent is extended or adjusted under 35 U.S.C. 154(b) by 0 days.

(21) Appl. No.: 14/085,508

(22) Filed: Nov. 20, 2013

(65) Prior Publication Data
US 2014/0322168 A1    Oct. 30, 2014

Related U.S. Application Data

(63) Continuation-in-part of application No. PCT/US2012/038584, filed on May 18, 2012.

(60) Provisional application No. 61/488,271, filed on May 20, 2011.

(51) Int. Cl.
| | | |
|---|---|---|
| *A01N 63/00* | (2006.01) | |
| *A01G 7/00* | (2006.01) | |
| *A23B 7/155* | (2006.01) | |
| *A23L 33/135* | (2016.01) | |
| *A61K 35/74* | (2015.01) | |
| *C07K 14/195* | (2006.01) | |
| *C12N 1/20* | (2006.01) | |
| *C12N 15/01* | (2006.01) | |
| *C12R 1/01* | (2006.01) | |

(52) U.S. Cl.
CPC .............. *C12N 1/20* (2013.01); *A01G 7/00* (2013.01); *A01N 63/00* (2013.01); *A23B 7/155* (2013.01); *A23L 33/135* (2016.08); *A61K 35/74* (2013.01); *C07K 14/195* (2013.01); *C12N 15/01* (2013.01); *C12R 1/01* (2013.01)

(58) Field of Classification Search
None
See application file for complete search history.

(56) References Cited

U.S. PATENT DOCUMENTS 5,762,928 A  *  6/1998  Bolkan ................. A01N 63/00
                                                   424/93.47

FOREIGN PATENT DOCUMENTS

UA               15147 U           6/2006

OTHER PUBLICATIONS

Anandaraj et al. (Biochemical and Biophysical Research Communications, vol. 379, pp. 179-185; 2009).*
Anandaraj et al. (Biochemical and Biophysical Research Communications, vol. 379, pp. 179-185; 2009) (of record).*
Kim et al., The Plant Pathology Journal, vol. 21, No. 4, pp. 328-333 (2005).*
Hoch et al., Journal of Bacteriology, vol. 90, No. 3, pp. 604-610 (1965).*
Kim et al., The Plant Pathology Journal, vol. 21, No. 4, pp. 328-333 (2005) (of record).*
Anandaraj et al., Biochemical and Biophysical Research Communications, vol. 379, pp. 179-185; available online Dec. 13, 2008 (of record).*
Antonopoulos et al., Biological Control, vol. 46, pp. 166-170 (2008).*
International Search Report and Written Opinion for International Application No. PCT/US2012/038584 dated Sep. 27, 2012.
Anandaraj et al., "Co-production of two new peptide antibiotics by a bacterial isolate Paenibacillus alvei NP75," Biochemical and Biophysical Research Communications, 379:179-185 (2009).
Liao, Ch, 2009, Journal of Food Protection, 72:85-92.
Gardener BBM, 2004, Phytopathology, 94:1252-1258.
International Preliminary Report on Patentability for PCT/US2012/038584, dated Nov. 20, 2014.

* cited by examiner

*Primary Examiner* — Soren Harward
*Assistant Examiner* — Paul D. Pyla
(74) *Attorney, Agent, or Firm* — Klarquist Sparkman, LLP

(57) ABSTRACT

The present invention provides a newly isolated bacterial strain of *Paenibacillus*, designated *Paenibacillus alvei* strain TS-15 for use as a biocontrol agent in the inhibition and/or elimination of a human foodborne pathogen, e.g., *Salmonella*, on a plant or plant organ, e.g., a tomato or tomato plant. Strain TS-15 or mutants thereof may also be used in the control of plant pathogens.

15 Claims, 33 Drawing Sheets

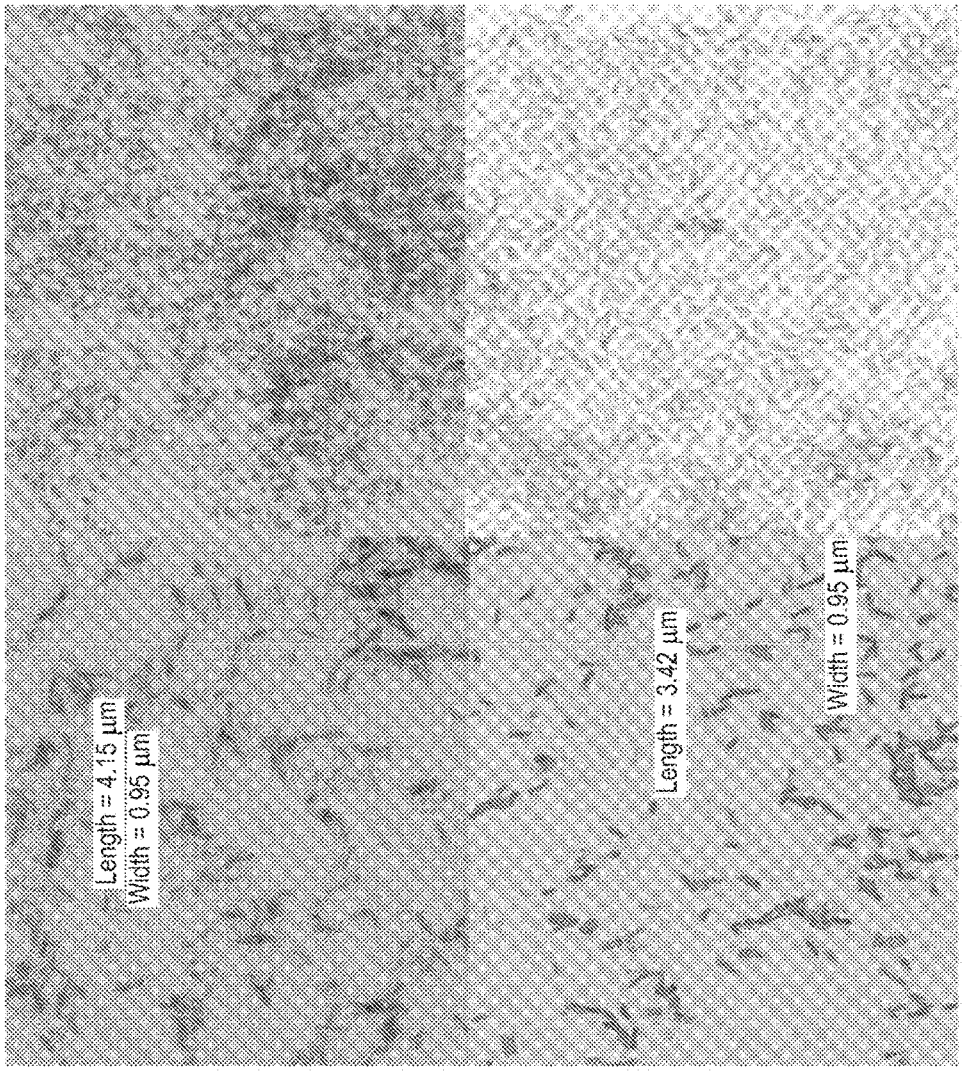

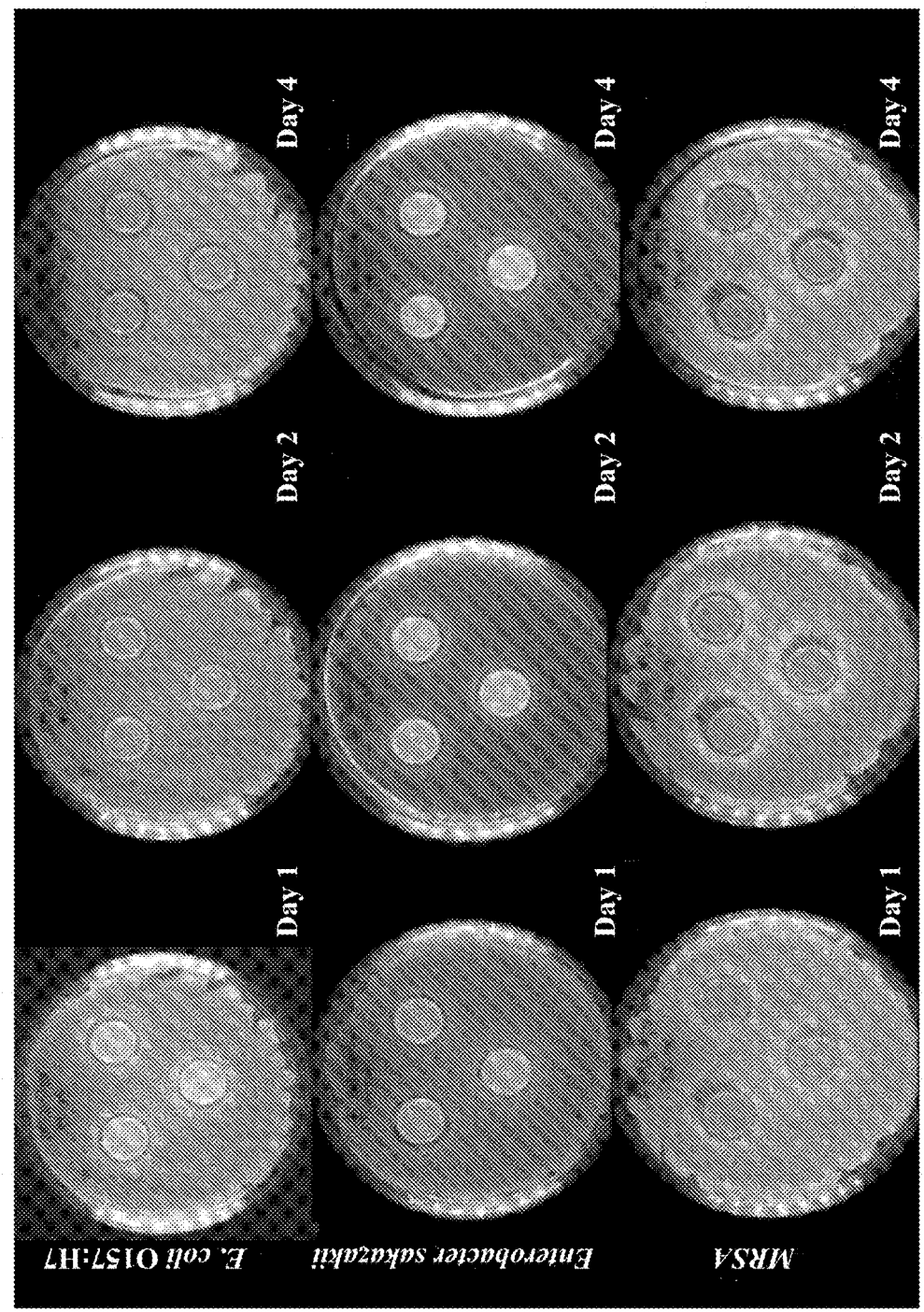

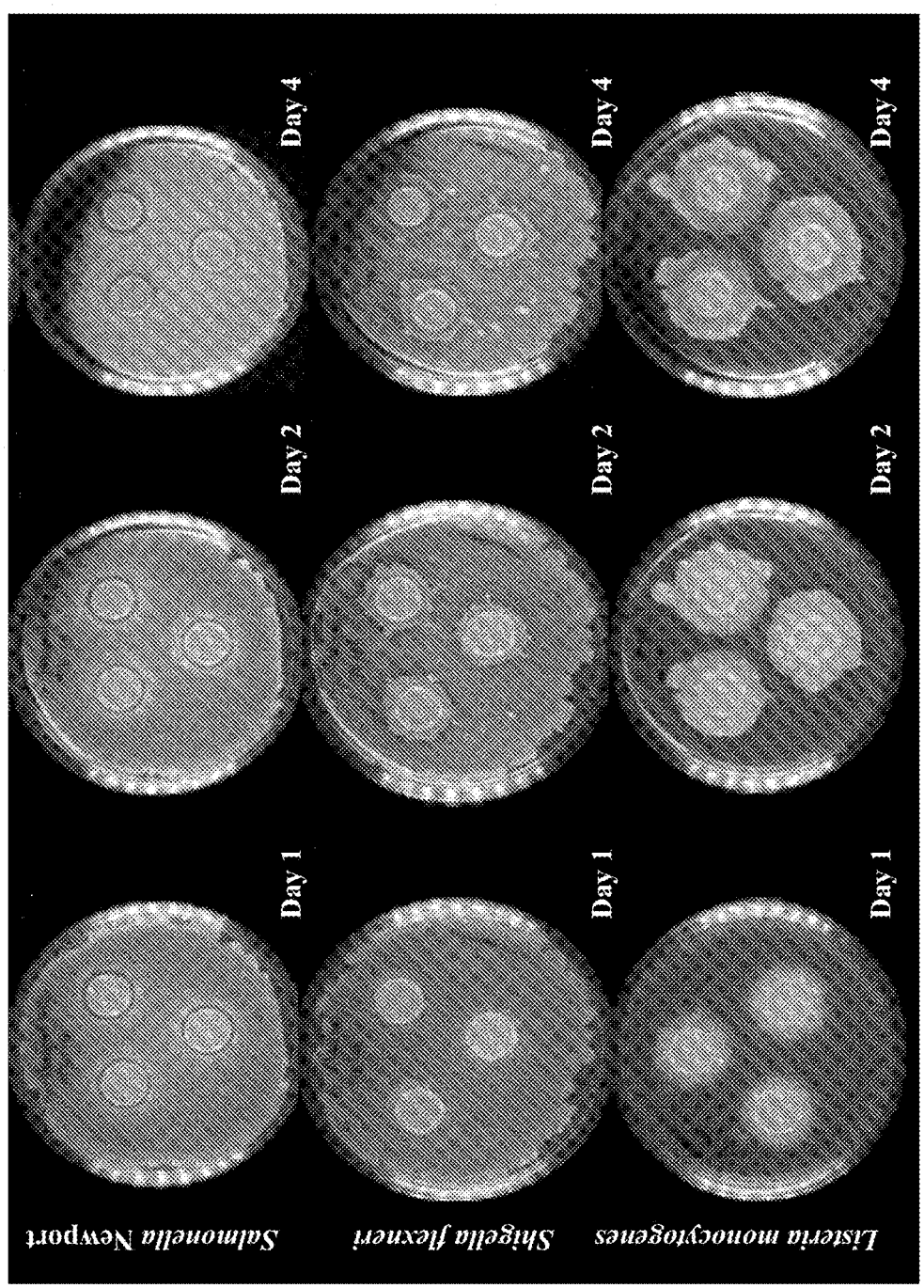

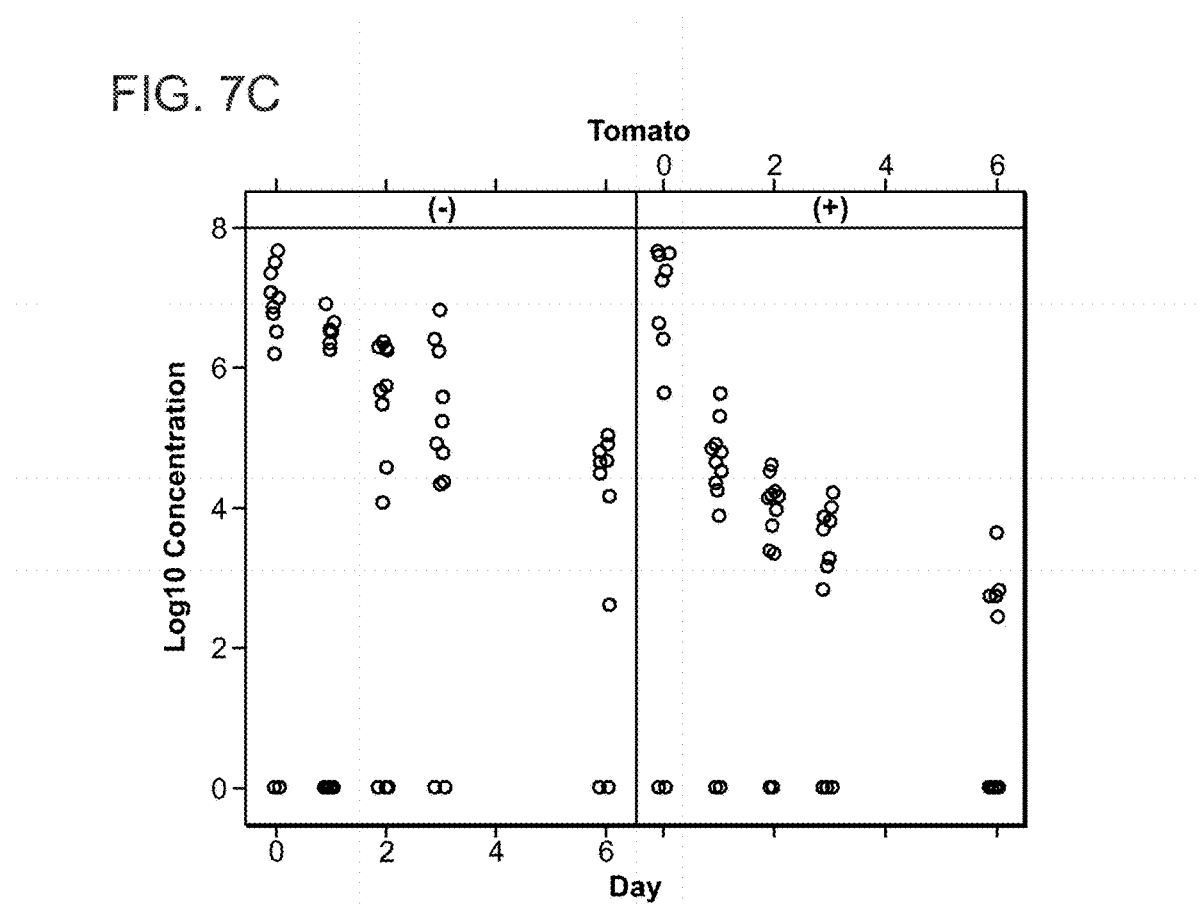

FIG. 15E

PAENIBACILLUS ALVEI STRAIN TS-15 AND ITS USE IN CONTROLLING PATHOGENIC ORGANISMS ON CROPS

RELATED APPLICATIONS

This application is a Continuation in Part of International Application PCT/US2012/038584, filed on May 18, 2012, which claims the benefit of U.S. Provisional Application Ser. No. 61/488,271, filed May 20, 2011, the contents of which are incorporated herein by reference in their entirety.

GOVERNMENT SUPPORT

This work was supported by the Intramural Research Program of the US Food and Drug Administration. The Government has certain rights to this invention.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The present invention relates to a novel and unique strain of bacteria identified as *Paenibacillus alvei* strain TS-15 and its use and/or the use of any mutants thereof in controlling and/or eliminating the contamination of plant-based foods by pathogenic organisms, including especially *Salmonella*, that may cause disease or illness in plants or animals.

2. Background

Prevention of food-related illnesses (or foodborne illnesses) by microbial contamination is a major concern to the food industry, regulatory agencies, and consumers all around the world. Foodborne illnesses rank among the most serious of public health concerns and can be caused by any number of types of pathogens, including, for example, bacteria, viruses, parasites, and prions, as well as toxins produced by such pathogens. The Centers for Disease Control and Prevention (CDC) estimates that, in the U.S. each year, 76 million people become sick, more than 325,000 people are hospitalized, and 5,000 people die from foodborne illnesses. The estimated total cost of such illnesses weighs in the range of $10-83 billion each year, which accounts for medical expenses, reduced productivity and overall pain and suffering, among other costs.

A range of foods are associated with foodborne illnesses, including fresh produce. Produce is recognized as an important component of a healthy diet because it is a staple source of vitamins, minerals, fiber, and antioxidants. Produce can play an important role in weight management as well. Because most produce is grown in a natural environment, it is vulnerable to contamination with pathogens. Factors that may affect the rate of such contamination include agricultural water quality, the use of manure as fertilizer, the presence of animals in fields or packing areas, and the health and hygiene of workers handling the produce during production, packing, or preparation. The fact that produce is often consumed raw without any type of intervention to control or eliminate pathogens prior to consumption contributes to its potential as a source of foodborne illness.

The CDC estimates that, in the 1990's, at least 12 percent of foodborne illnesses were linked to fresh produce items. Over the past decade, the federal government has focused significant resources on reducing foodborne illness from all sources. However, despite these efforts, foodborne illness associated with fresh produce continues to be documented. The persistence of foodborne illness associated with fresh produce may be attributable to a number of factors, but many cases are preventable. Given the importance of produce consumption and its central role in a healthy diet, it is imperative that the number of foodborne illness cases associated with produce be reduced.

Many incidents of produce-related foodborne illness relate to salmonellosis, which can be caused by ingestion of fresh produce, plants, fruits or vegetables, or other produce-related products which are contaminated with or contain various nontyphoidal species of *Salmonella* bacteria. *Salmonella* infections cause fever and gastrointestinal-related symptoms, including diarrhea, vomiting, and abdominal cramps 12 to 72 hours after infection. In most cases, the illness lasts 4 to 7 days and most people recover without treatment. However, in some the diarrhea may be so severe that the patient becomes dangerously dehydrated and requires hospitalization. Treatment may include intravenous fluids to combat the dehydration, and medications, including antibiotics and anti-fever medications, may be given to provide symptomatic relief and/or to eliminate the infection. In severe cases, the *Salmonella* infection may spread from the intestines to the blood, and then to other body sites, and can cause death unless the person is treated promptly with antibiotics. The elderly, infants, and those with impaired immune systems are more likely to develop severe illness. Some people afflicted with salmonellosis later experience reactive arthritis, which can have long-lasting, disabling effects.

Contamination of produce, such as tomatoes, by pathogens like *Salmonella* can occur practically at any point in the produce supply chain, i.e., at any point between the farm and the market. Vulnerable points in the supply chain can include prior to, during or after planting, during open field or greenhouse production, harvesting, field packing or packinghouse, distribution operations, retail food sales, and foodservice sales and preparations. In addition, the soil itself may already be contaminated with the organisms prior to utilizing the land. For example, the soil may be the target of run-off from farm-related animal waste that is contaminated with *Salmonella*.

Produce crops—besides providing a vehicle for certain human or animal pathogens—also may often suffer significantly from a wide variety of plant diseases, the occurrence of which may cause a marked decrease in crop yields, produce quality and appearance, and overall value. Depending on the particular crop, diseases can be caused by any number of different types of plant pathogens, including those that are bacteria, viruses, fungi or other parasites.

As a means for controlling both plant and human/animal pathogens, there have been a wide array of strategies previously implemented or which continue to be used. Some of these strategies generally relate to the control of the cultivation environment, the use of disease-resistant cultivars, the application of agricultural and horticultural fungicides or bactericides, and the biological control of the diseases by the use of organic materials or the like. Of these, the use of agricultural and horticultural fungicides or bactericides or other anti-pathogen agents is direct and often the most effective. However, the application of a large amount of the fungicides or bactericides is clearly undesirable because of the resultant harmful effects on the environment and wildlife that comes into contact with the treated region or with products thereof. In addition, a plurality of fungicidal and/or bactericidal chemicals are often employed to combat the potential for resistance, thereby increasing the level of such chemicals and their negative effects on the environment.

In order to solve the problem of excessive dependence on the use of such harmful agrochemicals, methods for controlling various crop plant diseases and/or human/animal pathogens that contaminate such crop plants have been developed which employ the use of microbial biocontrol agents. Such microorganisms may be natural enemies of the target pathogens sought to be controlled or eradicated, or may be modified genetically to be capable of mitigating or even eliminating unwanted plant and/or human or animal pathogens on crop plants. However, the efficacy of such agents are not yet sufficient. Challenges presented in developing an effective microbial biocontrol agent can include, for example, poor survivability once placed into contact with the crops or the produce itself and low effectiveness of an agent's anti-pathogen activity. Additionally, it is mostly the case that microbial biocontrol agents have been developed for the control of plant-based pathogens, rather than the control of human or animal pathogens associated with plants.

Accordingly, improved microbial biocontrol agents which are more effective against pathogens, have greater sustainability once released into the environment without being harmful to humans, and which are simultaneously effective against both plant and human/animal pathogens would be highly desirable in the art.

SUMMARY OF THE INVENTION

The present invention relates to the identification of a newly isolated strain of *Paenibacillus alvei* and its use as a biocontrol agent in the control and/or elimination of plant pathogens and/or human or animal pathogens that are present on or within plant and plant organs, e.g., whole plants, fruits and/or blossoms, and in particular, those plants that are associated with the production of consumer produce products, such as, tomatoes, peppers, and other fruits, vegetables and greens. The present invention further relates to *Paenibacillus alvei* strain TS-15, which has been first discovered and identified by the present inventors by screening native flora of various produce farmlands located in the mid-Atlantic coast of the U.S. for possible bacteria with antagonistic activity against various foodborne pathogens, including, *Salmonella* Newport and other enteric foodborne pathogens, and which could serve, upon re-introduction, as a biocontrol agent of those pathogens. Thus, the invention relates to the identification and use of *Paenibacillus alvei* strain TS-15—or mutants thereof—as a biocontrol agent in providing food products—especially produce, such as tomato plants and organs thereof—which are free of contamination by *Salmonella*, other enteric bacterial pathogens, and other human foodborne pathogens due to the antagonistic activities of TS-15 against these organisms.

Thus, in another aspect, by extension, the present invention relates to the control of human foodborne illnesses caused by those pathogenic bacteria, such as, *Salmonella*, that persist on produce-based crops and which are susceptible to being inhibited (e.g., bacteriostatic activity) or killed (bacteriocidal activity) by the TS-15 of the invention, or mutants of TS-15 which are within the scope of the invention. Also by extension, the present invention also relates to the control of plant diseases that are caused by plant pathogens which are susceptible to being inhibited (e.g., bacteriostatic activity) or killed (bacteriocidal activity) by the TS-15 of the invention, or mutants of TS-15 which are within the scope of the invention.

In yet another aspect, the present invention relates to compositions comprising strain TS-15 for use as a bio-control agent that can be delivered to a plant or plant organ (e.g., seed, leaf, stem, roof, flower, fruit) or as a pre-treatment of soil prior to growing the target plants, which is capable of inhibiting or killing plant and/or human or animal pathogens on the target plants. In still another aspect, the compositions of the invention that comprise strain TS-15 for use as a bio-control agent may also comprise a specialized growth media that favors growth and proliferation of TS-15, but not the target pathogen, e.g., *Salmonella*. In still a further aspect, the specialized growth media may favor or promote the growth and/or proliferation of TS-15, but be inhibitory against growth and/or proliferation of a target pathogen, e.g., *Salmonella*. In a specific embodiment, the growth media contains D-glucose as a sole carbon source. In another specific embodiment, the growth media contains D-Melezitose as a sole carbon source. In yet another embodiment, the growth media contains a combination of D-glucose and D-Melezitose as the sole sources of carbon. In another embodiment, the sole source of carbon in the growth media is either D-glucose or D-Melezitose—or a combination of both—and the sole source of nitrogen is provided by yeast extract. In still another embodiment, the sole source of carbon in the growth media is either D-glucose or D-Melezitose—or a combination of both—and the sole source of nitrogen is provided by $(NH_4)_2HPO_4$ (ammonium phosphate, dibasic).

In yet a further aspect, given that TS-15 is non-pathogenic to humans and animals, the TS-15 may be provided as a probiotic and administered in a therapeutically effective amount to a subject who is at risk of developing or who presently developed a foodborne illness, such as, salmonellosis. Thus, the present invention also relates to the therapeutic use of TS-15—or effective mutants thereof—as a probiotic-based treatment of foodborne illnesses, including, especially, salmonellosis.

The present inventors sought to identify new and natural means of protecting the food supply from foodborne pathogens, e.g., *Salmonella* species. Native flora of several produce-associated plants, as well as plants associated in proximity to produce farmlands, were screened for possible epiphytic bacteria with antagonistic activity against *Salmonella* Newport, and in other enteric bacteria. Using a multi-phase in vitro screening system, the isolation of several natural plant-associated bacteria were discovered from the environment that block the growth of S. Newport. The screening process revealed two competitive *Salmonella* inhibiting bacteria strains denoted as A6-6i-x and TS-15.

It is has been discovered that TS-15 has antagonistic activity against various plant pathogens as well, and thus, the invention contemplates the use of the strain as a biocontrol agent of plant diseases affecting produce-related crops, such as, tomato-plant diseases.

Accordingly, in one aspect, the present invention relates to a process for the screening and identification of new naturally-occurring microorganisms, in particular, strain TS-15 and mutants thereof, having antagonistic and/or inhibitory activities against foodborne pathogens, including, for example, *Salmonella* Newport and other enteric bacterial pathogens, as well as certain plant pathogens.

In another aspect, the present invention relates to strains of epiphytic bacteria, in particular, strain TS-15 and mutants thereof, with antagonistic and/or inhibitory activities against foodborne pathogens, including, for example, *Salmonella* Newport and other enteric bacterial pathogens, as well as certain plant pathogens.

In still another aspect, the instant invention relates to the characterization of the antagonistic bacteria identified by the processes of the invention as having significant bactericidal and/or bacteriostatic properties against *Salmonella*, e.g., S. Newport. In particular, strain TS-15 is a Gram-positive, facultative anaerobic, endospore-forming bacteria having bactericidal and bacteriostatic properties against *Salmonella* and other enteric bacteria.

In yet a further aspect, the present invention relates to compositions comprising one or more antagonistic microorganisms identified by the methods of the invention, wherein the compositions can be in the form of a spray, pellet, liquid, gel, foam, or the like, and which can be adapted for being administered to a plant or plant organ, e.g., seed, leaf, fruit, root, or whole plant, as a means to control, inhibit or eradicate the growth of human foodborne pathogens and/or plant pathogens located on the plant or plant organ. In certain embodiments, the compositions may contain a growth medium which promotes the growth and/or proliferation of TS-15, but be inhibitory against growth and/or proliferation of a target pathogen, e.g., *Salmonella*. In a specific embodiment, the growth medium contains D-glucose as a sole carbon source. In another specific embodiment, the growth medium contains D-Melezitose as a sole carbon source. In yet another embodiment, the growth medium contains a combination of D-glucose and D-Melezitose as the sole sources of carbon. In another embodiment, the sole source of carbon in the growth medium is either D-glucose or D-Melezitose—or a combination of both—and the sole source of nitrogen is provided by yeast extract. In still another embodiment, the sole source of carbon in the growth medium is either D-glucose or D-Melezitose—or a combination of both—and the sole source of nitrogen is provided by $(NH_4)_2HPO_4$ (ammonium phosphate, dibasic). The growth medium of the invention may also be said to "boost" the growth of TS-15 or mutant thereof, while becoming inhibitory against the growth of a target pathogen, e.g., *Salmonella*.

In still a further aspect, the present invention also relates to the characterization of the antibiotic profile of a biocontrol agent identified by the methods of the invention to be effective in the control, inhibition or eradication of growth of a human foodborne pathogen, such as, *Salmonella*. In a particular aspect, the invention provides for the identification of one or more antibiotics, e.g., a peptide antibiotics, which are effective antagonists of a foodborne pathogen and/or which inhibit colony establishment of produce or even which may eradicate foodborne pathogens from produce or other types of foods. In certain aspects, the discovered biocontrol agents of the invention are not harmful or pathogenic to the subject undergoing treatment, e.g., a human being treated for a foodborne-caused infection. Thus, in another aspect, the biocontrol agents of the invention, e.g., strain TS-15 or mutants thereof, can be administered as a probiotic to a subject who has or is at risk of having a foodborne illness, such as, salmonellosis.

In still another aspect, the present invention provides pharmaceutically-acceptable probiotic compositions, e.g., liquids, sprays, pills, or powders, for use in treating a subject having a foodborne illness, e.g., salmonellosis, wherein said compositions comprise strain TS-15 or a mutant thereof. The composition may also be in the form of a food, such as, for example, yogurt or a yogurt beverage. The probiotic composition may be formulated to contain a growth medium which promotes the growth and/or proliferation of TS-15, but be inhibitory against growth and/or proliferation of a target pathogen, e.g., *Salmonella*. In a specific embodiment, the growth medium contains D-glucose as a sole carbon source. In another specific embodiment, the growth medium contains D-Melezitose as a sole carbon source. In yet another embodiment, the growth medium contains a combination of D-glucose and D-Melezitose as the sole sources of carbon. In another embodiment, the sole source of carbon in the growth medium is either D-glucose or D-Melezitose—or a combination of both—and the sole source of nitrogen is provided by yeast extract. In still another embodiment, the sole source of carbon in the growth medium is either D-glucose or D-Melezitose—or a combination of both—and the sole source of nitrogen is provided by $(NH_4)_2HPO_4$ (ammonium phosphate, dibasic).

In a particular aspect, the invention relates to an isolated *Paenibacillus alvei* strain TS-15 or a mutant thereof that is capable of inhibiting or eliminating the growth of a human foodborne pathogen on a plant or plant organ, or a plant pathogen.

In another particular aspect, the invention relates to a composition for inhibiting or eliminating the growth of a human pathogen on the surface of a plant or plant organ comprising an extracellular extract of *Paenibacillus alvei* strain TS-15 or a mutant thereof.

In still another particular aspect, the invention relates to a method of inhibiting, eliminating, or preventing the growth of a human pathogen on the surface of or within a plant or plant organ comprising contacting the plant or plant organ with a composition comprising *Paenibacillus alvei* strain TS-15 or a mutant thereof, wherein the plant or plant organ is contacted with the strain TS-15 during any of the growing, processing or distribution stages. In embodiments, the *Paenibacillus alvei* strain TS-15 or a mutant thereof is contacted with the plant within 72 hours after transplant of the plant. In related embodiments, the plant is an immature seedling. In embodiments, the composition is contacted with the immature seedling when the seedling is initially planted. In related embodiments, the immature seedling is initially cultivated in a greenhouse.

In yet another aspect, the invention provides a method of making a mutant of *Paenibacillus alvei* strain TS-15 comprising, mutagenizing *Paenibacillus alvei* strain TS-15 and then isolating one or more candidate mutants which retain the same or substantially the same level of antagonistic activity as the parent strain.

In still another aspect, the invention relates to a kit that can be used to treat plants and plant organs so that plant and/or human or animal pathogens present on or in the plant are inhibited or even eradicated.

In still other aspect, the invention relates to a kit for treating a plant or plant organ in vitro or in situ, said plant or plant organ being contaminated with a human foodborne pathogen or plant pathogen, wherein the kit comprises *Paenibacillus alvei* strain TS-15 or a mutant thereof.

In still further aspects, the invention relates to a kit for treating a plant or plant organ in vitro or in situ, said plant or plant organ being contaminated with a human foodborne pathogen or plant pathogen, wherein the kit comprises an extracellular extract of *Paenibacillus alvei* strain TS-15—or mutant thereof—or an antibiotic obtained from *Paenibacillus alvei* strain TS-15 that is bacteriostatic or bactericidal against the pathogen or other active agent produced by TS-15 or mutant thereof which inhibits the growth of or kills a plant or human/animal pathogen, in particular *Salmonella*.

In certain embodiments, the kits or any of the compositions of the invention may comprise a growth medium which promotes the growth and/or proliferation of TS-15, but be inhibitory against growth and/or proliferation of a target pathogen, e.g., *Salmonella*. In a specific embodiment, the growth medium contains D-glucose as a sole carbon source. In another specific embodiment, the growth medium contains D-Melezitose as a sole carbon source. In yet another embodiment, the growth medium contains a combination of D-glucose and D-Melezitose as the sole sources of carbon. In another embodiment, the sole source of carbon in the growth medium is either D-glucose or D-Melezitose—or a combination of both—and the sole source of nitrogen is provided by yeast extract. In still another embodiment, the sole source of carbon in the growth medium is either D-glucose or D-Melezitose—or a combination of both—and the sole source of nitrogen is provided by $(NH_4)_2HPO_4$ (ammonium phosphate, dibasic).

In various embodiments of the above aspects, the foodborne pathogen can be *Salmonella enterica* serovar Newport. In still other embodiments, the foodborne pathogen can be *E. coli* O157:H7. In yet further embodiments, the foodborne pathogen can be a species of *Salmonella*, *Escherichia*, *Listeria*, *Shigella*, *Enterobacter* and *Staphylococcus*.

In other embodiments, the plant or plant organ can be a fruit or vegetable produced by the plant, e.g., a tomato. In certain embodiments, the plant or plant organ is that of a tomato and/or pepper plant, including plants from the Solanaceae family and the *Capsicum* family. The plants or plant organs may also be others that are common sources of foodborne pathogens, such as, but not limited to leafy greens, celery, and other culinary vegetables, podded vegetables, bulb and stem vegetables, root and tuberous vegetables, as well as certain fruits, such as, cantaloupe. The plant pathogens may include, for example, *Clavibacter michiganensis* pv. *michiganensis*, *Pseudomonas syringae* pv. *tomato*, *Xanthomonas capesiris* pv. *vesicatoria*, *Ralstonia solanacearum*, and *Erwinia carotovora* subsp. *carotovora*, among other pathogens of plants in the Solanaceae the *Capsicum* families.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 provides light microscopic images of stained *P. alvei* strain A6-6i-x and TS-15. (A) The cells were stained with Gram stain. (B) The cells were stained with endospore stain.

FIG. 2 is a photograph of the results of an in vitro agar plug assay to assess the effects of *P. alvei* strain TS-15 on growth inhibition of foodborne pathogens: (A) *E. coli* O157:H7; (B) *Enterobacter* sakazakii; (C) methicillin-resistant *Staphylococcus aureus* (MRSA); (D) *Salmonella enterica* serovar Newport; (E) *Shigella flexneri*; and (F) *Listeria monocytogenes* at day 1, day 2 and day 4 of growth on the in vitro agar plate. The experiment was repeated in duplicate with similar results.

Figure 15E:
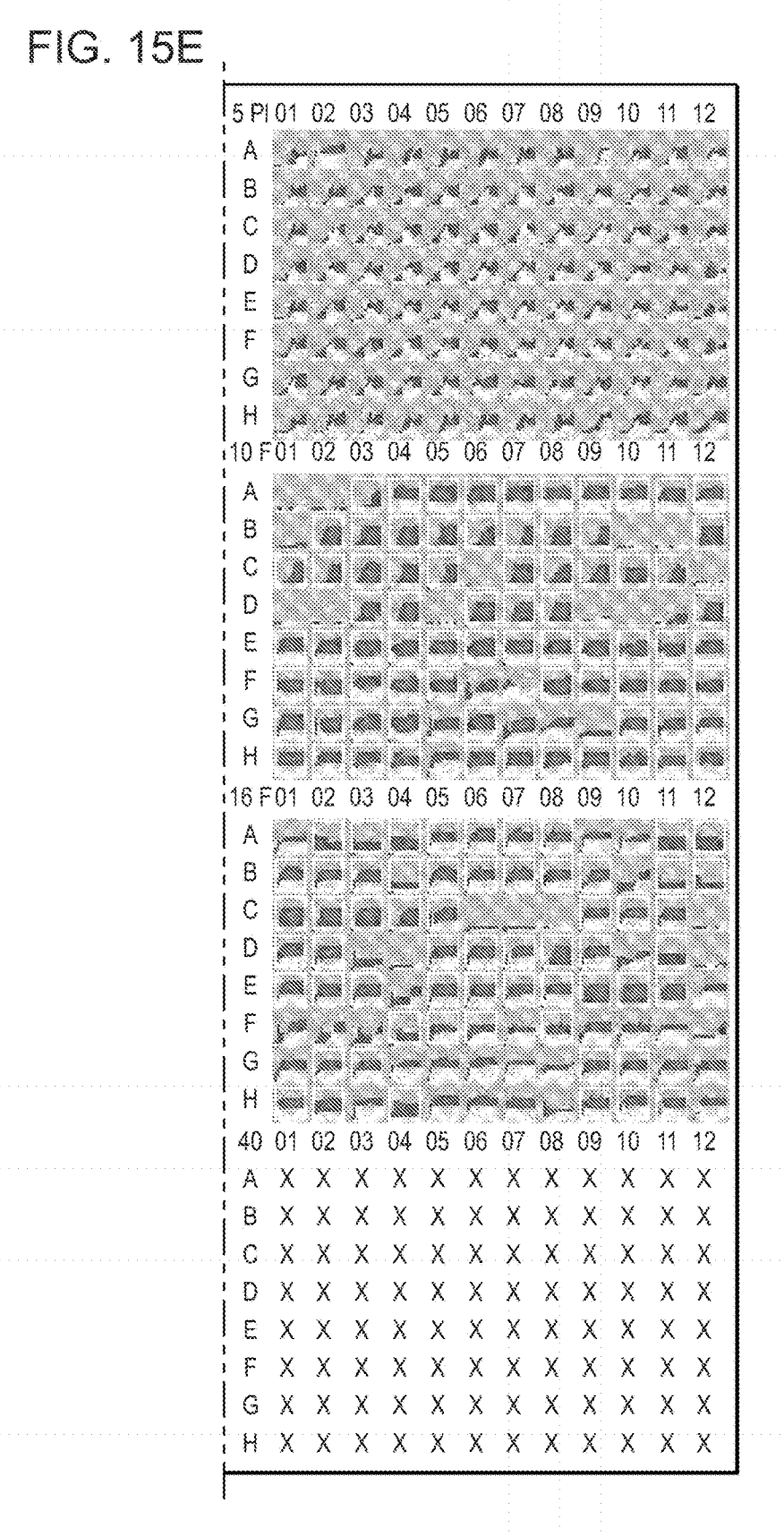

FIG. 15A, FIG. 15B, FIG. 15C, FIG. 15D and FIG. 15E show the results of cellular phenotypic analyses of both strain TS-15 and S. Newport using Biolog Phenotypic Microarray (PM) System (Biolog, Inc.) which shows the simultaneous screening of about 1,200 phenotypes.

DETAILED DESCRIPTION OF THE INVENTION

Figure 3A:
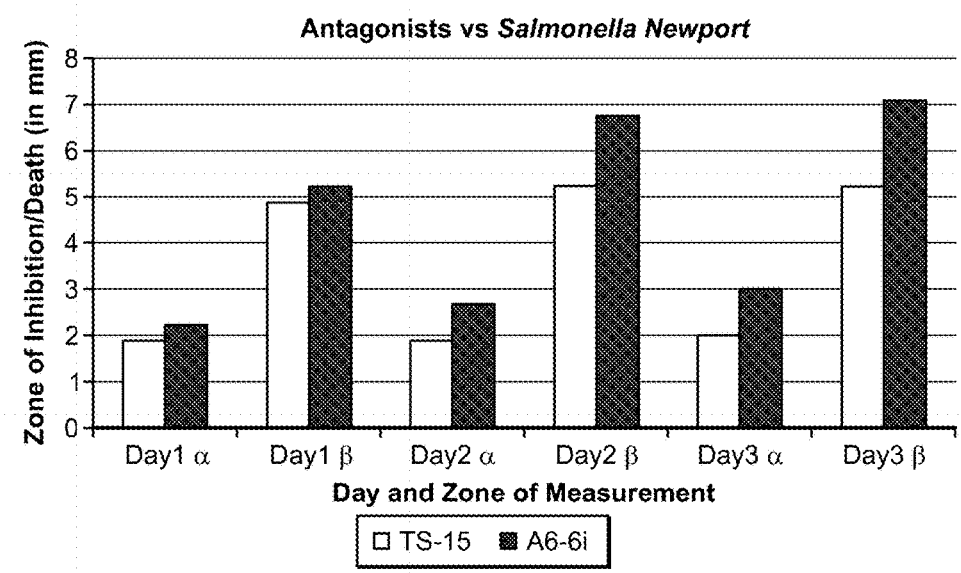
FIG. 3 compares antagonistic effectiveness between TS-15 and A6-6i-x against S. Newport. (A) Shows a bar graph of the zones of inhibition measured from the S. Newport plug assay. The α is the initial inhibition zone while the 0 is the grow over death zone. (B) A S. Newport growth curve showing the difference between the two antagonists and a standard broth growth curve.

The present invention relates to the identification of a newly isolated strain of *Paenibacillus alvei* and its use as a biocontrol agent in the control and/or elimination of contamination of plant and plant organs, e.g., whole plants, fruits and/or blossoms, by *Salmonella* and other human foodborne pathogens. The biocontrol agents of the invention, e.g., strain TS-15, may also be effective against the control and/or eradication of certain plant disease-causing pathogens and may therefore be used to treat not only human or animal foodborne illnesses, but also in the control of certain plant diseases. In a particular aspect, the invention relates to the identification and use of *Paenibacillus alvei* strain TS-15 as a biocontrol agent in providing food products—especially produce, such as tomato plants and organs thereof—which are free of contamination of *Salmonella* and other human foodborne pathogens. The invention also pertains to mutants of TS-15, such as a UV-resistant mutant, that may be derived from or generated from TS-15 by known methods to improve at least characteristic of TS-15. Such mutants may impart various advantages on TS-15, such as enhanced survivability in the field due to UV-resistance. In another aspect, the invention relates to the formulation of TS-15 in a mixture with one or more carbon-source boosters (e.g., D-glucose or D-Melezitose) that further accelerate growth and bactericidal activity of TS-15 against *Salmonella* without aiding the growth of *Salmonella*. The invention further relates to the identification and use of new antibiotic agents, e.g., bactericidal peptides, produced by *Paenibacillus alvei* strain TS-15, their isolation and characterization, and the use of such agents in the treatment of illness and/or disease caused by human pathogens.

A deposit of the *Paenibacillus alvei* strain TS-15 was made with the American Type Culture Collection (ATCC), 10801 University Blvd., Manassas, Va., 20110. The date of deposit is Nov. 25, 2014. The deposit is intended to meet all of the requirements of 37 C.F.R. §§1.801-1.809. The accession number for the deposited *Paenibacillus alvei* strain TS-15 is ATCC Accession No. PTA-121756. The deposit will be maintained in the depository for a period of 30 years, or 5 years after the last request, or for the effective life of the patent, whichever is longer, and will be replaced if necessary during that period.

Thus, the present invention relates to strain TS-15 and mutants thereof (e.g., UV-resistant mutants), compositions comprising TS-15 or its mutants for application to plants or plant organs for controlling and/or eliminating harmful human and/or plant pathogens from the plants, therapeutic compositions (e.g., probiotic compositions) comprising the TS-15 or its mutants for administering to a subject who has or is at risk of having a foodborne illness, e.g., salmonellosis, to treat the illness, and the active agents produced by TS-15 having bactericidal or bacteristatic activities against those pathogens causing plant or human illness, e.g., *Salmonella*.

The present inventors sought to identify new and natural means of protecting the food supply from foodborne pathogens, e.g., *Salmonella* species. Native flora of several produce-associated plants, as well as plants associated in proximity to produce farmlands, were screened for possible epiphytic bacteria with antagonistic activity against *Salmonella*. Using a multi-phase in vitro screening system, the isolation of several natural plant-associated bacteria were discovered from the environment that block the growth of S. Newport. The screening process revealed two competitive *Salmonella* inhibiting bacteria denoted as A6-6i-x and TS-15.

Various aspects of the present invention are described in further detail in the following subsections.

Definitions and Use of Terms

The present invention may be understood more readily by reference to the following detailed description of preferred embodiments of the invention and the Examples included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

As used herein, TS-15 that is "capable of inhibiting or eliminating the growth of a human foodborne pathogen on a plant or plant organ" is meant that the TS-15 strain, once placed into contact with the plant or plant organ, results in a bacteriostatic or bactericidal effect. That is, where TS-15 is bacteriostatic against a human foodborne pathogen, the pathogen's growth is inhibited, but the pathogen is not killed. Preferably, the growth should be inhibited by more than 50% of its normal growth rate under like conditions, or preferably by more than 60%, or 70%, or 80%, or 90%, or 99% of its normal growth rate under like conditions. Where TS-15 is bactericidal against a human foodborne pathogen, the pathogen is killed or substantially killed. Preferably, the TS-15 should eliminate or kill more than 50% of the population of pathogens it is in contact with, or should eliminate more than 60%, or 70%, or 80%, or 90%, or 99% or 100% of the pathogens.

As used herein, reference to "TS-15" or "strain TS-15" is equivalent to *Paenibacillus alvei* strain TS-15.

As used herein, the term "plant-based foods" designates any type of produce that may be fit for consumption, including, for example, fruits, vegetables (e.g., tomatoes), seeds, leaves, stems, roots, and blossoms, or any other plant organ.

As used herein, the term "biocontrol agent" refers to a living organism that can be administered to a plant or plant organ (e.g., seed, root, stem, leaf, fruit, blossom, etc.) to control, reduce, mitigate, eradicate or eliminate the presence of a pathogen. The pathogen may be a plant-based pathogen, or a pathogen that is capable of causing a disease in humans or animals, e.g., *Salmonella*.

As used herein, the term "plant or plant organ" refers to any part or component of a plant, including the stem, roots, leaves, fruit, or blossoms or reproductive organs.

As used herein, the term "foodborne pathogen" refers to a microorganism which is pathogenic to humans and which inhabits any type of food which is consumed by a human.

"Pathogenic" refers the capacity for an organism to cause disease or illness in another organism.

As used herein, the term "antagonizing the growth" is equivalent to inhibition of the growth of an organism or bactericidal prevention of the growth of an organism.

As used herein, the term "cell-free culture supernatant" or "CFCS" refers to spent culture media following removal of TS-15 cells, but which would contain any extracellular bactericidal or bacteriostatic cell-produced components, e.g., peptide antibiotics, which would inhibit or kill the foodborne pathogens or plant pathogens of the invention.

As used herein, the term "enteric pathogen" relates to the family Enterobacteriaceae which cause foodborne illnesses in humans and animals.

As used herein, the term "epiphytic" refers to the condition of bacteria which are naturally found on plant surfaces.

As used herein, the term "naturally-occurring" refers to the condition of occurring in some form in the natural world. For example, a bacterium is naturally-occurring if it exists in a form living on the surface of a plant or in the soil.

As used herein, the term "isolated," as in an isolated strain, refers to the condition of a bacterial strain which has been removed from its natural environment, e.g., the soil or a plant surface, and has been substantially purified by removing the components of the environment from which it came, e.g., soil, minerals, organic material, and isolated and/or separated from other microorganisms.

As used herein, the term "probiotic" refers to live microorganisms thought to be beneficial to host organisms, and when administered in adequate amounts, confer a health benefit on the host. Lactic acid bacteria (LAB) and bifidobacteria are common types of microbes used as probiotics; but certain yeasts and *bacilli* may also be helpful. Probiotics are commonly consumed as part of fermented foods with specially added active live cultures; such as in yogurt, soy yogurt, or as dietary supplements. As contemplated herein, the TS-15 of the invention and its mutants may be utilized as probiotics for treating or preventing foodborne illnesses, e.g., salmonellosis. The "probiotic compositions" of the invention refers to any suitable ingestable and safe formulation (which can include a food, e.g., yogurt, ice cream) that comprises a therapeutically effective amount of the bacteria of the invention.

An "isolated" or "purified" bacterial strain is substantially free of materials from its natural environment including soil and biological matter including other bacterium or plant matter. The language "substantially free of materials from its natural environment" includes preparations or cultures of the bacterium in which the bacterium is separated from components of the environment in which it is naturally found. In one embodiment, the language "substantially free of materials from its natural environment" includes cultures having less than about 20% (by count) of non-TS-15 bacteria (also referred to herein as contaminating bacteria, contaminating bacteria does not include bioactive mutants or modified forms of TS-15), more preferably less than 10% (by count) of non-TS-15 bacteria and most preferably less than about 5% non-TS-15 bacteria.

*Paenibacillus* Strain TS-15

The present invention, in one aspect, relates to isolated *Paenibacillus* strains that act as inhibitor agents against *Salmonella* and other foodborne pathogens. In one embodiment, the preferred strain is *Paenibacillus alvei* strain TS-15, which is antagonistic against *Salmonella* and other such pathogens, including, but not limited to pathogenic species of *Salmonella, Escherichia, Listeria, Shigella, Enterobacter* and *Staphylococcus*.

*Paenibacillus* is a genus of Gram-positive, facultative anaerobic, endospore-forming bacteria, originally included within the genus *Bacillus* and then reclassified as a separate genus in 1993. Bacteria belonging to this genus have been detected in a variety of environments such as: soil, water, *rhizosphere*, vegetable matter, forage and insect larvae, as well as clinical samples. The name reflects this fact: Latin paene means almost, and so the *Paenibacilli* are literally almost *Bacilli*. The genus includes *P. larvae*, which is known to cause American foulbrood in honeybees, the *P. polymyxa*, which is capable of fixing nitrogen and therefore is used in agriculture and horticulture, the *Paenibacillus* sp. JDR-2 which is known to be a rich source of chemical agents for biotechnology applications and pattern forming strains such as *P. vortex* and *P. dendritiformis* discovered in the early 90s, which are known to develop complex colonies with intricate architectures.

Strain TS-15 was isolated by screening the native microflora of various plant organs including (leaves, shoots, roots, and blossoms) and soil at various Eastern Shore tomato growing regions. Three grams of plant material or soil were mixed for about 5 minutes in 1 ml of phosphate-buffered saline (PBS). 100 µl was plated onto Nutrient Yeast Glucose agar (NYGA). Ten colonies with unique morphologies which developed within 48 hours at 30° C. under aerobic conditions were picked for further purification. These colonies were also tested using the 3% KOH test. The KOH test is a rapid test for Gram differentiation without staining.

The colonies of pure cultures were then tested for antagonistic activity in vitro using an agar plug method as discussed in Visser R. et al., Appl. Environ. Microbiol. 1986 552-555, which is incorporated herein in its entirety. The morphological characteristics of the potential antagonists were observed by Gram staining and spore staining. The isolates were further tested with Vitek® 2 compact Biochemical identification system (BIOMERIEUX, INC., Durham, N.C.). VITEK® 2 compact colorimetric cards were read and interpreted automatically with the VITEK® 2 compact system, version 01.01b.

In addition, genomic DNA of the isolates was extracted using WIZARD® genomic DNA purification kit (PROMEGA). A pair of universal primers specific for bacterial 16S rRNA, Eubac27 and R1492 (sequences available in DeLong et al., E. F. Proc. Natl. Acad. Sci. USA, 1992 (89): 5685-5689, which is incorporated herein by reference in its entirety), were used to amplify the corresponding 16S rRNA gene. PCR amplification of the 16S rRNA was performed with a Hotstart Taq plus DNA polymerase kit (QIAGEN, Valencia, Calif.) under the following conditions: after an initial 5-min incubation at 95° C., the mixture was subjected to 30 cycles, each including 1 min at 95° C., 1 min at 58° C., and 1 min at 72° C. A final extension was performed at 72° C. for 10 min. Primers 4F, 27F, 357F, 578F, 1000R, and 1492R were used for sequencing BLAST algorithm was used for homology search against Genbank. Only results from the highest-score queries were considered for phylotype identification, with 99% minimum similarity. Based on these analyses, the isolated organism was identified as a heretofore unknown strain of *Paenibacillus alvei*, strain TS-15.

The TS-15 of the invention may be utilized in any form, including its vegetative growth form or its sporulated state or as spores. The TS-15 of the invention can be provided in liquid growth culture, growth plates/colonies, dried, spores or in any other form so long as they are capable of inhibiting *Salmonella* and preferably other foodborne disease-causing pathogens, such as pathogenic species of *Shigella, Escheri-*

*chia, Enterobacter, Listeria* or *Staphylococcus.* As used herein, the capability of inhibiting *Salmonella* or other pathogen can be determined by known methods. Standard assays, such as those described herein, can be used to determine the ability of the strain to act against the bacterial pathogens of interest. The standard assays can be conducted in vitro or in the field.

As discussed herein further, the TS-15 strain of the invention may be provided in specially designed compositions that have defined carbon and nitrogen sources which are such that growth of TS-15 is enhance or caused to be boosted; however growth of target pathogens is inhibited or at least is not promoted by the particular carbon and nitrogen sources utilized.

Mutants of Strain TS-15

The invention also pertains to bioactive mutants or modified forms of strain TS-15 which retain their inhibitory effect against *Salmonella* or other pathogenic foodborne bacteria, while possessing a change in at least one other characteristic relative to wildtype TS-15 (e.g., enhanced UV-resistance). As used herein, the term "bioactive mutants or modified forms of strain TS-15" is intended to include bacteria which have naturally become mutated or have become mutated by manipulations such as, for example, chemical or UV mutation or genetic modification or transformation been modified to have other characteristics such as, for example, antibiotic resistance.

As used herein, inhibition is a reduction in the growth or development of the target pathogen, for example, against control systems. Standard assays, such as those described herein, can be used to determine the ability of the strain or bioactive mutants or modified forms thereof to act against the bacterial pathogens of interest. The standard assays can be conducted in vitro or in the field.

The TS-15 mutants can be in vegetative or spore state. They can be in culture, dried, viable or in any other form so long as they are capable of inhibiting *Salmonella* and preferably other foodborne disease-causing pathogens, such as pathogenic species of *Shigella, Escherichia, Enterobacter, Listeria* or *Staphylococcus.* The mutants of *Paenibacillus alvei* strain TS-15 contemplated by the invention may be prepared or isolated using well-known methods. Random mutants of TS-15 can be collected under different selection-induced conditions, such as, for example, conditions that select for antibiotic resistance or resistance to some other environmental stress, such as resistance to ultraviolet light or resistance to dessication. Random mutants naturally exist in a population of cells given the error rate in DNA replication and other environmental conditions that may induce a genetic change (e.g., UV light). Mutants may also be obtained by contacting the TS-15 strain with a mutagenizing agent, such as a chemical (e.g., DNA-intercalating agent) or radiation source (e.g., UV light), which will increase the appearance of nucleotide changes in the genome, and thus the appearance of mutant cells in the population, which may be propagated under selection conditions (e.g., antibiotic resistance, heat resistance, acid resistance). Methods of mutagenesis are well-known in the art and can be found described in more detail in, for example, U.S. Pat. Nos. 7,354,715, 7,892,822, 7,871,817, 7,767,454, 7,749,743, 7,732,570, 7,647,184, 7,615,362, 7,504,207, and 7,455,840, each of which are incorporated herein by reference.

Other mutants that may be obtained can include those mutants which show enhanced utilization of particular carbon and nitrogen sources, or other growth nutrients, which are not utilized, or which may even inhibit the growth of a target pathogen, e.g., *Salmonella.*

Pathogens and Diseases

The TS-15 and mutants thereof were demonstrated as having an antagonistic activity against *Salmonella* Newport and other enteric bacterial pathogens on tomato plants and other plants of the family Solanaceae (the Nightshade family), which includes tomatoes and peppers. See Examples. However, the TS-15 and its mutants may also be effective against a variety of plant and human pathogens.

In particular, TS-15 and its mutants may be effective against many plant diseases caused by Gram-negative bacteria, such as those disease caused by *Pseudomonas.* Specific examples of plant diseases caused by such organisms and related organisms included: bacterial blight of plants of the Cucurbitaceae, such as bacterial blight (*Pseudomonas syringae* pv. *lachrymans*) of melon and cucumber, and sheath brown rot (*Pseudomonas fuscovaginae*) of rice. As the plant diseases caused by strains belonging to the genus *Fusarium*, there are exemplified scab (*Fusarium graminearum, Fusarium avenaceum, Fusarium culmorum*) of barley, wheat, oats and rye, *Fusarium* wilt (*Fusarium oxysporum* f. sp. *cucumerium*) of cucumber, *Fusarium* wilt (*Fusarium oxysporum* f. sp. *melonis*) of melon, and *Fusarium* wilt (*Fusarium oxysporum* f. sp. *lycopersici*) of tomato.

The biocontrol strains of the invention may also be able to control plant diseases caused by common plant pathogenic fungi, for example, various pathogenic fungi such as strains belonging to the genus *Colletotrichum* and strains belonging to the genus *Glomerella.* The plant diseases caused by the strains belonging to the genus *Colletotrichum* include, for example, anthracnose of plants of the Cucurbitaceae, such as anthracnose (*Colletotrichum orbiculare*) of cucumber, and anthracnose (*Colletotrichum acutatum*) of strawberry. The plant diseases caused by the strains belonging to the genus *Glomerella* include, for example, ripe rot (*Glomerella cingulata*) of grape and anthracnose (*Glomerella cingulata*) of strawberry.

The biocontrol strains of the invention may also be effective plant diseases other than the above-exemplified plant diseases, such as gray mold (*Botrytis cinerea*) and stem rot (*Sclerotinia sclerotiorum*) of various crop plants; blast (*Pyricularia oryzae*), sheath blight (*Thanatephorus cucumeris*) and *Helminthosporium* leaf spot (*Cochliobolus miyabeanus*) of rice; scab (*Venturia inaequalis*), *Alternaria* leaf spot (*Alternaria mali*) and canker (*Valsa ceratosperma*) of apple; black spot (*Alternaria kikuchiana*) and scab (*Venturia nashicola*) of pear; melanose (*Diaporthe citri*), bluemold (*Penicillium italicum*) and canker (*Xanthomonas campestris* pv. *citri*) of citrus; *Phomopsis* rot (*Phomopsis* sp.) and brown rot (*Monilinia fructicola*) of peach; anthracnose (*Gloeosporium kaki*) and angular leaf spot (*Cercospora* kaki) of Japanese persimmon; powdery mildew (*Erysiphe graminis*), rust (*Puccinia graminis, P. striformis, P. recondita*), loose smut (*Ustilago nuda*) and scab (*Gibberella zeae, Mono graphella nivalis*) of barley, wheat, oats and rye; powdery mildew (*Sphaerotheca cucurbitae*), gummy stem blight (*Didymella bryoniae*) and downy mildew (*Pseudoperonospora cubensis*) of cucumber; leaf mold (*Fulvia fulva*) of tomato; *Verticillium* wilt (*Verticillium dahliae*), brown rot (*Phytophthora capsici*) and bacterial wilt (*Ralstonia solanacearum*) of eggplant; brown spot (*Alternaria alternata*) of tobacco; leaf spot (*Cercospora beticola*) of beet; late blight (*Phytophthora infestans*) of potato; purple stain (*Cercospora kikuchii*) of soybean; downy mildew (*Pernospora brassicae*) of Japanese radish; downy mildew (*Peronospora spinaciae*) of spinach; bacterial blight (*Xanthomonas campestris* pv. *vitians*) and bacterial soft rot (*Erwinia carotovora* subsp. *carotovora*) of lettuce; black rot (*Xanthomonas campestris* pv. *campestris*) of cabbage; club root (*Plasmodiophora brassicae*) of vegetables of Cruciferae; seedling blight (*Pyythium* sp) of various crop plants; violet root rot (*Helicobasidium mompa*) of fruit trees; large patch (*Rhizoctonia solani*) and *Curvularia* leaf blight (*Curvularia* sp.) of lawn grass; etc.

The biocontrol strains of the invention may further be effective against a variety of fungal-based plant diseases, which include: gray mold (*Botrytis cinerea*) and stem rot (*Sclerotinia sclerotiorum*) of various crop plants; blast (*Pyricularia oryzae*), sheath blight (*Thanatephorus cucumeris*) and *Helminthosporium* leaf spot (*Cochliobolus miyabeanus*) of rice; scab (*Venturia inaequalis*), *Alternaria* leaf spot (*Alternaria mali*) and canker (*Valsa ceratosperma*) of apple; black spot (*Alternaria kikuchiana*) and scab (*Venturia nashicola*) of pear; melanose (*Diaporthe citri*) and blue mold (*Penicillium italicum*) of citrus; Phomopsis rot (*Phomopsis* sp.) and brown rot (*Monilinia fructicola*) of peach; anthracnose (*Gloeosporium kaki*) and angular leaf spot (*Cercosporakaki*) of Japanese persimmon; ripe rot (*Glomerella cingulata*) of grape; powdery mildew (*Erysiphe graminis*), rust (*Puccinia graminis, P. striformis, P. recondita*), loose smut (*Ustilago nuda*) and scab (*Monographella nivalis*) of barley, wheat, oats and rye; powdery mildew (*Sphaerotheca cucurbitae*), gummy stem blight (*Didymella bryoniae*) anthracnose (*Colletotrichum orbiculare*) and downy mildew (*Pseudoperonospora cubensis*) of cucumber; leaf mold (*Fulvia fulva*) of tomato; Verticillium wilt (*Verticillium dahliae*) and brown rot (*Phytophthora capsici*) of eggplant; anthracnose (*Collectorichum acutatum, Glomerella cingulata*) of strawberry; brown spot (*Alternaria alternata*) of tobacco; leaf spot (*Cercospora beticola*) of beet; late blight (*Phytophthora infestans*) of potato; purple stain (*Cercospora kikuchii*) of soybean; downy mildew (*Pernospora brassicae*) of Japanese radish; downy mildew (*Peronospora spinaciae*) of spinach; club root (*Plasmodiophora brassicae*) of vegetables of Cruciferae; seedling blight (*Pythium* sp) of various crop plants; violet root rot (*Helicobasidium mompa*) of fruit trees; large patch (*Rhizoctonia solani*) and *Curvularia* leaf blight (*Curvularia* sp.) of lawn grass; etc.

The biocontrol strains of the invention may further be effective against a variety of virus-based plant diseases, including cucumber mosaics (cucumber mosaic cucumovirus, watermelon mosaic2 potyvirus, zucchini yellow mosaic poryvirus), tomato viral diseases (tobacco necrosis necrovirus), strawberry viral diseases (strawberry crincle cytorhabdovirus, strawberry latent C virus, soybean dwarf luteovirus, strawberry mottle virus, strawberry pseudo mild-yellow edge carlavirus, strawberry vein banding caulimovirus, tobacco mosaics tobamovirus, tobacco necrosis necrovirus), cabbage mosaic (cauliflower mosaic caulimovirus, cucumber mosaic cucumovirus, turnip mosaic poryvirus), soybean viral diseases (southern bean mosaic sobemovirus, peanut stunt cucumovirus, bean common mosaic poryvirus, broad bean wilt fabavirus) and potate leaf-roll (potate leafroll luteovirus).

When the inventive strains of the invention are used for controlling plant diseases, spores, vegetative cells, whole culture or the like of the strain of the genus *Paenibacillus* may be usually used. They may be prepared from a culture obtained by cultivating the strain of the genus *Paenibacillus* by a conventional method. The whole culture obtained may be prepared into whole culture powder, for example, by freeze-drying the whole culture as it is. The vegetative cells may be prepared as a cell precipitate, for example, by centrifuging whole culture after the cultivation to remove contaminants, further centrifuging the resulting supernatant, and then washing the cells precipitated. In addition, the spores may be prepared as freeze-dried spore powder, for example, by suspending the cell precipitate obtained above in distilled water and freeze-drying the resulting suspension.

Although the strain of the genus *Paenibacillus* used in the present invention is usually viable cells, it may be cells killed by heat treatment or the like. The viable cells referred to here include, as described above, viable cells obtained from the culture, dried cells obtained from the viable cells, cells separated from the culture by a conventional method such as filtration, centrifugation or the like, and cells dried after separation and collection.

TS-15 and the mutants of the invention can be cultured by a conventional cultivation method for common bacteria. They may be cultured by any imaginable method such as solid culture or liquid culture (e.g. test tube shaking culture, reciprocal shaking culture, rotary shaking culture, jar fermentor culture or tank culture). As a culture medium, a proper combination of various carbon sources, nitrogen sources, organic salts and inorganic salts may be used. In general, the carbon sources include, for example, glucose, starch, glycerol, dextrin, sucrose, and animal and vegetable oils. The organic nitrogen sources include, for example, yeast extract, soybean flour, corn steep liquor, wheat germ, meat extract and peptone. The inorganic nitrogen sources include, for example, sodium nitrate, ammonium nitrate, ammonium sulfate and ammonium acetate. The organic salts and inorganic salts include, for example, acetates such as sodium acetate, etc.; carbonates such as calcium carbonate, sodium carbonate, etc.; chlorides such as sodium chloride, potassium chloride, etc.; phosphates such as potassium dihydrogenphosphate, disodium hydrogenphosphate, etc.; and sulfates such as ferrous sulfate, zinc sulfate, copper sulfate, etc. Although the cultivation temperature may be properly varied so long as the microorganism can be grown, it is preferably in the range of 20° C. to 40° C. Usually, the cultivation is carried out under aerobic conditions. Particularly when carried out in a jar fermentor or a culture tank, the cultivation is carried out while introducing sterile air. A method and conditions for the cultivation are not particularly limited so long as the microorganism can be grown. As discussed herein, the compositions of the invention may comprise sole sources of carbon (e.g., glucose) and nitrogen (yeast extract) which are particularly advantageous to the growth of TS-15 or its mutants, but which are not particularly utilized or even are inhibitive as to the growth of a target pathogen, e.g., *Salmonella*. Such media may be referred to as carbon and nitrogen "boosters."

Besides being effective against *Salmonella*, TS-15 and its mutants may be effective against other human pathogens as well, in particular, those Gram-negative or enteric pathogens which tend to cause gastrointestinal infections and symptoms, and which may be present as contamination or natural flora of produce-based crops. Examples include, other than *Salmonella*, pathogenic species of *Escherichia, Listeria, Shigella, Enterobacter* and *Staphylococcus*. Specific organisms can include *E. coli O*157:H7, *Enterobacter sakazakii, Staphylococcus aureus* and *Listeria monocytogenes.*

Bio-Control Compositions Comprising TS-15 and/or TS-15 Mutants

In one aspect, the present invention provides compositions comprising TS-15 and/or TS-15 mutants that may be applied to the soil, plant or plant organ sought to be treated as a biocontrol agent. The active ingredient in such compositions include active TS-15 cells or mutants thereof, or spores thereof, in a suitable carrier that is not harmful to plant or plant organs. Any suitable form of such compositions is contemplated, including liquids for spraying, gels, solids, powders, pellets, crystals, or any other type of physical form which could be applied to the soil, seed, plants or plant organs directly.

Bio-control formulations and other such compositions are well-known in the art. Any suitable bio-control agent format could be adapted to deliver the TS-15 or mutants thereof of the invention, so long as the compositions do not contain components which are harmful or inhibitive to TS-15 (or its mutants) or to any of the active bactericidal or bacteristatic active agents produced by the cells. An effective formulation could be prepared without undue experimentation by testing the effectiveness of the formulation over time using a known assay, a plug-assay as described in Example 1.

Examples of general bio-control formulations that may be utilized by the invention include, for example, U.S. Pat. No. 4,244,729 ("Sustained release pesticide compositions and process for making same"), U.S. Pat. No. 5,018,299 ("Pesticide delivery device"), U.S. Pat. No. 5,464,457 ("Soil fumigation with gasiform pesticide"), U.S. Pat. No. 5,662,915 ("Pesticide product derived from the plant *Tagetes minuta*"), U.S. Pat. No. 5,958,463 ("Agricultural pesticide formulations"), U.S. Pat. No. 5,972,915 ("Pesticide containing a synergistic combination of active ingredients"), U.S. Pat. No. 6,231,865 ("Natural pesticide"), U.S. Pat. No. 6,426,082 ("Aqueous suspension formulation of encapsulated pesticide"), U.S. Pat. No. 6,436,421 ("Pesticide compositions"), U.S. Pat. No. 6,447,811 ("Pesticide against plant-pathogenic microorganisms"), U.S. Pat. No. 6,505,436 ("Capsicum based pesticide and method of use"), U.S. Pat. No. 6,720,170 ("Pesticide microemulsions and dispersant/penetrant formulations"), and U.S. Pat. No. 7,563,748 ("Alcohol alkoxylate carriers for pesticide active ingredients"), each of which are incorporated herein by reference and may be utilized in delivering the bacteria of the invention.

Examples of bio-control formulations that are specifically designed to delivery biological ingredients, e.g., whole bacterial cells, including, for example, U.S. Pat. No. 5,283,060 ("*Bacillus*-containing pesticide granules"), U.S. Pat. No. 5,055,293 ("Biological pesticide"), U.S. Pat. No. 6,663,860 ("Biological pesticide"), and U.S. Pat. No. 7,393,528 ("Biological pesticide"), each of which are incorporated herein by reference in delivering the bacteria of the invention.

The amount or concentration of cells in the bio-control compositions of the invention can be determined without undue experimentation. Typical amounts of bacteria can include, for example, $10^2$, $10^3$, $10^4$, $10^5$, $10^6$, $10^7$, $10^8$, $10^9$, $10^{10}$, $10^{11}$, $10^{12}$, or more colony-forming units (CFU) per ml of composition.

The bio-control formulations of the invention may include various solid or liquid carriers. The solid carriers used in the formulation include, for example, mineral powders (e.g. kaoline clay, bentonite, diatomaceous earth, synthetic hydrated silicon oxide, talc, quartz, vermiculite and perlite), inorganic salts (e.g. ammonium sulfate, ammonium phosphate, ammonium nitrate, urea and ammonium chloride), organic powders (wheat flour, soybean flour, wheat bran, chitin, rice bran, skim milk powder and whole milk powder), activated carbon and calcium carbonate. The liquid carriers include, for example, water, glycerol, vegetable oils (e.g. soybean oil and rapeseed oil), liquid animal oils (e.g. fish oil), ethylene glycol, poly(ethylene glycol)s, propylene glycol and poly(propylene glycol)s.

The bio-control formulations of the invention may also be used in admixture with other insecticides, nematicides, acaricides, fungicides, bactericides, herbicides, plant growth regulators, spreaders, fertilizers, microbial materials, soil amendments and the like, or may be used together with them without mixing therewith.

In the control of plant diseases according to the present invention, the applying dosage (wet dosage) of the active ingredient of the strain of the genus *Paenibacillus* used is usually about 0.1 g to about 10000 g, preferably about 10 g to about 1000 g, per 10 ares. When the wettable powder, suspension, microcapsules or the like is used after being diluted with water, the cell concentration at the time of application is usually about $10^3$ CFU/mL to about $10^{11}$ CFU/mL, preferably about $10^5$ CFU/mL to about $10^9$ CFU/mL. The granules, dust, paste and the like may be applied as they are in the form of such a formulation without dilution.

When spores, vegetative cells or whole culture of the strain of the genus *Paenibacillus* is used, the applying dosage thereof is preferably about 0.1 g to about 10000 g (wet weight) per 10 acres. When the spores or vegetative cells are used after being diluted with water, the concentration thereof at the time of application is preferably about $10^3$ to about $10^{10}$ CFU/mL. The applying dosage of the substance capable of inducing disease resistance in plant is preferably approximately 0.001 g to 10000 g per 10 acres.

In the control of plant diseases according to the present invention, the strain of the genus *Paenibacillus* or substance capable of inducing disease resistance in plants of the present invention is preferably applied to the stalks and leaves, rooting zone and/or seeds of a plant. For actually applying the strain or substance, there are, for example, conventional methods such as a method of applying granules to a plant foot or soil and a method of applying a diluted liquid or an undiluted liquid to a plant foot or soil. Besides these methods, there may be adopted, for example, the same spraying method as a method for controlling diseases in above-ground part; a method of coating plant seeds with, or immersing them in, a mixture or each of the strain of the genus *Paenibacillus* or substance capable of inducing disease resistance in plants of the present invention, a solid carrier, an adhesive agent called a binder, and the like; a method of applying the strain or substance in admixture with a fertilizer, a soil amendment, compost and the like or applying the strain or substance together with them without mixing therewith; and a method using a microbial material obtained by adsorbing the strain of the genus *Paenibacillus* or substance capable of inducing disease resistance in plants of the present invention on a solid carrier and or without adding thereto organic nutrients (e.g. rice bran, malt extract and amino acids), fertilizer components, etc.

Both applying dosage and applying concentration of such formulations are varied depending on conditions such as the kind of the formulation, an application time, an application site, an application method, a cultivation method, the kind of a crop plant, the kind of a plant disease, the degree of damage, etc., and may be increased or decreased irrespective of the above-mentioned ranges.

Generally, the administration of such compositions may occur at any point in time between the "farm and the store," i.e., meaning intervention with the compositions of the invention may occur at any point in the production, distribution and sale of the plant and plant organs of the invention. For example, prior to growing a crop with a plant of interest (e.g., a tomato plant), the soil itself may be treated if it is suspected of carrying contamination of a human or plant pathogen, e.g., *Salmonella*. The *Salmonella* may have entered the soil system through run-off of nearby animal waste that is contaminated with the organism. Subsequently, the seeds and young plantlings may be treated by administering an effective dose of the bio-control compositions of the invention. One, two or more rounds of bio-control administration may be provided during the growth of the crops. Once harvested, the leaves, fruits or vegetables may be further treated with yet another round or more of treatment. Further treatment may be administered during any subsequent point of storage, processing, distribution, and sales.

Active Substances of TS-15 or Mutants Thereof

Another aspect of the invention pertains to the active substances of TS-15 which have the antagonistic activity against *Salmonella* and other pathogens. Such active substances may be peptides, enzymes or small molecules produced by TS-15 or mutants thereof which inhibit or kill a target pathogen, e.g., *Salmonella*. In certain embodiments, as such active substances are generally released from the cell during production, the extracellular extract of the TS-15 cells of the invention which contain such active substances can be used in the compositions of the invention in combination with whole cells or independent of the cells. An "isolated" or "purified" active substance thereof is substantially free of cellular material when produced by extraction from a bacterial system, or chemical precursors or other chemicals when chemically synthesized. The language "substantially free of cellular material" includes preparations of an TS-15 active substance which is separated from cellular components of the bacteria, or in particular, the bacterial spores on which it may be produced. In one embodiment, where the active substance is a peptide, the language "substantially free of cellular material" includes preparations having less than about 30% (by dry weight) of non-TS-15 peptides or protein (also referred to herein as contaminating protein), more preferably less than 20% (by dry weight) of non-TS-15 peptides or protein, still more preferably less than about 10% (by dry weight) of non-TS-15 peptides or protein and most preferably less than about 5% (by dry weight) of non-TS-15 peptides or protein.

Standard methodologies may be used without undue experimentation to isolate and purify active substances from TS-15 that have activity against a target pathogen, e.g., *Salmonella*. For example, fractionation techniques, such as column chromatography, can be used to separate the components of a culture supernatant into a plurality of individual fractions. The fractions can be tested to identify those containing active components that have activity against a target pathogen. Fractions having activity present may be subjected to further fractionation and/or other analytical techniques to identify the active substances of interest.

Probiotic Compositions Comprising TS-15 and/or TS-15 Mutants

In another aspect, the invention relates to the use of TS-15 or its mutants as a probiotic, which can be administered to a subject who has or is suspected of having a foodborne illness as a treatment regimen for the illness. For example, an individual who is at risk of having ingested *Salmonella*—contaminated tomatoes may ingest a probiotic of the invention that comprises TS-15 or a mutant thereof. Once ingested, the TS-15 or mutant thereof counteracts the *Salmonella* in the gastrointestinal region to help inhibit and/or kill the contaminating pathogen or inhibit or block the colonization of the pathogen in the gastrointestinal tract. The TS-15 or mutants of the invention may also be used as probiotics for administering to animals such as fowl to reduce the occurrence of foodborne pathogens, such as *Salmonella*, in the animal population, thereby reducing the exposure of humans to those foodborne pathogens through contact with the fowl or contact with produce that becomes contaminated by such pathogens.

It will be appreciated that the gastrointestinal microflora has been shown to play a number of vital roles in maintaining gastrointestinal tract function and overall physiological health. For example, the growth and metabolism of the many individual bacterial species inhabiting the gastrointestinal tract depend primarily upon the substrates available to them, most of which are derived from the diet. See e.g., Gibson G. R. et al., 1995. Gastroenterology 106: 975-982; Christi, S. U. et al., 1992. Gut 33: 1234-1238. These finding have led to attempts to modify the structure and metabolic activities of the community through diet, primarily with probiotics which are live microbial food supplements. The best known probiotics are the lactic acid-producing bacteria (i.e., *Lactobacilli*) and *Bifidobacteria*, which are widely utilized in yogurts and other dairy products. These probiotic organisms are non-pathogenic and non-toxigenic, retain viability during storage, and survive passage through the stomach and small intestine. Since probiotics do not permanently colonize the host, they need to be ingested regularly for any health promoting properties to persist. Commercial probiotic preparations are generally comprised of mixtures of *Lactobacilli* and *Bifidobacteria*, although yeast such as *Saccharomyces* have also been utilized.

Probiotic preparations were initially systematically evaluated for their effect on health and longevity in the early-1900's (see e.g., Metchinikoff, E., Prolongation of Life, William Heinermann, London 1910), although their utilization has been markedly limited since the advent of antibiotics in the 1950's to treat pathological microbes. See e.g., Winberg, et al, 1993. Pediatr. Nephrol. 7: 509-514; Malin et al, Ann. Nutr. Metab. 40: 137-145; and U.S. Pat. No. 5,176,911. Similarly, lactic acid-producing bacteria (e.g., *Bacillus, Lactobacillus* and *Streptococcus* species) have been utilized as food additives and there have been some claims that they provide nutritional and/or therapeutic value. See e.g., Gorbach, 1990. Ann. Med. 22: 37-41; Reid et al, 1990. Clin. Microbiol. Rev. 3: 335-344.

Therefore, probiotic microorganisms are those which confer a benefit when grown in a particular environment, often by inhibiting the growth of other biological organisms in the same environment. Examples of probiotic organisms include bacteria and bacteriophages which possess the ability to grow within the gastrointestinal tract, at least temporarily, to displace or destroy pathogenic organisms, as well as providing other benefits to the host. See e.g., Salminen et al, 1996. Antonie Van Leeuwenhoek 70: 347-358; Elmer et al, 1996. JAMA 275: 870-876; Rafter, 1995. Scand. J. Gastroenterol. 30: 497-502; Perdigon et al, 1995. J Dairy Sci. 78: 1597-1606; Gandi, Townsend Lett. Doctors & Patients, pp. 108-110, January 1994; Lidbeck et al, 1992. Eur. J. Cancer Prev. 1: 341-353.

While the gastrointestinal microflora presents a microbial-based barrier to invading organisms, pathogens often become established when the integrity of the microbiota is impaired through stress, illness, antibiotic treatment, changes in diet, or physiological alterations within the G.I. tract. For example, *Bifidobacteria* are known to be involved in resisting the colonization of pathogens in the large intestine. See e.g., Yamazaki, S. et al., 1982. *Bifidobacteria* and Microflora 1: 55-60. Similarly, the administration of *Bifidobacteria breve* to children with gastroenteritis eradicated the causative pathogenic bacteria (i.e., *Campylobacter jejuni*) from their stools (see e.g., Tojo, M., 1987. Acta Pediatr. Jpn.

29: 160-167) and supplementation of infant formula milk with *Bifidobacteria bifidum* and *Streptococcus thermophilus* was found to reduce rotavirus shedding and episodes of diarrhea in children who were hospitalized (see e.g., Saavedra, J. M., 1994. The Lancet 344: 1046-109.

In addition, some lactic acid producing bacteria also produce bacteriocins which are inhibitory metabolites which are responsible for the bacteria's anti-microbial effects. See e.g., Klaenhammer, 1993. FEMS Microbiol. Rev. 12: 39-85; Barefoot et al., 1993. J. Diary Sci. 76: 2366-2379. For example, selected *Lactobacillus* strains which produce antibiotics have been demonstrated as effective for the treatment of infections, sinusitis, hemorrhoids, dental inflammations, and various other inflammatory conditions. See e.g., U.S. Pat. No. 5,439,995. Additionally, *Lactobacillus reuteri* has been shown to produce antibiotics which possess anti-microbial activity against Gram negative and Gram positive bacteria, yeast, and various protozoan. See e.g., U.S. Pat. Nos. 5,413,960 and 5,439,678.

Thus, in accordance with this aspect of the invention, strain TS-15 and mutants thereof may be utilized as probiotics to prevent or treat foodborne illnesses, in particular, those that affect the gastrointestinal tract. The present invention discloses compositions and methodologies for the utilization of these compositions comprising non-pathogenic, probiotic *Paenibacillus* strains which may be used to mitigate the deleterious physiological effects of gastrointestinal tract pathogens, including *Salmonella* and other enteric foodborne pathogens in both humans and animals, by the colonization (or more-correctly, re-colonization) of the gastrointestinal tract with probiotic microorganisms of the invention.

In another embodiment of the present invention, the TS-15 strain of the invention may be combined with a therapeutically-effective dose of an antibiotic that is effective against a foodborne pathogen. In preferred embodiments of the present invention, the antibiotic may include: Gentamicin; Vancomycin; Oxacillin; Tetracyclines; Nitrofurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

Additionally disclosed herein are compositions and methods for the use of the probiotic bacteria of the invention, namely the TS-15 strain and mutants thereof, in administering to humans and/or animals to treat or prevent foodborne illnesses or to block or mitigate the proliferation of those pathogens, e.g., *Salmonella*, which cause the foodborne illnesses. The present invention also discloses therapeutic compositions, therapeutic systems, and methods of use for the treatment and/or prevention of various pathogenic bacterial gastrointestinal tract infections, particularly those infections associated with antibiotic-resistant pathogens.

In one embodiment of the present invention, a therapeutic composition comprising a viable, non-pathogenic *Paenibacillus* bacterium, preferably TS-15 or mutants thereof, in a pharmaceutically-acceptable carrier suitable for oral administration to the gastrointestinal tract of a human or animal, is disclosed. In another embodiment, the TS-15 strain is included in the therapeutic composition in the form of spores. In another embodiment, the TS-15 strain is included in the composition in the form of a dried cell mass.

In another aspect of the present invention, a compositions comprising an extracellular product of the TS-15 strain of the invention in a pharmaceutically-acceptable carrier suitable for oral administration to a human or animal, is disclosed. In a preferred embodiment, the extracellular product is a supernatant or filtrate of a culture of TS-15 or a mutant thereof which contains at least one bactericidal or bacteristatic active agent that mitigates the colonization or proliferation of a foodborne pathogen in the gastrointestinal tract, e.g., *Salmonella*.

Another aspect of the invention is a method of preventing or treating a bacterial gastrointestinal infection in a human, e.g., salmonellosis, comprising the steps of orally administering to a human subject a food or drink formulation containing viable colony forming units of a non-pathogenic *Paenibacillus* stain of the invention, preferably strain TS-15 or a mutant thereof, and allowing the bacteria to grow in the human subject's gastrointestinal tract.

In one embodiment of the aforementioned method, the step of allowing the probiotic bacteria to grow, further includes inhibiting growth of gastrointestinal foodborne pathogens, including, for example, *Salmonella* Newport, a pathogenic strain of *Shigella, Escherichia, Enterobacter, Listeria* or *Staphylococcus, E. coli* O157:H7, *Enterobacter sakazakii, Staphylococcus aureas*, or *Listeria monocytogenes, Candida* species, *Staphylococcus* species, *Streptococcus* species, *Proteus* species, *Pseudomonas* species, *Escherichia coli, Clostridium* species, *Klebsiella* species, and *Enterococccus* species. Probiotic formulations and methods of administration are well known in the art, including in U.S. Pat. Nos. 7,906,112, 7,807,440, 7,807,151, 7,785,635, 7,759,105, 7,749,509, 7,736,509, 7,731,976, 7,713,726, and 7,708,988, each of which are incorporated herein by reference.

The probiotic compositions of the invention can be administered together with other known therapies for foodborne illnesses, including antibiotics.

Uses and Methods of the Invention

In another aspect, the invention pertains to the use of strain TS-15 or mutants thereof, or antibiotics or peptides obtained from TS-15 or its mutants as an agent that is antagonistic against human foodborne pathogens that reside on plant hosts. The bacterial strains and bioactive mutants or modified forms thereof of the present invention can be used as a bio-control agents, and, in particular, as a biocontrol agent against foodborne pathogens, including pathogenic species of *Shigella, Escherichia, Enterobacter, Listeria* or *Staphylococcus*, including *Salmonella enterica* serovar Newport, *E. coli* O157:H7, *Enterobacter sakazakii, Staphylococcus aureas*, and *Listeria monocytogenes*. In addition, the invention contemplates the use of the TS-15 strain or its mutants, or any isolatable active component produced by the TS-15 or its mutants, for controlling plant diseases caused by a variety of bacteria, viruses and fungi, including those listed herein above. In particular, the TS-15 strain of the invention or its active components that may be isolated therefrom may be used to treat plant diseases of plants of the Solanaceae (or Nightshade family) family, which include, for example, tomato and pepper plants. However, no particular limitation is contemplated as to which plants or plant organs that may treated by the TS-15 strain (or TS-15 mutants) of the invention. Such plants or plant organs that may be treated by the strains of the invention, may include, for example, other common sources of foodborne pathogens, such as, but not limited to leafy greens, celery, and other culinary vegetables, podded vegetables, bulb and stem vegetables, root and tuberous vegetables, as well as certain fruits, such as, cantaloupe.

It will be appreciated that Solanaceae is a family of flowering plants that contains a number of important agricultural crops as well as many toxic plants. The family is also informally known as the nightshade—or potato family. The family includes, but it not limited to, *Datura* (Jimson weed), *Mandragora* (mandrake), *belladonna* (deadly nightshade), *Capsicum* (paprika, chili pepper), *Solanum* (potato, tomato, aubergine or eggplant), *Nicotiana* (tobacco), and *Petunia* (petunia). With the exception of tobacco (Nicotianoideae) and petunia (Petunioideae), most of the economically important genera are contained in the sub-family Solanoideae. The Solanaceae family is characteristically ethnobotanical, that is, extensively utilized by humans. It is an important source of food, spice and medicine.

Leafy greens and salad vegetables that are contaminated with foodborne pathogens (or plant pathogens) may be treated using the strains of the invention. Such vegetables can include, for example, Amaranth (*Amaranthus cruentus*); Arugula (*Eruca sativa*); Beet greens (*Beta vulgaris* subsp. *vulgaris*); Bitterleaf (*Vernonia calvoana*); Bok choy (*Brassica rapa* Chinensis group); Broccoli Rabe (*Brassica rapa* subsp. *rapa*); Brussels sprout (*Brassica oleracea* Gemmifera group); Cabbage (*Brassica oleracea* Capitata group); Catsear (*Hypochaeris radicata*); Celery (*Apium graveolens*); Celtuce (*Lactuca sativa* var. *asparagina*); Ceylon spinach (*Basella alba*); Chard (*Beta vulgaris* var. *cicla*); Chaya (*Cnidoscolus aconitifolius* subsp. *aconitifolius*); Chickweed (*Stellaria*); Chicory (*Cichorium intybus*); Chinese cabbage (*Brassica rapa* Pekinensis and Chinensis groups); Chinese Mallow (*Malva verticillata*); Chrysanthemum leaves (*Chrysanthemum coronarium*); Collard greens (*Brassica oleracea*); Corn salad (*Valerianella locusta*); Cress (*Lepidium sativum*); Dandelion (*Taraxacum officinale*); Endive (*Cichorium endivia*); Epazote (*Chenopodium ambrosioides*); Fat hen (*Chenopodium album*); Fiddlehead (*Pteridium aquilinum, Athyrium esculentum*); Fluted pumpkin (*Telfairia occidentalis*); Garden Rocket (*Eruca sativa*); Golden samphire (*Inula crithmoides*); Good King Henry (*Chenopodium bonus-henricus*); Greater Plantain (*Plantago major*); Kai-lan (*Brassica rapa* Alboglabra group); Kale (*Brassica oleracea* Acephala group); Komatsuna (*Brassica rapa* Pervidis or Komatsuna group); Kuka (*Adansonia* spp.); Lagos bologi (*Talinum fruticosum*); Lamb's lettuce (*Valerianella locusta*); Land cress (*Barbarea verna*); Lettuce (*Lactuca sativa*); Lizard's tail (*Houttuynia cordata*); Melokhia (*Corchorus olitorius, Corchorus capsularis*); Miner's Lettuce; Mizuna greens (*Brassica rapa* Nipposinica group); Mustard (*Sinapis alba*); Napa cabbage (*Brassica rapa* Pekinensis group); New Zealand Spinach (*Tetragonia tetragonioides*); Orache (*Atriplex hortensis*); Pak choy (*Brassica rapa* Chinensis group); Paracress (*Acmella oleracea*); Pea sprouts/leaves (*Pisum sativum*); Polk (*Phytolacca americana*); Radicchio (*Cichorium intybus*); Samphire (*Crithmum maritimum*); Sea beet (*Beta vulgaris* subsp. *maritima*); Seakale (*Crambe maritima*); Siena Leone bologi (*Crassocephalum* spp.); Soko (*Celosia argentea*); Sorrel (*Rumex acetosa*); Spinach (*Spinacia oleracea*); Summer purslane (*Portulaca oleracea*); Swiss chard (*Beta vulgaris* subsp. *cicla* var. *flavescens*); Tatsoi (*Brassica rapa* Rosularis group); Turnip greens (*Brassica rapa* Rapifera group); Watercress (*Nasturtium officinale*); Water spinach (*Ipomoea aquatica*); Winter purslane (*Claytonia perfoliata*); and Yarrow (*Achillea millefolium*).

Podded vegetables that are contaminated with foodborne pathogens (or plant pathogens) may be treated using the strains of the invention. Such vegetables can include, for example, American groundnut (*Apios americana*), Azuki bean (*Vigna angularis*), Black-eyed pea (*Vigna unguiculata* subsp. *unguiculata*), Chickpea (*Cicer arietinum*), Common bean (*Phaseolus vulgaris*), Drumstick (*Moringa oleifera*), Dolichos bean (*Lablab purpureus*), Fava bean (*Vicia faba*), Garbanzo (*Cicer arietinum*), Green bean (*Phaseolus vulgaris*), Guar (*Cyamopsis tetragonoloba*), Gumbo (*Abelmoschus esculentus*), Horse gram (*Macrotyloma uniflorum*), Indian pea (*Lathyrus sativus*), Lentil (*Lens culinaris*), Lima Bean (*Phaseolus lunatus*), Moth bean (*Vigna acontifolia*), Mung bean (*Vigna radiata*), Okra (*Abelmoschus esculentus*), Pea (*Pisum sativum*), Peanut (*Arachis hypogaea*), Pigeon pea (*Cajanus cajan*), Ricebean (*Vigna umbellata*), Runner bean (*Phaseolus coccineus*), Soybean (*Glycine max*), Tarwi (tarhui, chocho; *Lupinus mutabilis*), Tepary bean (*Phaseolus acutifolius*), Urad bean (*Vigna mungo*), Velvet bean (*Mucuna pruriens*), Winged bean (*Psophocarpus tetragonolobus*), and Yardlong bean (*Vigna unguiculata* subsp. *sesquipedalis*).

Bulb and stem vegetables that are contaminated with foodborne pathogens (or plant pathogens) may be treated using the strains of the invention. Such vegetables can include, for example, Asparagus (*Asparagus officinalis*), Cardoon (*Cynara cardunculus*), Celeriac (*Apium graveolens* var. *rapaceum*), Celery (*Apium graveolens*), Elephant Garlic (*Allium ampeloprasum* var. *ampeloprasum*), Florence fennel (*Foeniculum vulgare* var. *dulce*), Garlic (*Allium sativum*), Kohlrabi (*Brassica oleracea* Gongylodes group), Kurrat (*Allium ampeloprasum* var. *kurrat*), Leek (*Allium porrum*), Lotus root (*Nelumbo nucifera*), Nopal (*Opuntia ficus-indica*), Onion (*Allium cepa*), Spring Onion/Scallion (*Allium wakegi*), Prussian asparagus (*Ornithogalum pyrenaicum*), Shallot (*Allium cepa* Aggregatum group), Welsh onion (*Allium fistulosum*), and Wild leek (*Allium tricoccum*).

Root and tuberous vegetables that are contaminated with foodborne pathogens (or plant pathogens) may be treated using the strains of the invention. Such vegetables can include, for example, Ahipa (*Pachyrhizus ahipa*), Arracacha (*Arracacia xanthorrhiza*), Bamboo shoot (*Bambusa vulgaris* and *Phyllostachys edulis*), Beetroot (*Beta vulgaris* subsp. *vulgaris*), Burdock (*Arctium lappa*), Broadleaf arrowhead (*Sagittaria latifolia*), Camas (Camassia), Canna (*Canna* spp.), Carrot (*Daucus carota*), Cassava (*Manihot esculenta*), Chinese artichoke (*Stachys affinis*), Daikon (*Raphanus sativus* Longipinnatus group), Earthnut pea (*Lathyrus tuberosus*), Elephant Foot yam (*Amorphophallus_paeoniifolius*), Ensete (*Ensete ventricosum*), Ginger (*Zingiber officinale*), Gobo (*Arctium lappa*), Hamburg parsley (*Petroselinum crispurn* var. *tuberosum*), Jerusalem artichoke (*Helianthus tuberosus*), Jicama (*Pachyrhizus erosus*), Manioc (*Manihot esculenta*), Mooli (*Raphanus sativus* Longipinnatus group), Parsnip (*Pastinaca sativa*), Pignut (*Conopodium majus*), Plectranthus (*Plectranthus* spp.), Potato (*Solanum tuberosum*), Prairie turnip (*Psoralea esculenta*), Radish (*Raphanus sativus*), Horseradish (*Annoracia rusticana*), Rutabaga (*Brassica napus* Napobrassica group), Salsify (*Tragopogon porrifolius*), Scorzonera (*Scorzonera hispanica*), Skirret (*Sium sisarum*), Swede (*Brassica napus* Napobrassica group), Sweet Potato or Kumara (*Ipomoea batatas*), Taro (*Colocasia esculenta*), Ti (*Cordyline fruticosa*), Tigernut (*Cyperus esculentus*), Turnip (*Brassica*

*rapa* Rapifera group), Ulluco (*Ullucus tuberosus*), Water chestnut (*Eleocharis dulcis*), Yacón (*Smallanthus sonchifolius*), and Yam (*Dioscorea* spp.).

Compositions can be prepared comprising the biocontrol agents of the invention, i.e., containing the TS-15 strain and mutants thereof and/or active agents obtained and isolated from the TS-15 strain. The compositions can be dried or hydrated. Any suitable formulation can be used. In general, bio-control formulations are well-known in the art. In a preferred embodiment, the bacteria is applied in a viable form which permits it to sustain itself in the soil or on the plants or crops being treated to provide a biocontrol effect over a long period of time. Bioassay methods can be used to determine the presence of the bacteria in the environment.

In accordance with another aspect of the invention, TS-15 active agents (e.g., obtained from the supernatant of a TS-15 culture) can be used in the bio-control compositions of the invention against the foodborne and/or plant pathogens of the invention. The TS-15 active agents can be applied to a crop at any desired stage of crop growth to act against the *Salmonella* or other foodborne and/or plant pathogens that may be present on the target plants, blossoms or fruits.

The bacterial strains and any isolatable active agents (e.g., peptide antibiotics) of the present invention can be applied as bio-control agents in any desired way. In one embodiment, the bacterial strains or active agents are applied in a carrier to facilitate application and to reduce crop maintenance time. A preferred route of administration is using a spray approach. Spray bio-control formulations, methods and systems are well known in the art and examples of such can be found in U.S. Pat. Nos. 6,855,327, 6,541,426, 6,664,213, 6,778,887, 6,855,327, 7,238,365, and 5,626,858, each of which are incorporated herein by reference.

In the control of those foodborne pathogens and plant pathogens of interest on plants or plant organs of the invention, the TS-15 strain or mutants thereof or any isolatable active substances capable of disease resistance in plants of the present invention can be applied to the soil or to any part of the plants being treated, including the stalks and leaves, blossoms (to prevent internalization of pathogens in fruit, e.g., tomato), rooting zone and/or seeds of the plants. For actually applying the strain or substance, there are, as mentioned herein, conventional methods such as a method of applying granules to a plant root or soil and a method of applying a diluted liquid or an undiluted liquid to a plant root or soil. Besides these methods, there may be adopted, for example, the same spraying method as a method for controlling diseases in above-ground part; a method of coating plant seeds with, or immersing them in, a mixture or each of the strain of the genus *Paenibacillus* or substance capable of inducing disease resistance in plants of the present invention, a solid carrier, an adhesive agent called a binder, and the like; a method of applying the strain or substance in admixture with a fertilizer, a soil amendment, compost and the like or applying the strain or substance together with them without mixing therewith; and a method using a microbial material obtained by adsorbing the strain of the genus *Paenibacillus* or substance capable of inducing disease resistance in plants of the present invention on a solid carrier and or without adding thereto organic nutrients (e.g. rice bran, malt extract and amino acids), fertilizer components, etc.

Both applying dosage and applying concentration of such formulations are varied depending on conditions such as the kind of the formulation, an application time, an application site, an application method, a cultivation method, the kind of a crop plant, the kind of a plant disease, the degree of damage, etc., and may be increased or decreased irrespective of the above-mentioned ranges.

The following examples further demonstrate several embodiments of this invention. While the examples illustrate the invention, they are not intended to limit it.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1. Identification and Characterization of *Paenibacillus alvei* Strain TS-15

Foodborne illness ranks among the most serious of public health concerns, and of these illnesses salmonellosis remains one of the most common, causing about 30,000 cases of gastrointestinal illness per year in the US alone. Fresh tomatoes, grown predominantly on the East Coast, have emerged as a perennial and complex transmission vehicle for human illness caused by *Salmonella enterica* serovar Newport. In order to mitigate the incidence of tomato-borne outbreaks by *Salmonella*, ecologically sound intervention strategies are essential.

This Example demonstrates the discovery of a new bacterial strain TS-15 in the genus *Paenibacillus* that inhibits the growth of *Salmonella* and other significant foodborne pathogens on the surface of tomatoes and tomato plants, as well as the fruit, leaves and blossoms of other plants. The strain TS-15 not only antagonizes growth of *Salmonella*, but actually eliminates pre-existing colonies of the pathogen found to contaminate various organs of tomato, including fruit, leaves and blossoms, an the various organs of other plants.

The Example further evaluated the efficacy in vivo for two antagonists (A6-6i-x and TS-15) on red round tomatoes as biocontrol agents against *Salmonella*. Tomato challenges were conducted following 24 hr co-inoculations of S. Newport and antagonists in buffered peptone water on sterilized tomato fruit surfaces. Recovery on tomatoes where pathogen was added first revealed a one log reduction in viable *Salmonella* for strain A6-6i-x. Remarkably, strain TS-15, found associated with tomato plants, revealed a six log decrease in *Salmonella* compared to tomatoes inoculated with pathogen alone. When antagonist was added first, A6-6i-x again revealed a modest one log reduction while TS-15 yielded a precipitous five log drop in *Salmonella* cell inoculum, completely preventing pathogen recovery from fruit surfaces. These data suggest a role for these epiphytic bacteria, and, in particular, TS-15, endemic to the tomato growing regions of the mid-Atlantic, as naturally effective antagonists in preventing contamination of tomatoes by *Salmonella*.

Introduction

Foodborne pathogens represent a significant and growing public health threat in the US and around the world. The large-scale production and recent increase in the importation of a diverse array of food commodities have spawned bacterial contaminations that have been implicated in a number of foodborne disease epidemics. Foodborne illness ranks among the most serious of public health concerns, and of these illnesses Salmonellosis remains one of the most common, causing about 30,000 cases of gastrointestinal illness per year in the US alone. Many of these cases have implicated tomatoes as a transmission vehicle in multiple *Salmonella* foodborne outbreaks.

Due to the prevalence of *Salmonella* induced outbreaks and its effect on society both health wise and economically, new combative measures and strategies must be developed and effectively instituted in order to limit the spread of epidemics associated with *Salmonella*. With the goal of finding new and natural means of protecting the food supply, the native flora of several produce-associated plants as well as feral plants associated in proximity to produce farmlands were screened for possible epiphytic bacteria with antagonistic activity against *Salmonella* Newport, a common strain associated with tomato outbreaks. The purpose driving the screening of plant-associated bacteria and yeasts was to target and isolate microorganisms that were native already to these mid-Atlantic farmlands, have an antagonistic efficacy against foodborne pathogens on those native plants, and subsequently, serve upon re-introduction as a biocontrol agent.

Through a multi-phase in vitro screening system, which involved the use of both the Bioscreen, to test inhibition effects in broth, and the use of the in vitro plug assay to test out the antagonistic bacteria in competitive micro-arenas for study of interactions between S. Newport and potential antagonists, the isolation of several natural plant-associated bacteria were discovered from the environment that block the growth of S. Newport. The screening process revealed two competitive *Salmonella* inhibiting bacteria denoted as A6-6i-x and TS-15.

After extensive in vitro screening the antagonists were tested on the surface of a tomato to challenge S. Newport that was placed on before or after the antagonist. The S. Newport was mixed with PBS and placed on the tomato surface and allowed to dry. Afterwards a mixture of antagonist and TSB was placed on top and allowed to dry and then the tomato was placed in a humidity chamber in a 30° C. incubator. The same was repeated but with putting the antagonist on first and then placing the *Salmonella* on top. The tomato was washed in a sterile plastic bag and the suspension was plated on XLD plates and then counted. The strains showed differing inhibition strengths on the tomato surface with one arising as a clear superior contender, identified as TS-15. These bacteria may have a future as biocontrol measures for *Salmonella* and other pathogens on mid-Atlantic produce and other similar commodities grow in the South and the Western parts of the country.

The following materials and methods were employed in this Example.

Materials and Methods:

Strain Isolation and Screening.

The native microflora of various plant organs including (leaves, shoots, roots, and blossoms) and soil at various Eastern Shore tomato growing regions were examined. Three grams of plant material or soil were mixed for about 5 minutes in 1 ml of phosphate-buffered saline (PBS). 100 μl was plated onto Nutrient Yeast Glucose agar (NYGA). Ten colonies with unique morphologies which developed within 48 hours at 30° C. under aerobic conditions were picked for further purification. These colonies were also tested using the 3% KOH test. The KOH test is a rapid test for Gram differentiation without staining.

The colony of pure cultures was then tested for antagonistic activity in vitro using an agar plug method as discussed in Visser R. et al., Appl. Environ. Microbiol. 1986 552-555, which is incorporated herein in its entirety.

Briefly, pour plates were made of one of the test organisms by mixing 4 ml suspension of an overnight plate culture with sterile water in 20 ml of TSA agar. After incubation at 30° C. overnight, agar plugs were punched from the agar with a sterile 10 mm stainless steel borer. The agar plugs were placed on TSA agar containing a lawn of $10^6$ cells of *Salmonella enterica* serovar Newport and incubated under 35° C. The clear zones "zones of inhibition" surrounding the plugs were measured at incubation periods of 24 hours (1 day), 48 hours (2 days), and 96 hours (4 days), respectively. The experiment was done in triplicate to ensure repeatability. Isolates with greater zones of inhibition against S. Newport were selected for additional testing and taxonomic characterization.

Phenotypic and Biochemical Characterizations of the Isolates with Potential Antimicrobial Activity.

The morphological characteristics of the potential antagonists were observed by Gram staining and spore staining. The isolates were further tested with Vitek® 2 compact Biochemical identification system (BIOMERIEUX, INC., Durham, N.C.). VITEK® 2 compact colorimetric cards were read and interpreted automatically with the VITEK® 2 compact system, version 01.01b.

16S rRNA Gene Amplification, and Sequencing.

Genomic DNA of the isolates was extracted using WIZARD® genomic DNA purification kit (PROMEGA). A pair of universal primers specific for bacterial 16S rRNA, Eubac27 and R1492 (sequences available in DeLong et al., E. F. Proc. Natl. Acad. Sci. USA, 1992 (89): 5685-5689, which is incorporated herein by reference in its entirety), were used to amplify the corresponding 16S rRNA gene. PCR amplification of the 16S rRNA was performed with a Hotstart Taq plus DNA polymerase kit (QIAGEN, Valencia, Calif.) under the following conditions: after an initial 5-min incubation at 95° C., the mixture was subjected to 30 cycles, each including 1 min at 95° C., 1 min at 58° C., and 1 min at 72° C. A final extension was performed at 72° C. for 10 min. Primers 4F, 27F, 357F, 578F, 1000R, and 1492R were used for sequencing (sequences available in Gonzalez-Escalona et al. FEMS Microbiology Letters 2005 (246): 213-219, and Turner, S. et al. Journal of Eukaryotic Microbiology 1999 (46): 327-338, which are incorporated herein by reference in their entireties). BLAST algorithm was used for homology search against Genbank. Only results from the highest-score queries were considered for phylotype identification, with 99% minimum similarity.

Determination of Efficacy and Broad Spectrum of Inhibition In Vitro.

Candidate epiphytic microbes that demonstrated antagonistic activity in vitro against S. Newport and themselves are generally regarded as commensal to humans and tomato after taxonomic identification were then be subjected to agar plug method described above to determine the efficacy against a broad spectrum of major foodborne pathogens including *Listeria monocytogenes, Enterobacter sakazakii, Escherichia coli O*157:H7, *Shigella flexneri*, methicillin-resistant *Staphylococcus aureus* (MRSA), and several distinct *Salmonella enterica* subspecies. Bactericidal effects against pathogenic strains in the zone of inhibition were confirmed when pathogens were unable to be revived on TSA plates.

In a separate experiment, antimicrobial activities were characterized using the Bioscreen assay. Specifically, an overnight culture of S. Newport and other major foodborne pathogens described above was diluted using PBS and added to supernatant from one of the antagonist candidates with a final concentration of $10^4$ cfu/ml cells. The supernatant was filter sterilized through a 0.22 um filter for use. The optical density at 600 nm was measured automatically each 20 min during 24 h in a Bioscreen C Automated Microbiology Growth Curve Analysis (GROWTH CURVES USA, Piscataway, N.J.). For each time point, the average optical density was calculated from five independent measurements.

The Bioscreen C Automated Microbiology Growth Curve Analysis System directly measures microorganism growth. As microorganisms grow, they increase the turbidity of their growth medium. By measuring the turbidity of this medium over time, an optical density (O.D.) curve can be generated. The curve reflects the growth (increased concentration) of the organism of interest. Further information on the use of a Bioscreen C machine can be found in the literature, for example, in: Dong Y, Palmer S R, Hasona A, Nagamori S, Kaback H R, Dalbey R E, Brady L J, *Functional overlap but lack of complete cross-complementation of Streptococus mutans and Escherichia coli YidC orthologs*, Journal of Bacteriology 190: (2008) 2458-2469; George, S M, A. Métris A, Stringer S C, *Physiological state of single cells of Listeria innocua in organic acids*, International Journal of Food Microbiology 124: 2008. 204-210; de Crecy E, Metzgar D, Allen C, Pénicaud M, Lyons B, Hansen C J, de Crécy-Lagard V, 2007. *Development of a novel continuous culture device for experimental evolution of bacterial populations*, Applied Microbiology and Biotechnology 77: (2007) 489-496; Tauk-Tornisielo S M, Vieira J M, Govone J S, *Use of Bioscreen C for growth of Mucor hiemalis* in different carbon and nitrogen sources, Brazilian Journal of Microbiology 38: 2007. 113-117; Escalada M G, Russell A D, Maillard J-Y, Ochs D, *Triclosan-bacteria interactions: single or multiple target sites?* Letters in Applied Microbiology 41:(2005) 476-481; and Brehm-Stecher B F, Johnson E A, *Single-cell microbiology: tools, technologies, and applications*, Microbiology and Molecular Biology Reviews 68:(2004) 538-559, each of which are incorporated by reference in their entireties.

Efficacy Evaluation Against S. Newport on Tomatoes.

Red round ripe tomatoes (130±20 g each) were used in each experiment. The tomatoes were purchased from a local supermarket and stored at 4° C. for a maximum of 3 days before they were used in experiments. The strain of S. Newport was cultured in 5 ml of TSB at 37° C. overnight before it was used as inoculum. Bacteria cells were washed twice with PBS and resuspended in 5 ml of PBS before being applied to tomatoes. Each antagonist candidate strain was cultured on a TSA plate overnight to make a lawn. A quarter of the bacterial lawn was scraped off the TSA plate with a sterile inoculation loop and transferred to 10 ml of PBS. Cell suspensions were prepared by washing bacteria cells twice with PBS and resuspending in 5 ml of fresh TSB for all experiments.

Tomatoes were warmed up to room temperature (RT) before each experiment. RT tomatoes were washed with warm water for 30 sec to remove any oil or wax (i.e., luster) that had been applied first and then wiped with 75% ethanol soaked paper towels for surface sterilization. The clean tomatoes were placed stem scar-end-down on a metal tray rack in a biosafety cabinet to dry. 20 ul of the suspension of *Salmonella* cells was applied to a 3-cm-diameter circle on the side of the tomato which is equidistant from both ends of the tomato. After fully dry, 40 ul of the antagonist suspension or 40 ul of TSB only was placed on top of the *Salmonella* inoculum. Inoculated tomatoes were put in the humidity chamber after drying for one and a half hour. The humidity chamber was filled with 1.5 L of water, closed and put in the 30° C. incubator. After 24 hours each tomato was placed in a stomacher bag containing 30 ml of PBS and hand-rubbed for 5 minutes to dislodge surface inoculated *Salmonella*. The PBS wash water was serial diluted in PBS and surface plated on XLD agar.

Field Trials in High Tunnel.

The best antagonist candidate strain was subjected to field trials in a high tunnel whereby *Salmonella* survival was challenged in the presence of the antagonist on tomato leaves, blossoms and fruits of red-round producing whole, intact, live tomato plants. Trials were performed in 2010 (July through September) on tomato cultivar BHN602 in an insect-screened high tunnel at United States Department of Agriculture (USDA), Beltsville Agricultural Research Center (BARC) north farm, Beltsville, Md. Tomato plants were started from seeds in a BARC greenhouse. Seedlings were grown in commercial organic peat mix and fertilized with Neptune's Harvest Organic Fish/Seaweed Blend fertilizer before and after transplanting. In the high tunnel, fertilizer was supplied from a single injector through drip tape supplemented with an OMRI-approved calcium source to prevent blossom end rot. Black plastic mulch was used to cover the 8 planting beds (2'×20' each) over the drip tape. Planting slits were made in the black plastic at 15" intervals to accommodate 13 transplants per bed. Plants were staked and fitted with nylon support strings when 10" high. Plants were irrigated immediately after transplanting and at least weekly to achieve 1-1.5" water and meet fertility requirements. Soil moisture was monitored by irrometers and digitally on the Hobo weather station that is located in the center of the high tunnel along with temperature, RH, PAR, and total SR sensors.

A split-plot design is used with the whole plot effect as *Salmonella* and antagonist [present or absent] and a single dose as the sub-plot; inoculation sites including leaf, blossom and tomato fruit were each assigned a second level sub-plot, with each inoculation site as an independent experiment; and day of harvest post-inoculation as a repeated measure. The second level corresponds to harvests used for 0 day (2 hrs after inoculation as a benchmark for % recovery), 1 day, 2 days, 3 days, and 5 or 6 days persistence trials, respectively. Thirteen plants are planted in each plot. One plant on each end of each bed served as an uninoculated border plant, leaving 11 replicates per plot.

Attenuated S. Newport strain ΔtolC::aph and antagonist strain TS-15 were used in this field trial. Three leaves, blossoms or tomatoes (at late 'breaker' to 'red' stage) of each plant were used for inoculation. TSB suspensions of S. Newport strain ΔtolC::aph after being washed twice in PBS were spot inoculated to the marked leaves (20 μl), blossoms (10 μl), and tomatoes (20 μl) with a final concentration of ~$10^9$ CFU/ml. The inoculation spots were allowed to air dry (~1 h) before applying the antagonist. Antagonist cell suspensions were made from a bacteria lawn of strain TS-15. After a PBS wash 2×, 10 ml of TSB was used to resuspend the cells. 40 μl of antagonist cell suspension or just plain TSB were applied to the same inoculation spot on leaves and tomatoes, 10 μl to blossoms, of each plant in the 'with' or 'without' antagonist group, respectively.

Leaves, blossoms, and tomatoes were harvested at day 0, day 1, day 2, day 3, and day 5 (for blossoms) or day 6 (for leaves and tomatoes) post inoculation. Inoculated leaves, blossoms, or tomatoes from each plant were removed with sterile scissors and placed in a plastic zip-lock bag, which was sealed and transported in a cooler to the laboratory for analysis within 1 h. For leaves and blossoms, each sample bag was added with 15 ml and 10 ml of PBS, respectively, and hand-rubbed for 3 min to dislodge surface populations of *Salmonella*. For tomato, each sample bag was filled with 30 ml of PBS and subjected to sonication at 55 Hz/min for 30 sec. The PBS was diluted or concentrated through filtration (at later time points of the experiment) and surface plated (0.1 ml in duplicate) on TSA-kan (50 µg/ml). Plates were incubated at 37° C. overnight and counted for kanamycin resistant colonies. Two colonies were randomly picked from each TSA-kan plate and confirmed by PCR using a set of verification primers.

Survival and Persistence of TS-15 in the Field.

Survival of antagonist strain TS-15 was evaluated in a tomato field at The Virginia Eastern Shore Agricultural Research and Extension Center (AREC). In brief, rows of tomato cultivar BHN602 were planted by hand with 1 m between rows. Fifteen plants randomly were selected for inoculation in each row. Two border rows of tomato plants were maintained to surround an experimental row and a control row for each time point and were not treated. Biomass of antagonist TS-15 was produced in TSB media in 500 ml flask and then transferred to sterile spray bottles, transported to the field on ice, and used within 24 h. A spray inoculation method was used to mimic the industrial arrival of inoculum into the field. The survival of TS-15 at different inoculation sites including leaf, blossom, tomato, and bed soil was observed on day 0 (3 hrs after inoculation), day 1, day 2, day 3, and day 4 post inoculation.

Effects of Different Nitrogen and Carbon Source on TS-15 Growth In Vitro.

In order to find a carbon source that supports better growth of TS-15 in minimal medium and inhibit the growth of *Salmonella* at the same time, both TS-15 and S. Newport were examined for cellular phenotypes using the Biolog Phenotypic Microarray (PM) System (Biolog, Inc., Hayward, Calif.), which allows for the simultaneous screening of approximately 1,200 phenotypes. All materials, media, and reagents for the PM system were purchased from Biolog. PM experiments were conducted using the conditions recommended by the manufacturer, except that bacteria stored at −86° C. were streaked onto TSA agar plates instead of BUG+B agar plates. The PM plates were incubated at 37° C. in an Omnilog incubator and readings were recorded every 15 min for 48 h. Bacterial respiration was assessed within each well by monitoring color formation resulting from reduction of the tetrazolium violet (dye A for S. Newport and dye F for TS-15), and color intensity was expressed in arbitrary units (AU). Kinetic data were analyzed with OmniLog-PM software from Biolog (OL_PM_Par1.20.02, Dec. 8, 2005). Substrates showing a 2-fold (≥15,000 area under curve, arbitrary units) difference between TS-15 and S. Newport strain were considered as potential carbon source for TS-15. The effects of different carbon source combinations with different minimal medium formulations on growth of TS-15 and *Salmonella* were further characterized using the Bioscreen assays described above.

Statistical Analysis.

Estimates of the rate of reduction in bacterial counts were obtained by fitting a robust linear model of the log transformed CFU onto days (day since inoculation). The slopes of the fitted lines from treated and untreated surfaces were compared to look for differences in the rates of reduction. The analysis was performed using the R statistical software package, version 2.11.1, with the robust library. The results were tallied for each combination of plant location, antagonist, plant, and day. Within each plant location, both a regression and a rank test compared the effect of using the antagonist with that of not using it. The tally of the plates divided the sum of their counts by the sum of the masses of the original sample that they received. An imputation procedure, discussed in Blodgett, R. J., 2008 Mathematical treatment of plates with colony counts outside the acceptable range. Food Microbiology 25: 92-98 accounted for the TNTC plates.

Purification and Identification of Antagonistic Compounds.

*P. alvei* TS-15 was cultured in minimal medium, and the culture was centrifuged at 4,000 rpm for 10 min. The supernatant was filter-sterilized using 0.22 um cellulose acetate filter to get the cell free culture supernatant (CFCS). CFCS was fractionated using a 10 kDa molecular weight cut-off filter (MILLPORE, Billerica, Mass.) as per manufacturer's instructions. The filtrate was diluted 1:1 using HPLC grade water. The sample was acidified with trifluoroacetic acid (TFA) (0.1% v/v final concentration) prior to HPLC analysis. Separation was performed on an Agilent 1100 series HPLC using a Kinetex C18 column (4.6×100 mm, PHENOMENEX, Torrance, Calif.) maintained at 40° C. Mobile phase A was composed of 0.1% TFA while 0.1% TFA in acetonitrile comprised mobile phase B. Briefly, 75 µl of diluted filtrate was loaded onto the column and flushed with 97% mobile phase A at a flow rate of 1 ml/min to remove salts. Separation was accomplished using a linear gradient from 97% to 20% A in 8 min at 1 ml/min. The eluate was monitored by UV-detection at 210 nm. The above method was developed and optimized using nisin and polymyxin B (SIGMA-ALDRICH, St. Louis, Mo.) as reference material.

Results:

Isolation and Identification of an Antimicrobial-Producing Strain from Tomato Soil.

A large number of environmental isolates from the tomato field were screened for antimicrobial activity against S. Newport. Two isolates, one from an epiphytic leaf surface of native Eastern Shore vegetation and the other from Eastern Shore tomato soil, showed distinct inhibition areas on basal TSA agar. These isolates formed pale colonies and swarmed vigorously on TSA. Morphologically, the isolates were rod-shaped, 0.7-0.95 cm by 3.18-3.42 cm (FIG. 1), gram-positive bacteria. Upon prolonged incubation on an agar medium, cells produced central endospores.

The isolates are positive for oxidase, nitrate reduction, gelatin liquefaction, starch hydrolyzation, casein hydrolysis, glucose fermentation, and urease but negative for catalase, indole production, and $H_2S$ formation. The bacterium grew well in TSB broth under aerobic conditions. Genomic analysis showed the 16S rRNA gene of both isolates shares over 99.0% sequence similarity with that of *Paenibacillus alvei*. VITEK biochemical analysis confirmed the high similarity of both isolates (>99%) with *P. alvei*. Thus, it was concluded that both isolates belong to *P. alvei*, and they were given strain designations of A6-6i-x and TS-15 respectively.

Antimicrobial Spectrum of *P. Alvei* A6-6i-x and TS-15 Vegetative Cells and Culture Supernatants.

In vitro agar plug assays showed inhibition zones against S. Newport and all other five major foodborne pathogens when challenged with both *P. alvei* isolates (FIG. 2). Notably, the antagonist migrated outward from the plug after forming the inhibition zone on *Shigella* or *Listeria*, and the growth ring of antagonist expanded with time especially in the case of *Listeria*. Both A6-6i-x and TS-15 had a wide range of inhibition against MRSA species (zone diameter from 15 to 25 mm) and showed strong inhibitory effects on various MRSA strains tested despite the fact that some strains were resistant to up to 14 different antimicrobial drugs. The average inhibition zones of both A6-6i-x and TS-15 at different time points are presented in FIG. 3.

Figure 4:
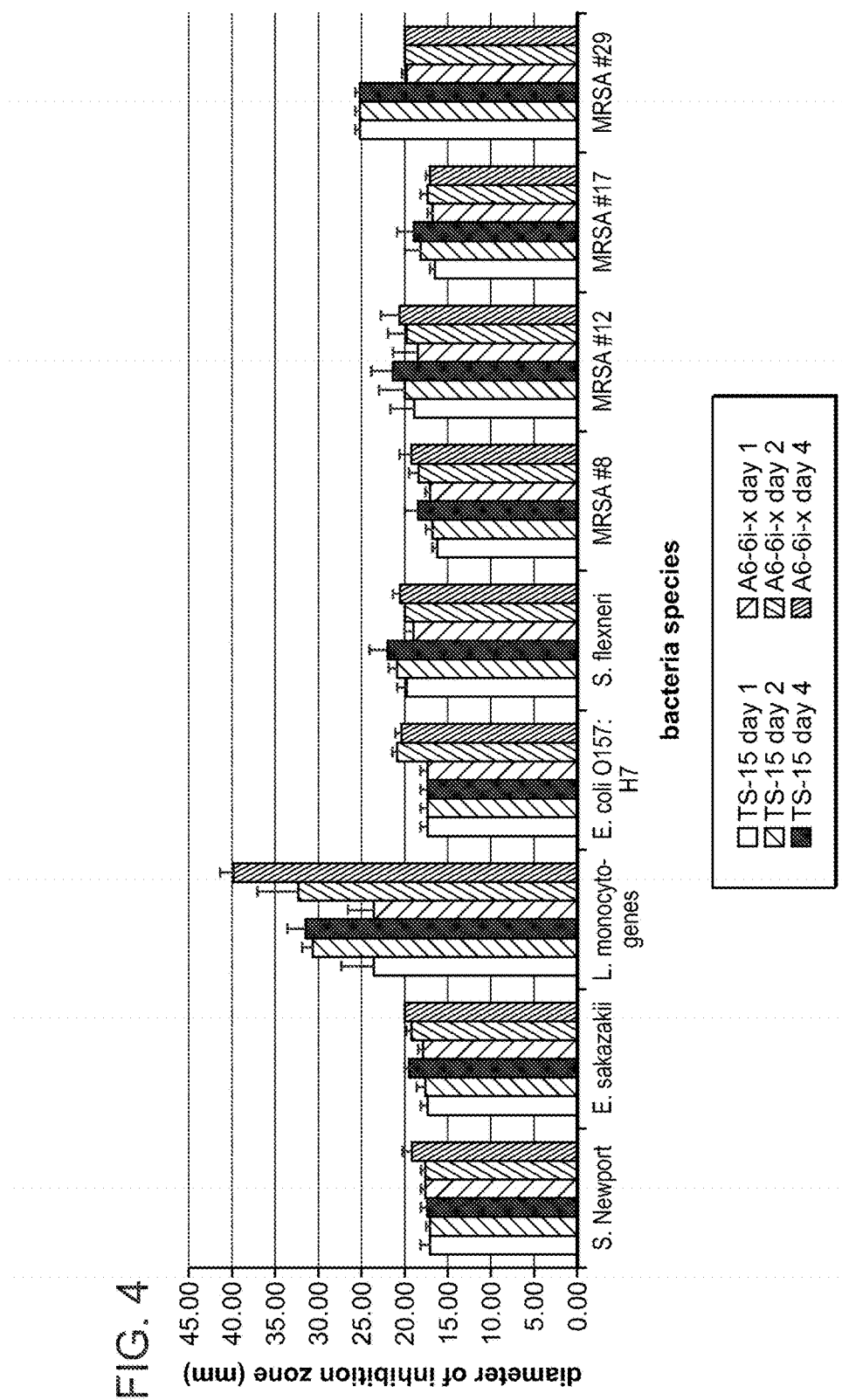
FIG. 4 is a graph that compares the diameter of inhibition zone (mm) measured at day 1, day 2 and day 4 post-inoculation using an in vitro agar plug assay for TS-15 and A6-6i-x against *Salmonella enterica* serovar Newport. *Enterobacter* sakazakii, *Listeria monocytogenes*, *E. coli* O157:H7; *Shigella flexneri*, methicillin-resistant *Staphylococcus aureus* (MRSA#8), methicillin-resistant *Staphylococcus aureus* (MRSA#12), methicillin-resistant *Staphylococcus aureus* (MRSA#17), and methicillin-resistant *Staphylococcus aureus* (MRSA#29). An in vitro agar plug assay was used to evaluate the growth inhibition. Diameter of the 'inhibition' zone was measured at day 1, day 2, and day 4. The average 'inhibition' zones of TS-15 and A6-6i-x against major foodborne pathogens indicated above was calculated (n=6). Error bars represent standard deviation.
Figure 5A:
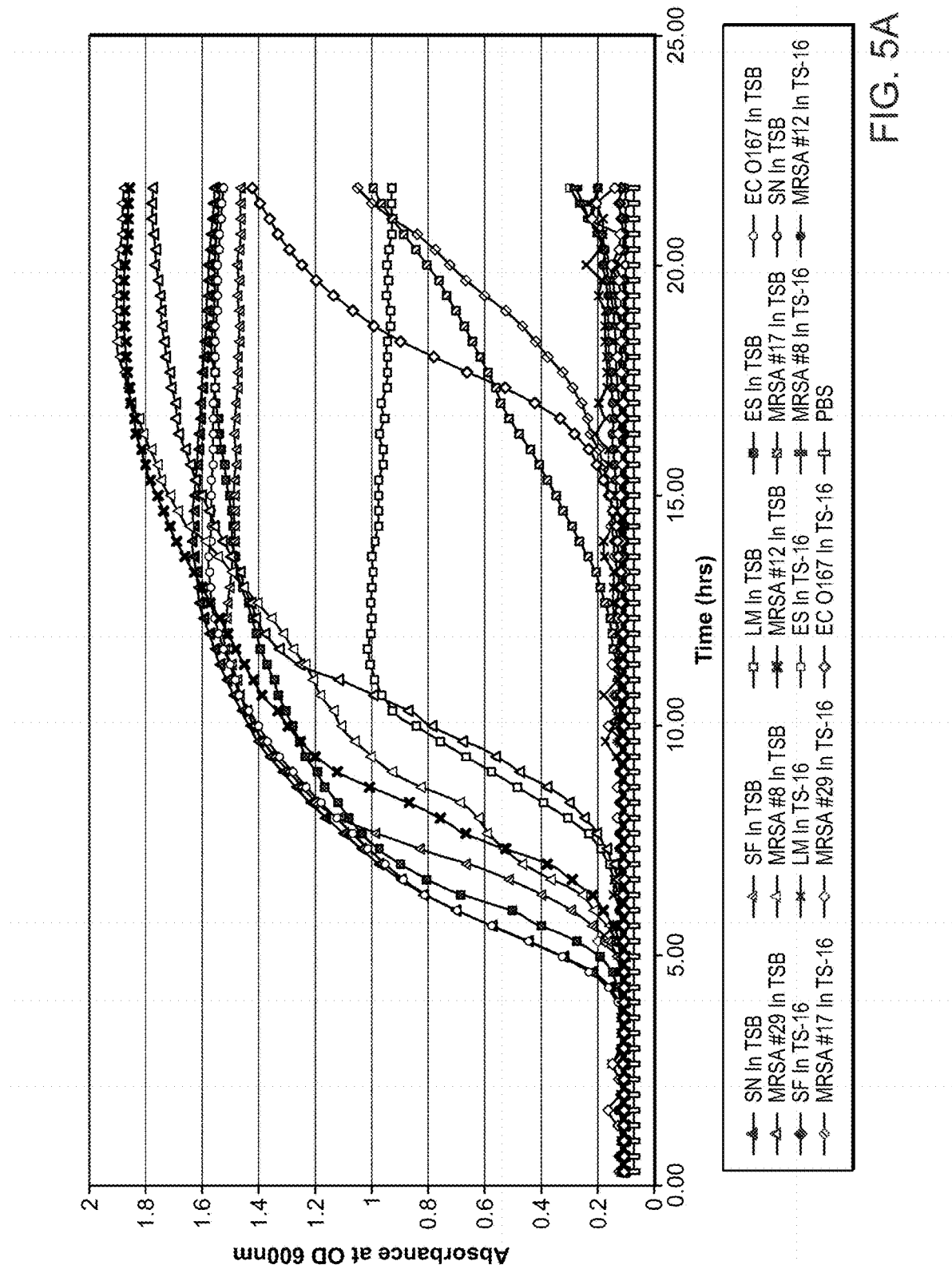
FIG. 5 is a graph depicting growth inhibition of major foodborne pathogens in *P. alvei* TS-15 and A6-6i-x cell free culture supernatants (CFCS). (A) Depicts the effects of TS-15 on the growth of *E. coli* O157:H7, *E. sakazakii*, S. Newport, *S. flexneri*, *L. monocytogenes*, and MRSA strains in trypticase soy broth (TSB). Growth was measured by determining increases in cell density ($OD_{600}$) at 20 min intervals using a Bioscreen instrument. Data shown is representative of two experiments. (B) Depicts the effects of A6-6i-x on the growth of *E. coli* O157:H7, *E. sakazakii*, S. Newport, *S. flexneri*, *L. monocytogenes*, and MRSA strains in trypticase soy broth (TSB). Growth was measured by determining increases in cell density ($OD_{600}$) at 20 min intervals using a Bioscreen instrument. Data shown is representative of two experiments. See legend for the identity of the strains tested.
Figure 5B:
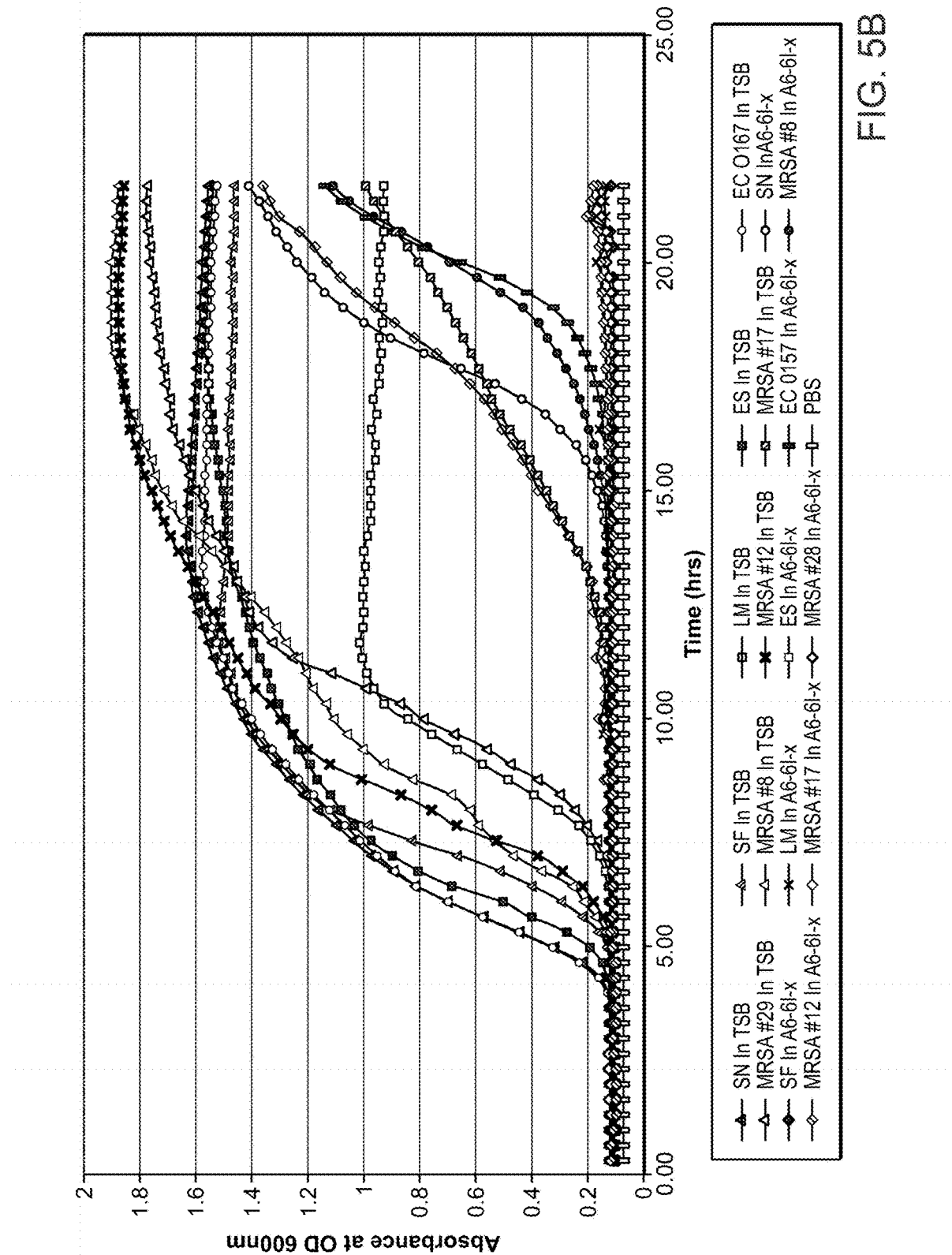

When tested against the panel of gram-negative and gram-positive bacteria using the Bioscreen assay, both A6-6i-x and TS-15 cell-free culture supernatant (CFCS) exhibited a broad spectrum of antimicrobial activity, in which the lag phase was significantly extended in all the pathogens tested (FIG. 4). Furthermore, the lag phase in ES (*E. sakazakii*), SF (*S. flexneri*), LM (*L. monocytogenes*), and some MRSA strains were extended to almost 24 h in both A6-6i-x and TS-15 CFCS. Additionally, CFCS from TS-15 had much stronger inhibitory effect than A6-6i-x CFCS when tested against SN (S. Newport).

Efficacy of *P. Alvei* A6-6i-x and TS-15 on Tomato Fruit in Humidity Chambers.

S. Newport showed significant reduction on tomato surface by both *P. alvei* A6-6i-x and TS-15. However, comparing an average of ½ log reduction by A6-6i-x, TS-15 had a 5 log reduction on S. Newport population which were applied on tomato fruit (FIG. 6). Recovered S. Newport from tomato surfaces was 100 times less on average when the antagonist was added prior to *Salmonella* on the tomato surface. Nevertheless, no significant difference was found in the reduction rate regardless of whether or not the antagonist was inoculated first or after SN inoculation.

Field Trials in High Tunnel Using *P. Alvei* TS-15.

Figure 7A:
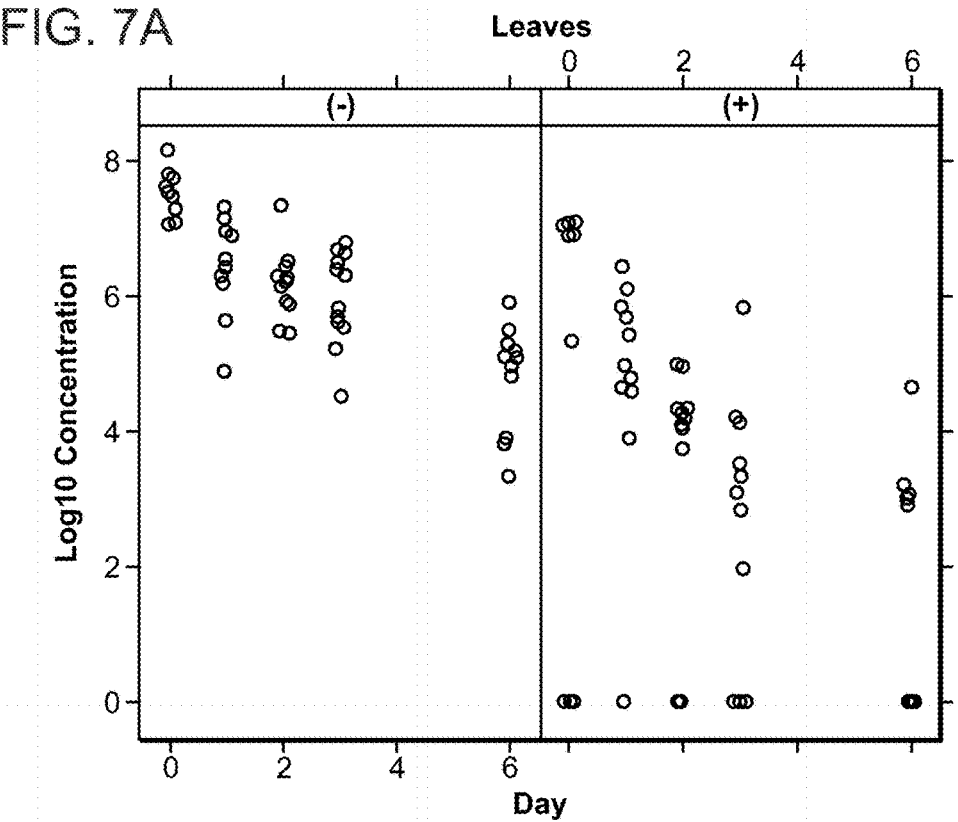
FIG. 7 is a set of scatter plots that depict the recovery of an S. Newport attenuated strain from tomato plants, including blossoms, leaves, and tomato fruits. In the high tunnel study, S. Newport was recovered from leaves, blossoms and tomatoes after inoculation for 0, 1, 2, 3, and 5 (for blossom) or 6 (for leaves and tomatoes) days with S. Newport only or S. Newport and an antagonistic co-inoculation with TS-15. The results were tallied for each combination of plant location, antagonist, plant, and day. Estimated recovery of S. Newport on each sample point from log transformed data in control (+) and antagonist treatment (+) panel was scatter plotted for leaves (A), blossom (B), and tomato (C).
FIG. 7D provides a graph summarizing the results of FIGS. 7A-7C.
Figure 7B:
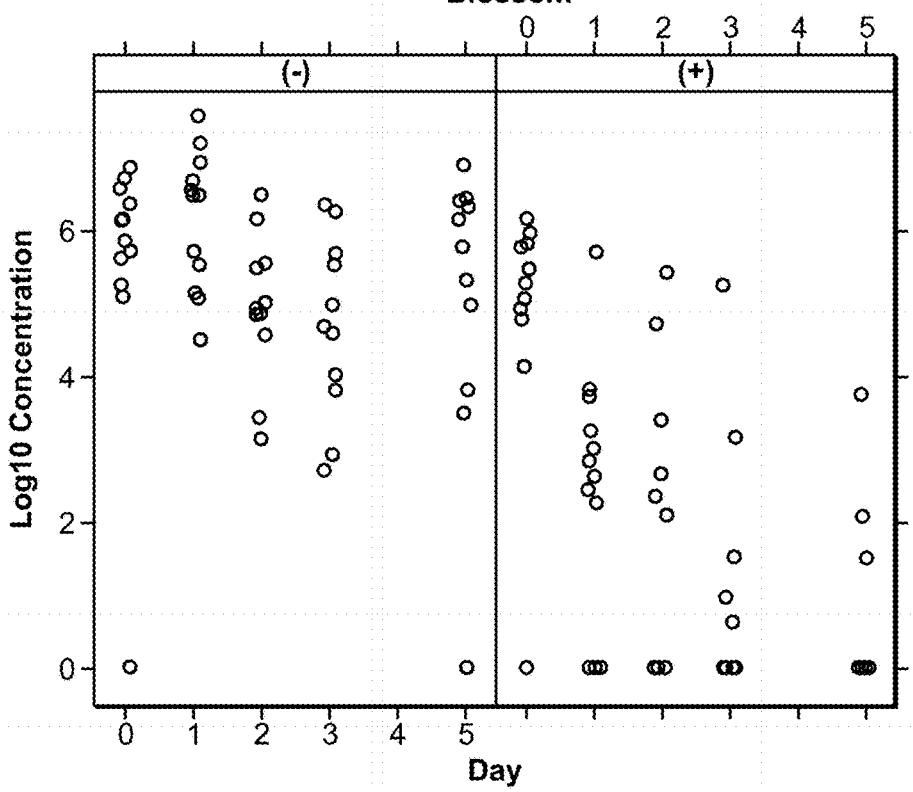
Figure 8:
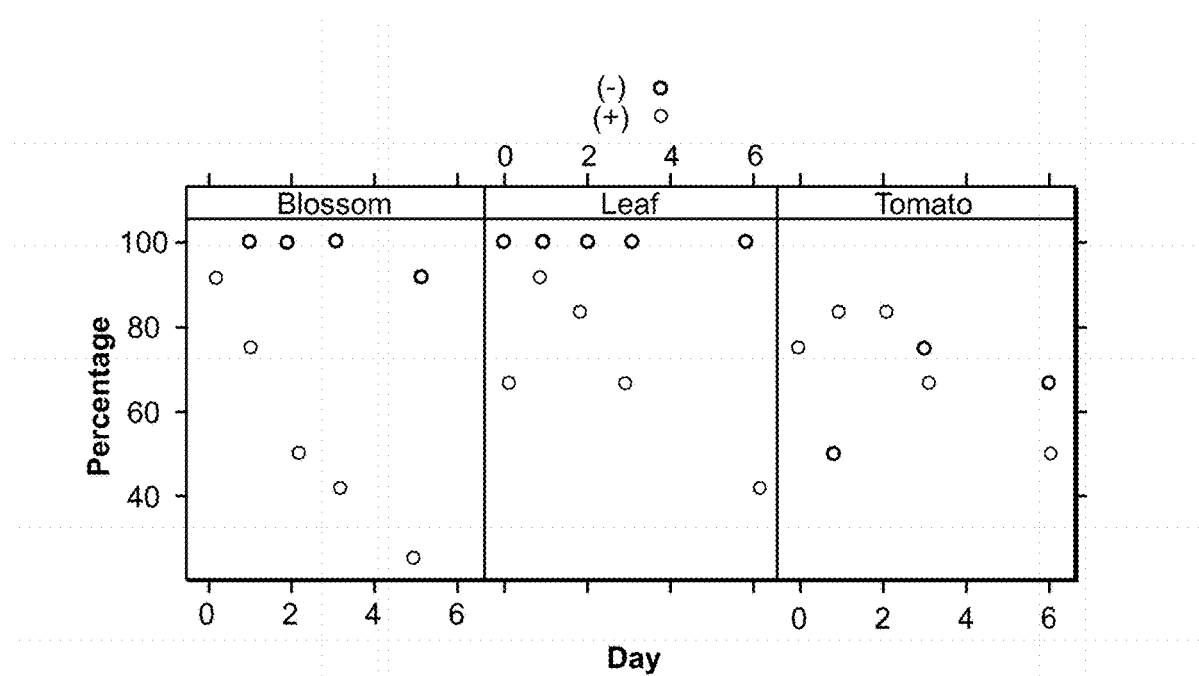
FIG. 8 is a scatter plot showing plants with detectable levels of *Salmonella* post inoculation. In high tunnel setting, leaves, blossoms and tomatoes were harvested at day 0, day 1, day 2, day 3, and day 5 (for blossoms) or day 6 (for leaves and tomatoes) post inoculation for recovering any remaining S. Newport. The percentage of plants that had detectable level of S. Newport in control (blue circle) and antagonist treatment (purple circle) groups was calculated and plotted for every time point post inoculation.

During field trials (spanning 3 months) the maximum daily temperature and RH varied, respectively, between 26.7 and 37.8° C. and between 56% and 80%. At Day 0, variations were detected between the group without TS-15 and the group with TS-15 on leaf and blossom but not on tomato in terms of *Salmonella* population after inoculation. Taking all the variations into effect, the concentration of *Salmonella* was significantly lower ($p \leq 0.05$) on plants with TS-15 on leaves, blossoms, and tomatoes from day 1 to day 5 (for blossom) or day 6 (for leaf and tomato) (FIG. 7). Notably, close to 100% of the '*Salmonella* only' plants still had detectable levels of *Salmonella* at the end of the blossom and leaf trials, whereas only 2 plants (<20%) had detectable levels of *Salmonella* in the 'antagonist group' in the blossom trial and 6 plants (~50%) in the leaf trial (FIG. 8). Moreover, the rate of decrease in bacterial concentration was significantly higher ($p \leq 0.05$) on leaves and blossoms with TS-15 versus those without TS-15, 12 fold decreases per day versus 2.7 fold per day for leaves, and 8.9 fold versus 1.4 fold for blossoms, respectively. However, no statistically significant difference was found in the mortality rate of *Salmonella* on tomato fruits in this study. Albeit, upon inspection (FIG. 7C), *Salmonella* counts were substantially lower on TS-15 treated tomato fruits than on untreated fruits.

Persistence of *P. alvei* TS-15 on Tomato Plants in the Field.

Figure 9:
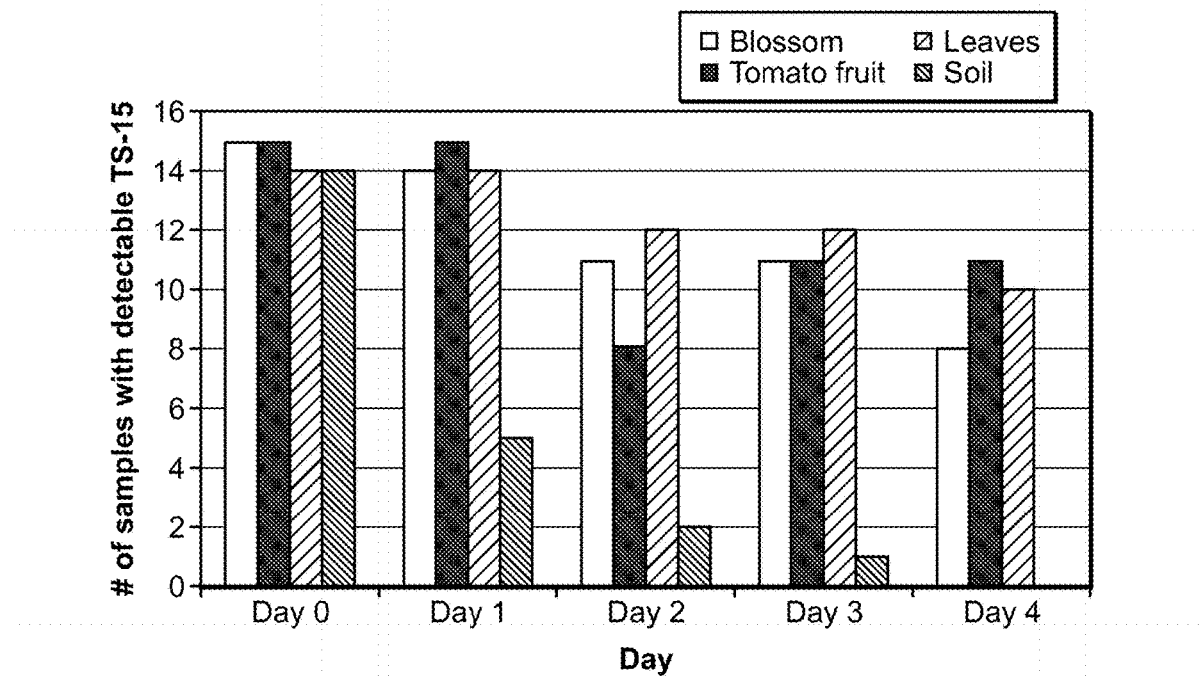
FIG. 9 provides a graph that shows persistence of *P. alvei* TS-15 on tomato plants. A spray inoculation method was used to inoculate tomato plant including leaves, blossoms, and tomatoes, and soil from planting beds in a tomato field located in Accomack, Va. The survival of TS-15 at different inoculation sites was observed on day 0 (3 hours after inoculation), day 1, day 2, day 3, and day 4 post-inoculation. The number of samples with detectable TS-15 was counted.

In the week of field trials from there was 0.1 inches of precipitation everyday on the first three days of the experiment. At the end of the trial, *P. alvei* TS-15 persisted well through the whole experiment (4 days) on leaf, blossoms, and tomatoes on more than 50% (8 out of 15) of the plants. In soil, TS-15 persisted for a much shorter time. 50% of the soil samples already had no detection of *P. alvei* TS-15 after 24 h, and TS-15 was found persisting in only 2 soil samples out of 15 samples after 2 days (FIG. 9). It is important to note that no *P. alvei* TS-15 was found in control sample plants that were not inoculated with the antagonist, pointing to recovery of an introduced strain, solely.

Growth of *P. Alvei* TS-15 in Minimal Medium Using D-Glucose as Sole Carbon Source and Yeast as Sole Nitrogen Source.

Figure 10A:
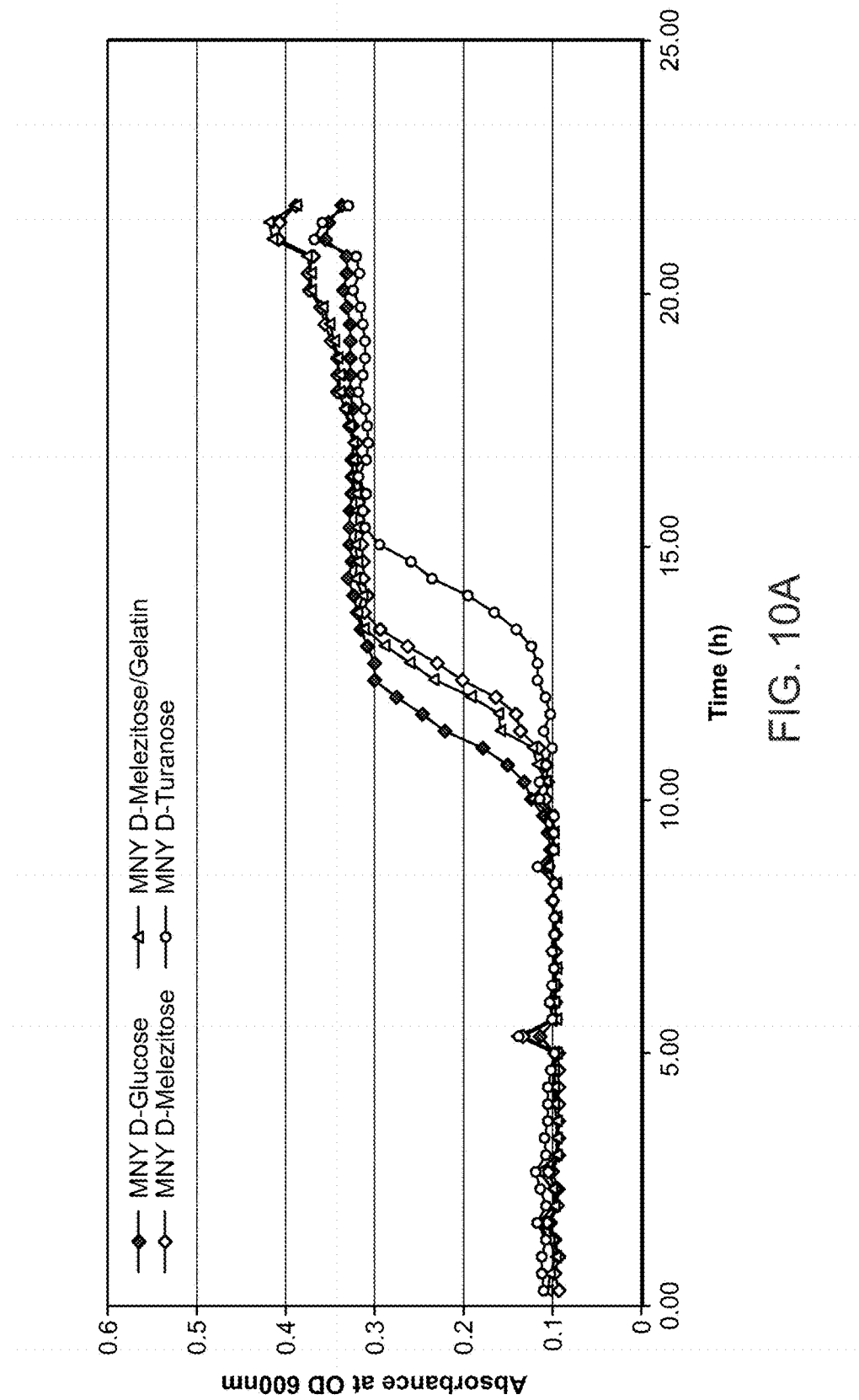
FIG. 10 depicts the growth of P. alvei TS-15 in minimal medium (MN) with different carbon sources. Using yeast as the sole nitrogen source, P. alvei TS-15 was grown in MN with D-glucose (DG), D-melezitose (DM), D-turanose (DT), and DM-gelatin combination, respectively. Growth of P. alvei TS-15 (A) and its inhibitory effect against S. Newport (B) were measured by determining the increase in cell density ($OD_{600}$) at 20 min intervals using a Bioscreen instrument. Data shown is representative of two experiments.
Figure 10B:
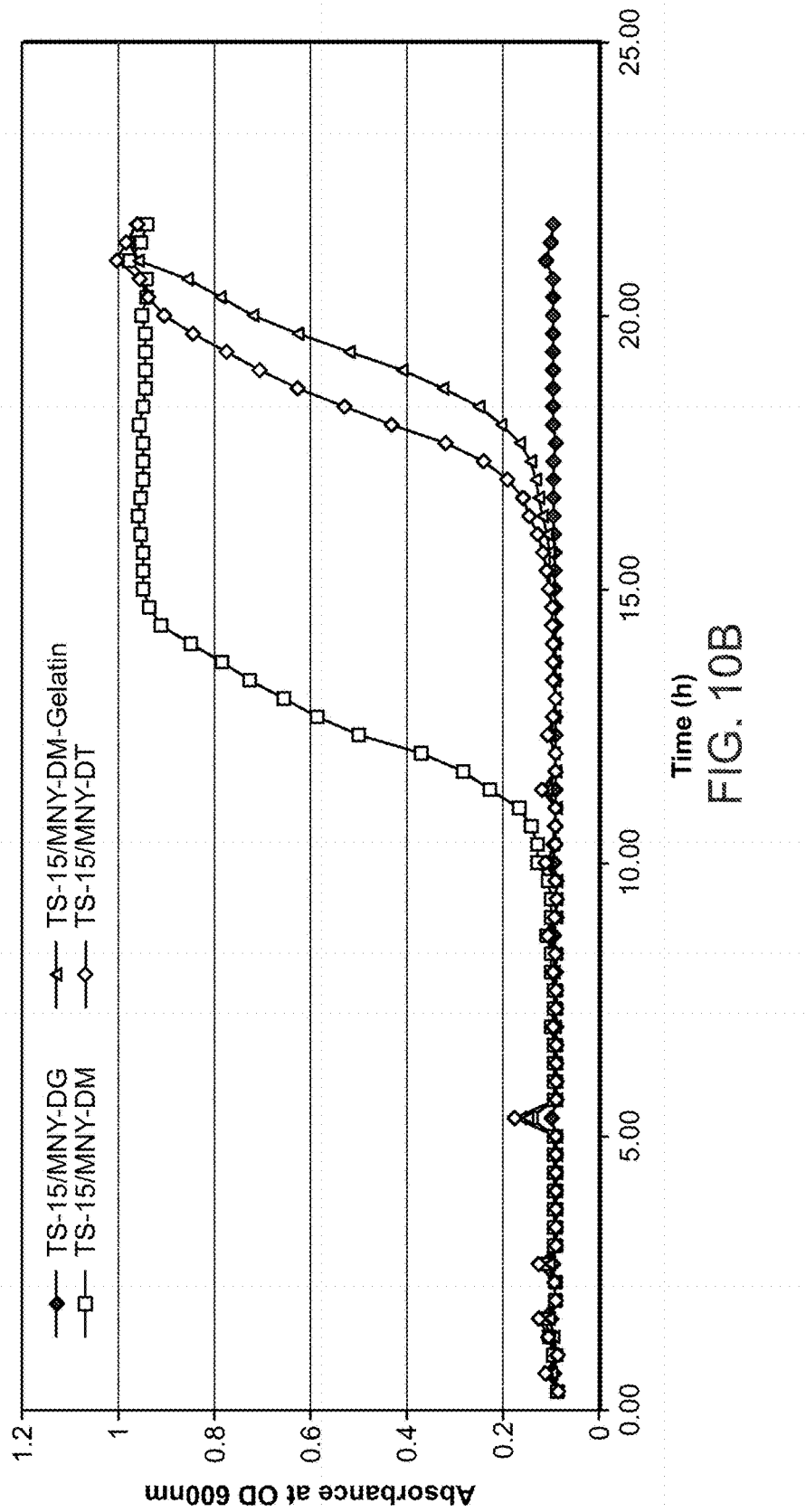
Figure 11:
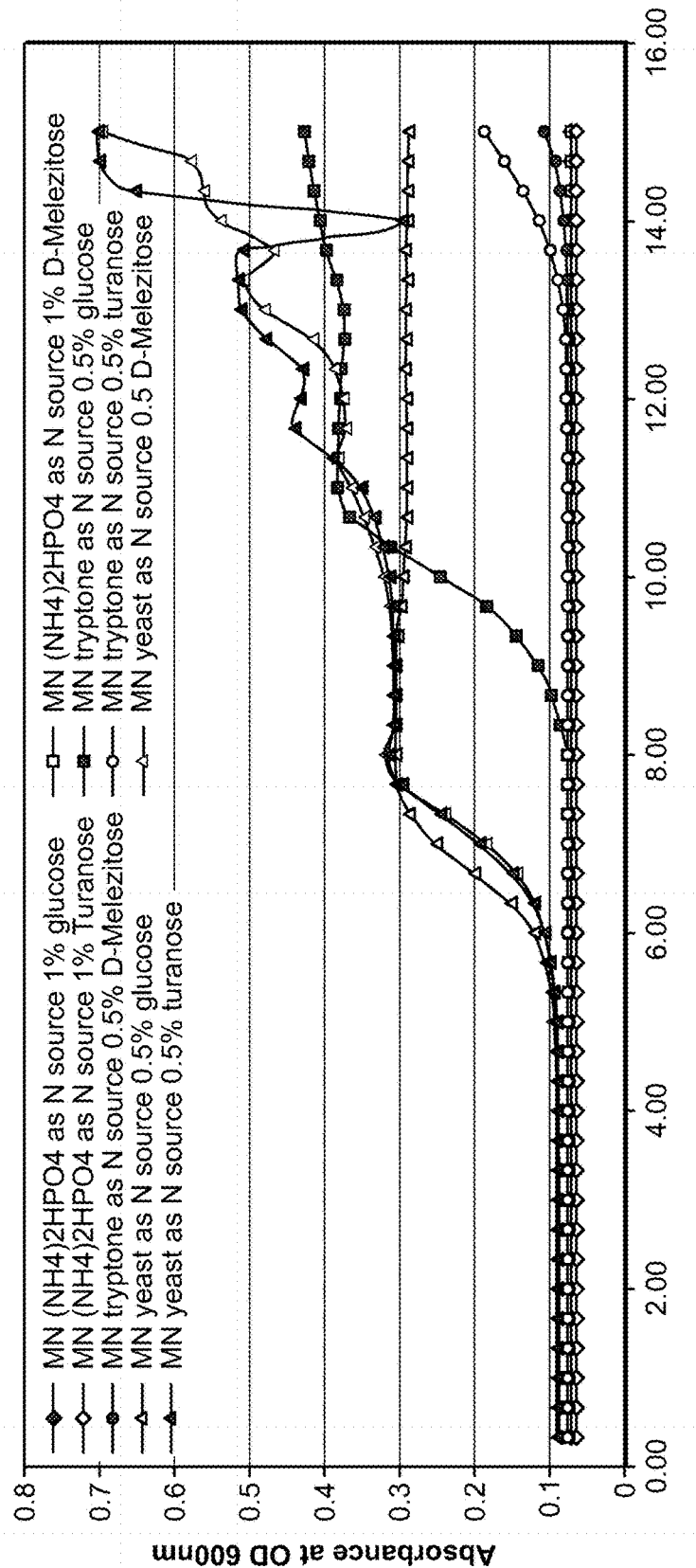
FIG. 11 depicts the growth of P. alvei TS-15 in minimal medium with different nitrogen sources. P. alvei TS-15 was grown in MN with combination of selected nitrogen sources (($NH_4)_2HPO_4$, tryptone, and yeast) and carbon sources (D-glucose, D-melezitose, and D-turanose). Growth of TS-15 was measured by determining the increase in cell density ($OD_{600}$) at 20 min intervals using a Bioscreen instrument. Data shown is representative of two experiments.
Figure 12:
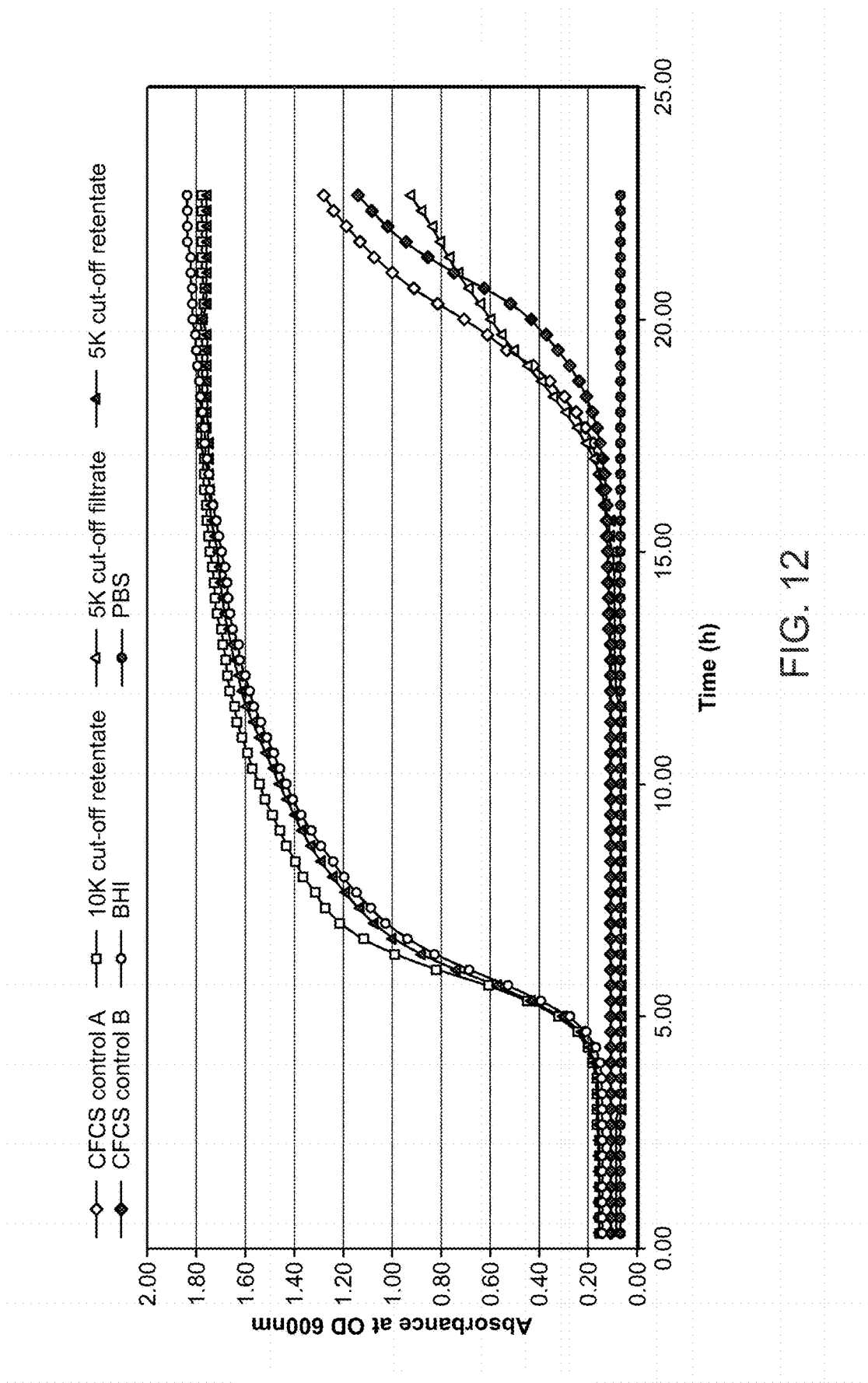
FIG. 12 characterizes growth of S. Newport in cell free culture supernatant (CFCS). Growth of S. Newport in 10 kDa and 5 kDa MWCO filtrates and retentates, respectively, was measured by determining the increase in cell density ($OD_{600}$) at 20 min intervals using a Bioscreen instrument. Data shown is representative of two experiments.
Figure 13:
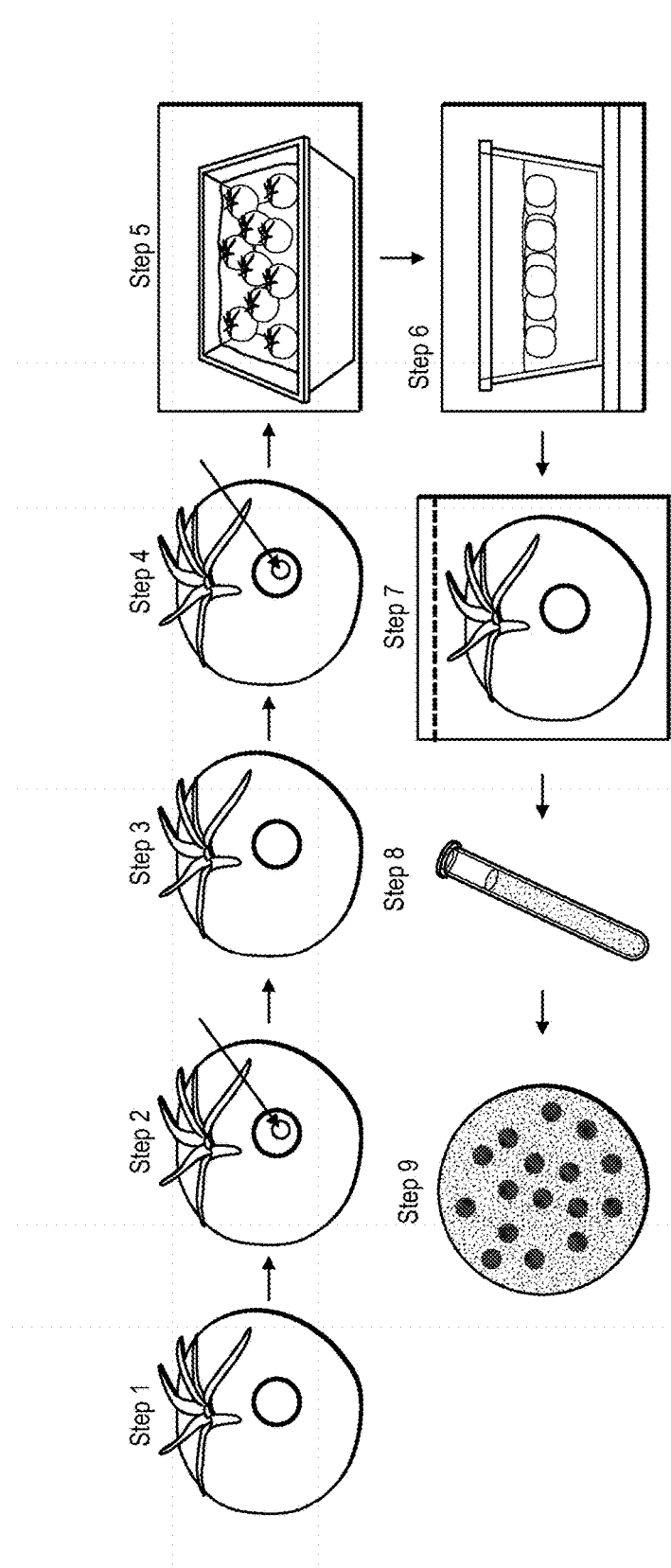
FIG. 13 is a diagram depicting a step by step method for inoculating and processing tomatoes to test the effectiveness of the Paenibacillus of the invention against foodborne pathogens. Step 1: Circles are drawn on tomatoes with a permanent marker that has been washed with water and then sterilized with alcohol. Step 2: 20 µl of a 107 cfu/ml overnight grown S. Newport suspended in PBS is pipetted into the circle. Step 3: The S. Newport is allowed to dry. Step 4: 40 µl of the antagonist re-suspended in fresh TSB is placed on top of the S. Newport spot. Step 5: Tomatoes are allowed to dry in humidity chamber. Step 6: 1.5 L of water is added to the bottom of the chamber and the lid is closed. The box is incubated at 30° C. overnight. Step 7: Tomatoes are taken out and placed in a sealable bag (e.g., ZIPLOCK). 30 µl of PBS is then added and the circled area is agitated for 1 min. Step 8: The 30 ml wash is pipetted into a 50 ml conical tube and then dilutions are made (0, 1 and 3). Step 9: The suspensions and dilutions are plated on fresh XLD plates and the black positive colonies are counted.
Figure 14:
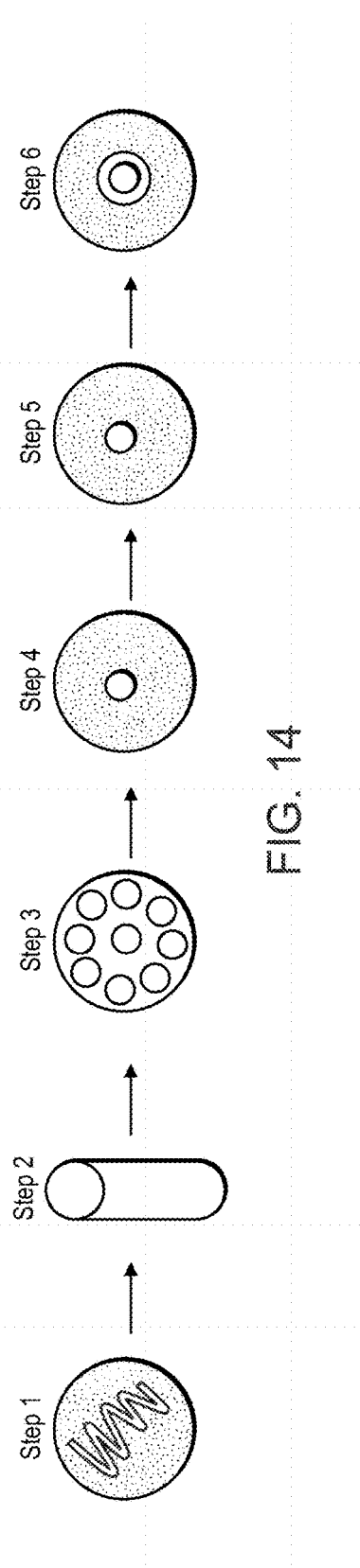
FIG. 14 is a diagram showing a step by step procedure for making agar plugs for the agar plug method described herein, e.g., in Example 1. Step 1: An overnight plate of the antagonist of choice (e.g., Paenibacillus TS-15) was mixed with 4 ml of distilled $H_2O$. Step 2: The suspension was mixed with 20 ml of molten TSA agar. Step 3: The agar was then poured into a petri dish, allowed to dry, incubated overnight, and the plugs were stamped out of the overnight plate. Step 4: The plugs were put on a TSA plate which was spread with a $10^6$ cfu/ml suspension of the S. Newport. Step 5: The plate was allowed to incubate for 1, 3, and 4 days. Step 6: The zones of inhibition and death were then measured with a ruler in mm each day.
Figure 15A:
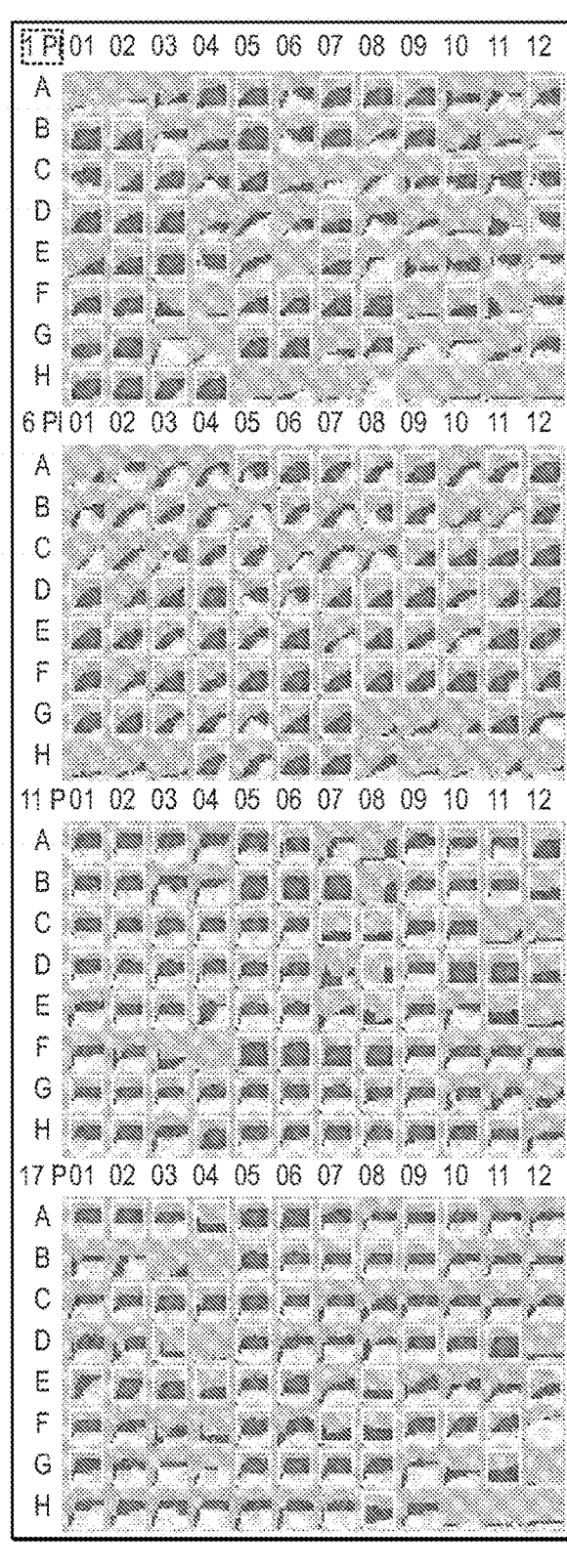
Figure 15B:
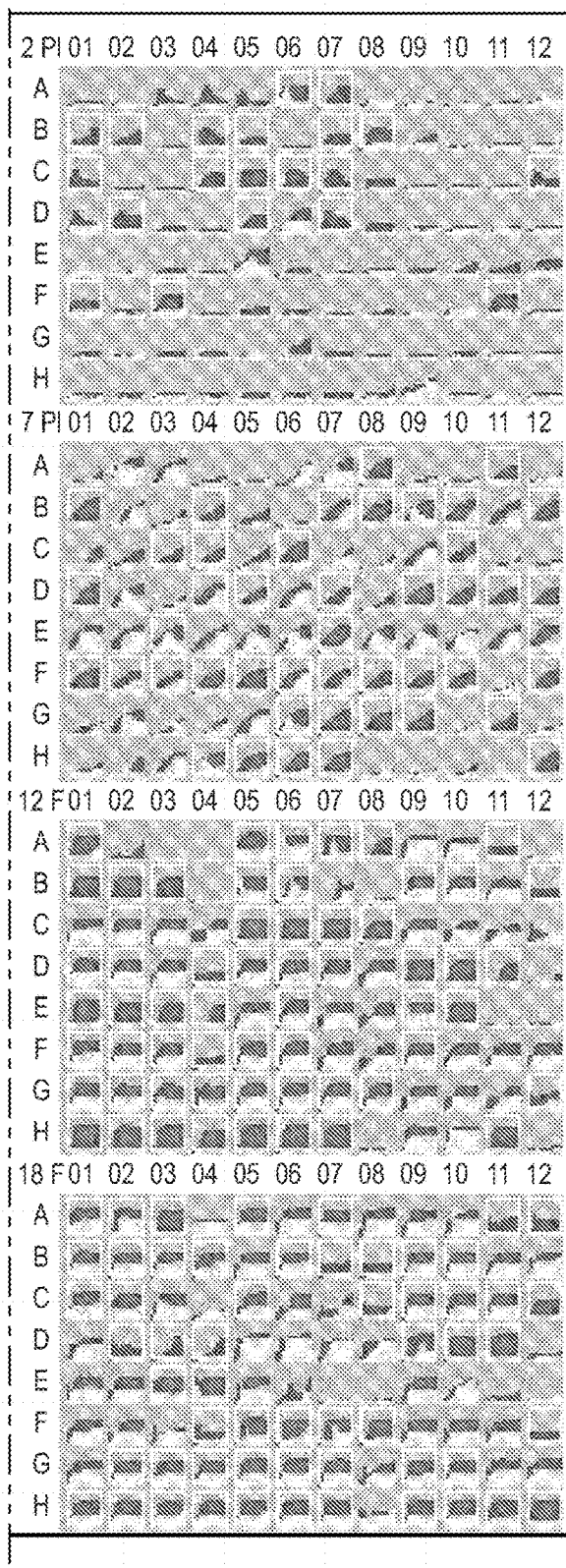
Figure 15C:
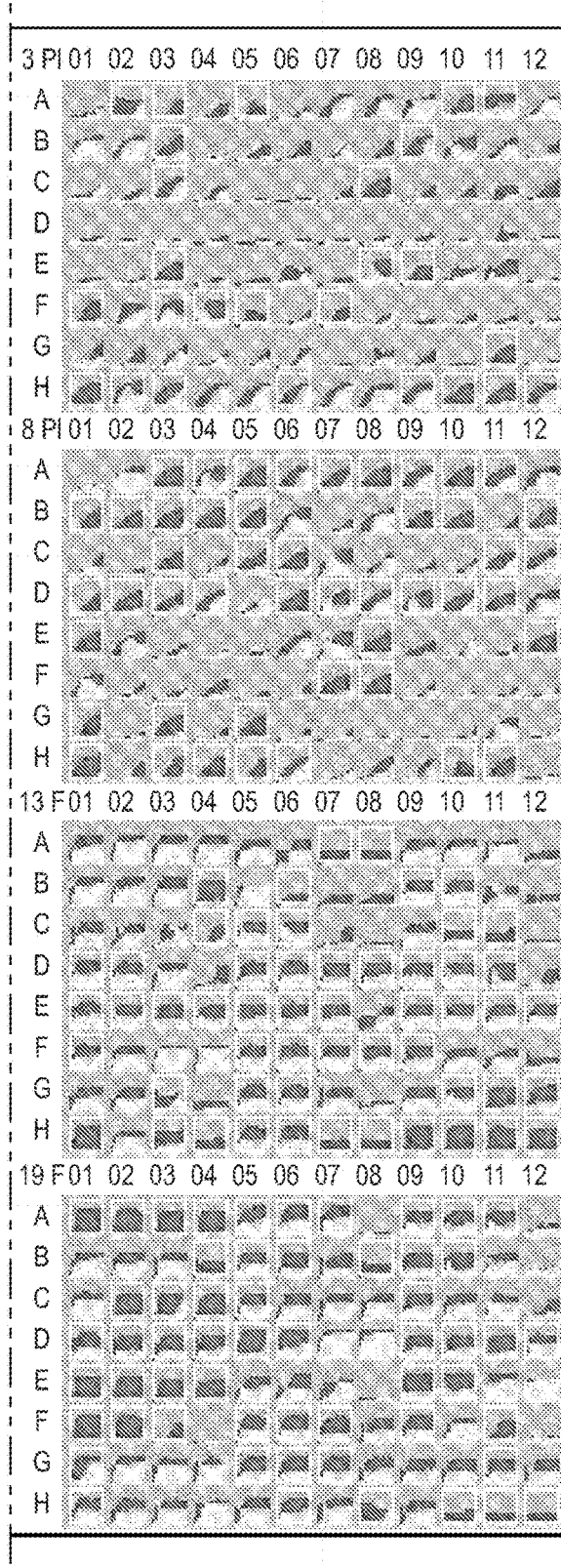
Figure 15D:
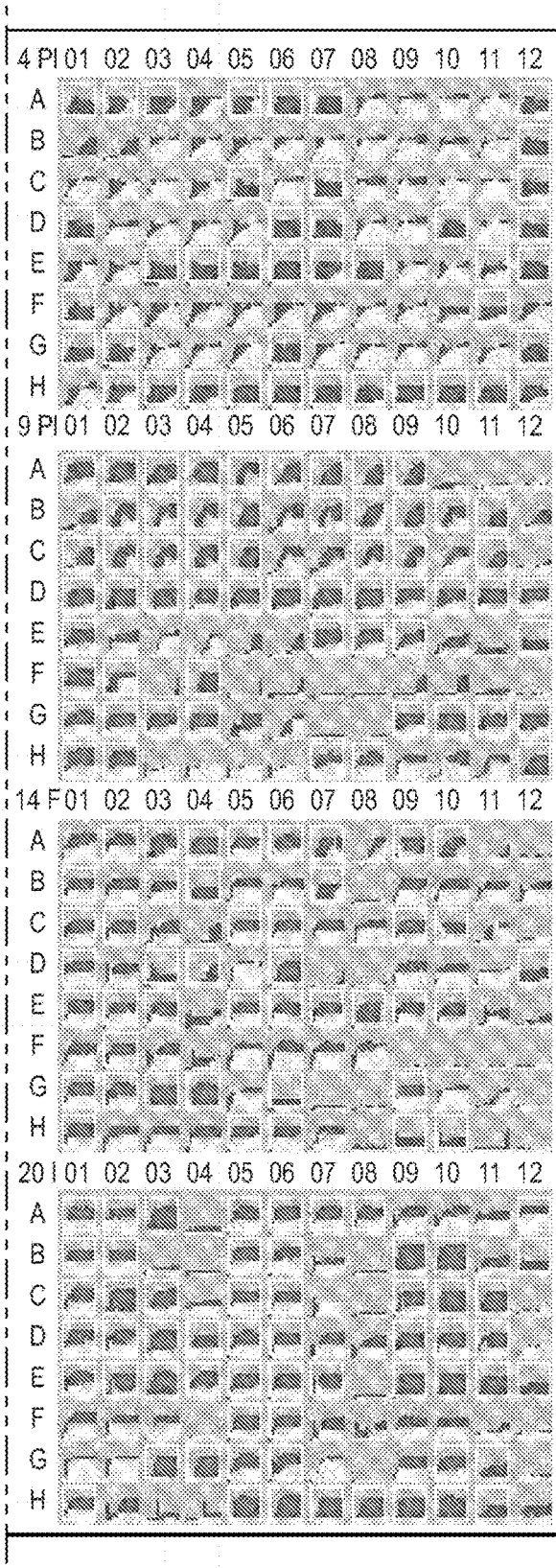

The impact of different nitrogen sources and carbon sources on the growth of *P. alvei* TS-15 and on the maximum inhibitory effect of *P. alvei* TS-15 against S. Newport in the minimum medium was shown in FIGS. 10 and 11. The best growth of TS-15 was in the minimal medium with glucose and D-Melezitose (with or without gelatin), while the least growth of TS-15 was observed in minimal medium with turanose (FIG. 10A). Furthermore, glucose, as the sole carbon source, conferred upon TS-15 the maximum inhibitory response against S. Newport (FIG. 11). In addition, yeast is the nitrogen source that supported optimal growth of TS-15 in minimal medium (FIG. 10B).

Characterization of Cell Free Culture Supernatant (CFCS).

The filtrate and retentate after 10 kDa molecular weight cut off (MWCO) filtration, and the filtrate and retentate after another 5 kDa MWCO filtration were subjected to bioscreen assays for activity. The results from the bioscreen assay showed that CFCS controls A and B extended the lag phase of S. Newport growth. Similarly, the 10 kDa and 5 kDa MWCO filtrate inhibits the growth of *Salmonella* to roughly the same extent. In contrast, the retentate from both the 10 kDa and 5 kDa MWCO displayed no inhibition of *Salmonella* growth as control supernatant (BHI). This indicates that the components responsible for *Salmonella* growth inhibition partition to the 5 kDa MWCO filtered CFCS.

Conclusions:

The two antagonistic bacteria found in the field showed significant inhibitory properties against S. Newport. The data shows that the antagonistic bacteria produce inhibitory compounds that are effective against *Salmonella*.

Figure 3B:
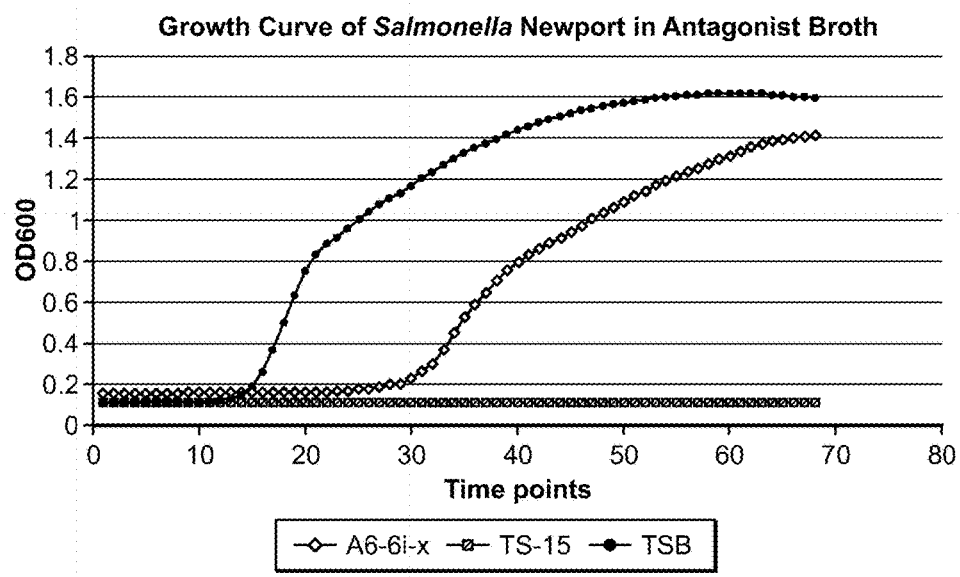

The Bioscreen test showed that TS-15 was significantly more effective in reducing the amount of *Salmonella* in the broth screening assay (FIG. 3B). A flat line effect for the TS-15 strain was observed while the A6-6i-x strain produced a gross shift to the right of the growth curve. The A6-6i-x was still effective but it did not produce as great of a change as its counterpart. It is possible that the TS-15 is producing a greater amount of the same compounds which may be why its is flat lining the growth curve. The other possibility is that the compounds being produced by TS-15 are more powerful than those produced by A6-6i-x. The compounds are currently being analyzed for there make up and properties.

The competiveness on TSA plates of both strains against S. Newport was tested in the plug assay which showed that the A6-6i-x was able to produce larger zones of inhibition and growth than TS-15. These results imply that the A6-6i-x strain is a faster grower than the TS-15. However there may be a trade off between how fast the microbe can grow vs. its antagonistic peptide output.

Figure 6A:
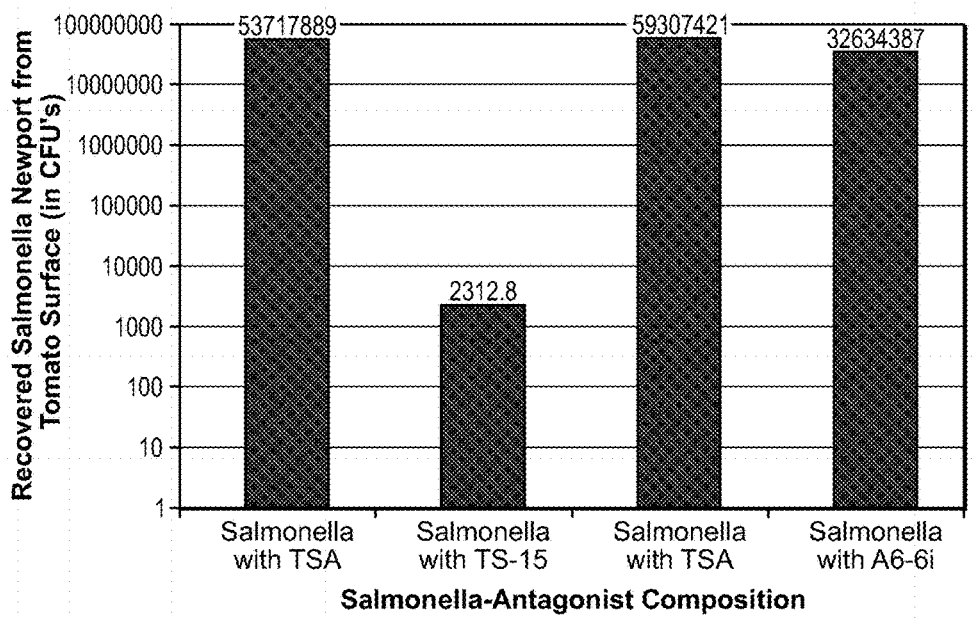
FIG. 6 shows graphs that depict the recovery of S. Newport from intact tomato fruit surfaces following treatment with antagonistic inoculations of TS-15 or A6-6i-x. In (A), the S. Newport was inoculated prior to the inoculation with the TS-15 or A6-6i-x. In (B), the TS-15 or A6-6i-x was inoculated prior to inoculation with the S. Newport. The data reflects the average of two experiments.
Figure 6B:
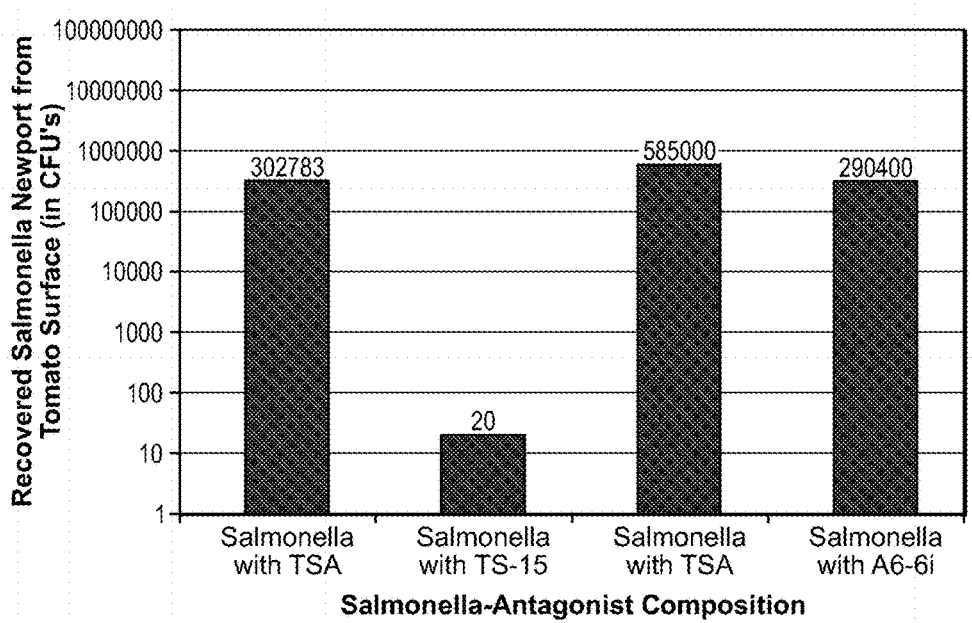

The tomato data suggests that TS-15 is more effective at removing *Salmonella* from the surface of the tomato as well as preventing it from attaching to the surface as compared to the A6-6i-x strain. TS-15 showed an average of 105 log reduction of viable S. Newport on the surface of a tomato when the S. Newport was put on first (FIG. 6A). This number includes many points in which there was a complete removal of all S. Newport. The A6-6i-x showed an average of ½ log reduction when applied to tomato that had S. Newport on it (FIG. 6B). When the antagonist was applied before the S. Newport the TS-15 showed a 105 log reduction while the A6-6i-x showed a ½log reduction. This suggests that the TS-15 strain is the superior antagonistic strain between the two.

In addition, the data show that TS-15, when mixed with formulated C and N sources (i.e., glucose and yeast extract, respectively), can have an enhanced effect on the growth of TS-15, as well as boosting the inhibitory effects on *Salmonella*. In particular, glucose as the sole carbon source conferred upon TS-15 the maximum inhibitory response against S. Newport.

Example 2. Mechanism of Internalization of *Salmonella* Spp. into Tomato Plants

The consumption of fresh tomatoes has been linked to numerous foodborne outbreaks involving various serovars of *Salmonella enterica*. Recent advances in the understanding of microbial-plant interactions have shown that human enteric pathogenic bacteria, including *S. enterica*, are adapted to survive in the plant environment. In this study, tomato plants (cv. Micro-Tom) grown in VES sandy loam soil were inoculated with *S. enterica* serovars to evaluate plausible internalization routes and to determine if there is any niche fitness for certain serovars.

The findings from this study demonstrate that both infested soil and contaminated blossoms can lead to internal fruit contamination of *Salmonella* with low levels. *Salmonella* serovars have developed adaptation in tomato cultivation not only in soil, but also on different parts of the tomato plant. Of the five serovars inoculated, serovars Newport and Javiana were dominant in sandy loam soil; Montevideo and Newport showed great adaptation on leaf and blossom. It was also found that serovar *Typhimurium* survived poorly in all the plant parts examined here, indicating a possible route for *S. Typhimurium* tomato contamination post-harvest. On the other hand, serovar Newport was the most adapted serovar in soil *rhizosphere* and on the tomato plant in general. Plants right after transplanting (within 3 days) had an increased internalization rate indicating that plants right after transplantation were more susceptible to internalization. These results demonstrate that *Salmonella* serovar and plant stage were two important factors for internalization through the root system, which may explain why S. Newport is repeatedly associated with foodborne illness outbreaks linked to tomatoes from VES.

Introduction

Non-typhoidal *salmonella* spp. are some of the leading causes of hospitalization due to foodborne illnesses in the United States (Scallan, E. et al. Emerg Infect Dis 2011 17: 7-15). The incidence of *Salmonella* infection has not declined significantly in more than a decade ((2011) Vital signs: incidence and trends of infection with pathogens transmitted commonly through food—foodborne diseases active surveillance network, 10 U.S. sites, 1996-2010. MMWR Morb Mortal Wkly Rep 60: 749-755). On the other hand, fruits and vine-stalk vegetables are increasingly implicated as vehicles of *Salmonella* spp. in foodborne outbreaks ((2011) Surveillance for foodborne disease outbreaks—United States, 2008. MMWR Morb Mortal Wkly Rep 60: 1197-1202). In particular, the consumption of fresh tomatoes has been linked to numerous foodborne outbreaks involving various serovars of *Salmonella enterica*.

Contamination of produce may occur preharvest during field production or postharvest in the processing plant. At the preharvest stage, several potential routes for *S. enterica* colonization and internalization to contaminate tomato fruits have been examined previously. These findings point to irrigation with contaminated water is a potential source of fruit contamination. However, evidence that *S. enterica* serovars are able to enter tomato plant systems through contaminated irrigation water remains inconsistent. Hintz et al. (Hintz, L. D. et al. HortScience 2010 45: 675-678) reported application of S. Newport in the root zone via repeated irrigation water can result in contamination of various tomato plant tissues (cv. Solar Fire) when sampled throughout differing plant growth stages. Yet Jablasone et al. (Jablasone, J. et al., Journal of the Science of Food and Agriculture 2004 84: 287-289) found no S. Enteritidis was recovered from plant tissue after applying contaminated water directly onto the soil of pots containing 'Cherry Gold' tomatoes. In addition, no evidence of S. Montevideo survival was found in the stems, leaves, or fruit of the tomato plant (cv. Trust) (Miles, J. M. et al. J Food Prot 2009 72: 849-852). Tomato blossom represents another potential route for *Salmonella* contamination. When 'Better Boy' tomato flowers were brushed with a five-strain cocktail of *S. enterica* (serovars Enteritidis, Hartford, Mich., Montevideo, and Poona), 25% of the ripened fruit was found to be by at least one of the five serovars contaminated (Guo, X. et al. Appl Environ Microbiol 2001 67: 4760-4764). Most recently, Barak et al (Barak, J. D. et al. Appl Environ Microbiol 2011 77: 498-504) demonstrated that phyllosphere populations of *S. enterica* resulted in tomato fruit contamination in cultivar Micro-Tom. Evidence was also presented by Gu et al. (Gu G. et al. PLoS One 2011 6: e27340) that *S. Typhimurium* can be internalized into tomato plants via leaves with the surfactant Silwet L-77 and colonize fruits at high levels without inducing any symptoms of tomato plant (cv. Florida lanai).

Survival of bacterial populations in the plant environment is often directly associated with both plant and microbe factors. Among tomato cultivars, varied contamination rates of *S. enterica* have been observed. Barak et al. hypothesized a role for the tomato cultivar in *Salmonella*-tomato interaction and found *S. enterica* population levels on tomato leaves to be cultivar dependent. In the same study, type 1 trichomes were identified as the preferred tomato leaf colonization site. However, the ability of *S. enterica* to colonize and survive on tomato plant is not likely only cultivar-dependent, but may also be *Salmonella* serovar-specific. That is, certain serovar(s) of *S. enterica* may be more adapted to survive in the tomato plant micro-environment than others. In this Example, tomato plants (cv. Micro-Tom) were inoculated with *S. enterica* serotypes to evaluate plausible internalization routes and to ascertain relative levels of fitness among several serovars most often associated with the tomato plant niche.

Materials and Methods:

Bacterial Cultures.

Five *Salmonella enterica* serotypes were obtained from the stock culture collection of the Division of Microbiology, Center for Food Safety and Nutrition, U.S. Food and Drug Administration, College Park, Md.: S. Newport (serogroup C2), S. Saintpaul (serogroup B), S. Javiana (serogroup D), S. Montevideo (serogroup C1), and *S. Typhimurium* (serogroup B). These strains were all isolated from tomato or produce associated outbreaks.

Inoculum Preparation.

Stock cultures were stored in brain heart infusion (BHI) broth containing 25% glycerol at $-80°$ C. Cultures were streaked onto tryptic soy agar (TSA) plates and incubated at $35°$ C. for 18 h. Subsequently, a single colony was transferred to 5 ml tryptic soy broth (TSB) at $35°$ C. for 18 h. Each culture was harvested and centrifuged at 7,000×g for 10 min and washed with 0.01 M phosphate-buffered saline (pH 7.2) (PBS) three times. Bacterial cultures were resuspended in 5 ml of PBS to an optical density of 1.0, which approximates $10^9$ CFU/ml. Equal volumes of cell suspensions of each serotype were combined as inoculum for tomato plants. The five-strain cocktail was further diluted in PBS at 1:4 ratios as inoculum for soil inoculation studies.

Plant Preparation.

Surfaced-sterilized tomato seeds (*Solanum lycopersicum* 'Micro-Tom') were planted in potting mix (SunGrow Metro-Mix) in the greenhouse, USDA-BARC West, Beltsville, Md. At two weeks post-seedling, seedlings were transplanted to steam-sterilized eastern shore soil (~300 g) in 6"diameter Azalea pots placed on a saucer to serve as a water reservoir to avoid directly watering the plants. Eastern Shore soils were collected from the station farm at Virginia Tech Agricultural Research Extension Center (AREC) in Painter, Va. Plants were transferred to Conviron E7/2 climate-controlled growth chambers (Winnipeg, Canada) for experiments. Growth chamber Temperature were maintained at 25° C. (daytime) and 23° C. (nighttime) with a day and night cycle of 12 h and relative humidity of 65%. The saucer was refilled with ca. 10 mm water at 2-day intervals. Additionally, plants received tomato & blossom set spray treatment, per manufacturer's instructions, as yellowing developed to speed harvest and increase yield. Neptune's Harvest organic fish and seaweed fertilizer (purchased from www.amazon.com) was also applied as necessary throughout the growing period. All pots were randomized throughout the growth chamber, and subsequent analysis was performed on the data using a completely randomized design.

Soil Inoculation with *S. enterica*.

A total of twenty-two seedlings at 1 week post-transplant were used in the soil experiment. Plants were divided into two treatment groups: a control (inoculated with PBS, 4 plants) and an experimental group (inoculated with soil inoculum, 18 plants). 4 ml of soil inoculum (five-strain cocktail: PBS as 1:4 volume ratio) or PBS was directly injected into *rhizosphere* soil using a pipette tip. One core of *rhizosphere* soil sample (10 g) from each plant was taken with a sterile cork borer at 4, 8, and 16 days after inoculation to determine the survival of *Salmonella*. Around 100 *Salmonella* colonies with 10 and 6 colonies from each *Salmonella* positive soil samples were randomly picked for serological surveillance at day 8 and 23 following inoculation, respectively. Stems from all 18 plants were used for recovery of endophytically colonized *Salmonella* with the method described below at 23 dpi (day post inoculation).

Leaf Inoculation with *S. enterica*.

A total of twenty-two seedlings were divided into two treatment groups at 14 d post-transplant: a control group (inoculated with PBS, 4 plants) and an experimental group (inoculated with five-strain cocktail, 18 plants). Six to 9 leaflets per plant were used for inoculation. Leaflets were lightly dusted with 400 mesh carborundum to abrade the surfaces and create wounds necessary for the entry of bacteria. A total of 2 drops of inoculum (5 µl/drop) was spread over the upper surface of the leaflet. Three inoculated leaflets from each plant were sampled with a sterile scalpel at 0, 8, and 16 days after inoculation to determine the survival of *Salmonella*. Around 100 *Salmonella* colonies with 10 and 8 colonies from each *Salmonella* positive leaf samples were randomly picked for serological surveillance at day 8 and 23 after inoculation, respectively.

Blossom Inoculation with *S. enterica*.

A total of 38 plants at blossom stage were divided into two treatment groups: a control group (inoculated with PBS, 4 plants) and an experimental group (inoculated with five-strain cocktail, 34 plants). Over 170 blossoms were painted with cotton swabs containing the five-strain cocktail inoculum. Inoculated blossoms were marked individually. One blossom from each plant was sampled with a sterile scalpel at 0 and 7 days after inoculation to determine the survival of *Salmonella*. Around 100 *Salmonella* colonies with 10 colonies from each *Salmonella* positive blossom samples were randomly picked for serological surveillance at day 7 after inoculation.

Inoculation of Soil with *S. enterica* for the Internalization Experiment.

Two-tiered experiments were conducted to investigate the translocation of *S. enterica* in tomato plants (cv. Micro-Tom) from soil. In the first experiment, a total of 22 seedlings were used right after transplanting, with 18 inoculated and 4 held as controls. In the second experiment, a total of 24 seedlings were planted. The 24 pots were evenly distributed between two growth chambers. One chamber contained the plants inoculated right after transplanting. The other chamber contained the plants inoculated 1 week after transplanting. Plants in each chamber were divided into two treatment groups: a control group (inoculated with PBS, 2 plants) and an experimental group (inoculated with soil inoculum, 10 plants). Four milliliter of soil inoculum (five-strain cocktail: PBS as 1:4 volume ratio) or PBS was directly injected into the *rhizosphere* soil using a sterile pipette tip. A saucer was used to serve as a water reservoir to avoid splash from directly watering the plant and no contact was made between the treatment and the rest of the plant to avoid cross contamination throughout the experiment. Stems from 6 inoculated plants in the first experiment and all 20 inoculated plants in the second experiment were subjected to isolation of *Salmonella* at 7 dpi. Middle and top leaves as well as fruit samples were collected at the early fruit stage in the first experiment.

Soil, Leaf, and Blossom Sample Testing Procedures.

Each sample was aseptically transferred into individual, sterile Whirl-Pak™ filter bag. Modified buffered peptone water (mBPW) (9) was added to each sample bag of soil (20 ml), leaflets (10 ml), or blossoms (10 ml). After hand massaging for 2 min, the homogenate was diluted 10-fold in PBS and 0.1 ml aliquots of the appropriate dilutions were spread onto XLT-4 agar (Becton Dickinson and Company, Sparks, Md.). After 20 to 24 h incubation at 37° C., typical *S. enterica* colony formation was considered a presumptive positive. Presumptive positive colonies were transferred to triple sugar iron agar (TSI) and lysine iron agar (LTA) slants and incubated for 24 h at 35° C. Growth from presumptive-positive TSI slants was confirmed as *Salmonella* with somatic group antisera (Statens Serum Institute, Copenhagen, Denmark) and *Salmonella* molecular serotyping using the Luminex/Bioplex system (Fitzgerald, C. et al., J Clin Microbiol 2007 45: 3323-3334; and McQuiston, J. R. et al., J Clin Microbiol 2011 49: 565-573).

Recovery of Endophytically Colonized *Salmonella* from Stems.

Figure 19B:
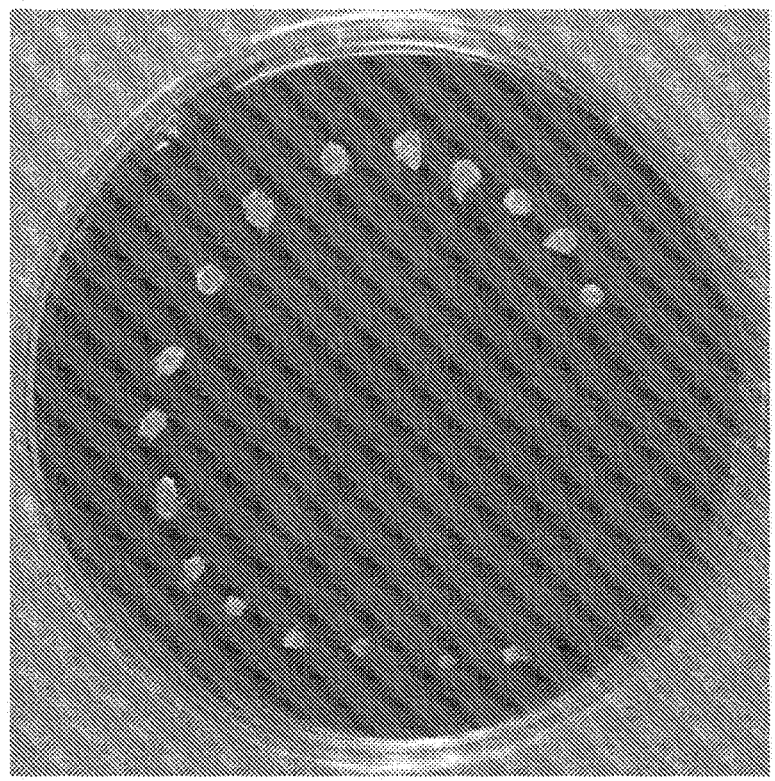
FIG. 19 shows endophytic colonization of Salmonella in stem. A five-strain cocktail was inoculated into the soil of the tomato plant root zone right after transplanting. At 7 dpi, stems were removed and surface sterilized. Pieces of stem tissue were placed immediately after sectioning onto the surface of XLT-4 agar medium in a positional order from top to bottom following the arrow on the plate. Appearance of typical Salmonella colonies on XLT-4 within 3 days at RT followed by further isolation and confirmation is positive (a); otherwise a sample is negative (b).
Figure 19A:
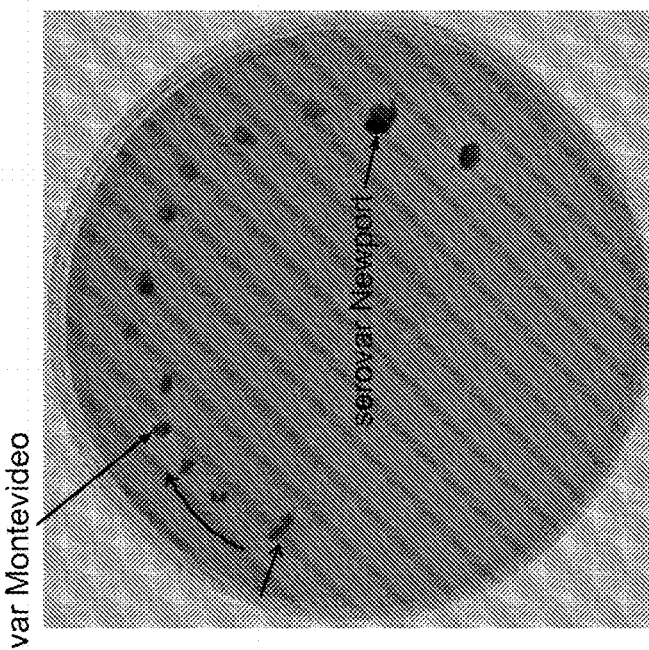

At 7 or 23 dpi, the stem from 1 cm above the soil was aseptically removed from the plant. After removing all side branches, the main stem remained for analysis. Sterile distilled water was used immediately to clean the outside of the main stem. After transporting back to the lab in plastic zip-lock bags, stem samples were immersed in 70% ethanol for 1 min, 5% Clorox for 1 min, 70% ethanol for 1 min, and 1% silver nitrate ($AgNO_3$) for 20 min, respectively for surface wetting, and sterilization. Stem samples were then washed with sterile $ddH_2O$ for 1 min to remove silver nitrate. The stem was divided into pieces 0.5 cm long with a sterile scalpel from the top to bottom, and the last piece at the bottom was discarded. Each piece of stem tissue was placed immediately after sectioning onto the surface of an XLT-4 agar medium in a positional order from top to bottom (FIG. 19). The appearance of typical *Salmonella* colonies on XLT-4 was observed daily for 3 days at RT for further isolation and confirmation as described above.

Middle and top leaves were aseptically removed from the plant using sterile scissors. The leaves were surface-sterilized by spraying with 70% ethanol and allowed to dry under a flow hood until no visible solution remained (Hintz, L. D. et al., Fruit, Roots, Stems, and Leaves. HortScience 2010 45: 675-678; and Miles, J. M. et al., J Food Prot 2009 72: 849-52). The excised leaves were aseptically combined in one stomacher bag for each plant and treated as a single sample.

Fruit Sampling and Testing Procedure.

For each experiment, both green and red ripe tomato fruits were harvested from plants in experimental and control groups. For soil and leaf inoculation experiments, one or two fruits were randomly sampled from each plant to test for *S. enterica* presence. For blossom inoculation experiments, a total of 90 tomatoes, 71 produced from inoculated blossoms and 19 from uninoculated blossoms, were harvested in the experimental group. Tomatoes were aseptically picked into a sterile Whirl-Pak™ filter bag individually using sterile scalpels and transported to the lab. 10 ml of mBPW was added to each tomato sample bag at room temperature (RT). Potential surface populations were dislodged by 2 min of hand rubbing. The tomato was removed from the mBPW wash suspension and immersed in 70% alcohol for 2 min for surface disinfection and then allowed to dry under a laminar flow hood until no visible ethanol remained. Tomatoes from control groups were always treated last using the same ethanol to confirm ethanol disinfection efficiency. After aseptically removing the pedicle and calyx, each fruit was then placed in an individual sterile Whirl-Pak™ filter bag containing 10 ml of mBPW and stomached for 60 s at 230 rpm with a Stomacher® 400 circulator (Seward, London, UK). Both mBPW wash suspensions and fruit homogenates were incubated for 24 h at 35° C. Aliquots of 0.1 mL from the incubated pre-enrichments were subcultured to 10 mL of tetrathionate (TT) broth. TT broth was incubated for 24 h at 35° C. Incubated selective enrichment broth was streaked (10 µl) onto XLT-4 agar plates. After 24 h incubation at 35° C., typical *S. enterica* colony formation was considered as presumptive positive and transferred to triple sugar iron agar (TS') and lysine iron agar (LIA) slants for 24 h at 35° C. Growth from presumptive-positive TSI slants was confirmed as *Salmonella* as described above.

Molecular Serotyping.

The standard protocol for molecular determination of serotype in *Salmonella* from the Centers for Disease Control and Prevention (CDC) was followed (CDC (2009) Standard Protocol Molecular Determination of Serotype in *Salmonella*. Workshop on Molecular determination of Serotype of *Salmonella*: Centers for Disease Control and Prevention, Atlanta, Ga.). Briefly, the O-grp-1 assay (a six-plex PCR reaction) (Fitzgerald, C. et al., J Clin Microbiol 2007 45: 3323-3334) and H-ag assay (a 20 primer multiplex PCR reaction) (McQuiston, J. R. et al., J Clin Microbiol 2011 49: 565-573) were performed in a thermal cycler with the following parameters: initial denaturation at 15 min; then 30 cycles of 94° C. for 30 s, 48° C. for 90 s, and 72° C. for 90 s; and 72° C. for 10 min. PCR amplicons were then used directly with coupled beads (Radix Bio Solutions, Georgetown, Tex.) in the following hybridization reaction. 33 µl of corresponding bead mix was added to 5 µl of PCR product from the O-grp-1 assay or H-ag assay and 12 µl of TE buffer in a single well of a low profile 96-well microtiter plate (Bio-Rad, Hercules, Calif.). The reaction mixture was incubated first for 5 min at 94° C. and then for 30 min at 52° C. to denature the DNA and allow hybridization of the probes to the PCR amplicons. Microspheres were then suspended in 75 µl of detection buffer (R-phycoerythrin-conjugated streptavidin [Life Technologies, Grand Island, N.Y.] and diluted to 4 µg/ml in 1×TMAC hybridization buffer). Samples were incubated for an additional 10 min at 52° C. and then analyzed on the Bio-Plex (Bio-Rad, Hercules, Calif.). The median fluorescence intensity (MFI) for each bead set was calculated automatically by the BioPlex software. A positive signal was defined as an MFI yielding 6× the background fluorescence intensity for each bead-probe set.

Statistical Analysis.

For serological surveillance on *Salmonella* colonies isolated from leaf, blossom and soil samples, an estimated percent and a confidence interval (CI) were calculated for each of the five serovars used in the study. The estimated percent equals the number of samples of the specified serovar divided by the total number of samples (around 100 colonies per each sample type). In the case of one serovar (*Typhimurium*) that did not show up in the surveillance data, its upper confidence bound was the highest proportion such that observing none had a 5% chance of occurring. Otherwise, all possible outcomes were ordered by the number of serovars of the specified type. The method of Clopper, C. J. and Pearson, E. S. were used to calculate CI (Clopper, C. J. et al., Biometika 1934 26: 404-413). That is, the lower confidence bound is minimum p such that Pr (all possible outcomes≥the actual outcome)=0.025. The upper confidence bound is the maximum p such that Pr (all possible outcomes≤the actual outcome)=0.025. In both cases, p denotes the probability that a serovar was the type specified.

Results:

Survival of *S. enterica* on Tomato Plant.

Figure 16:
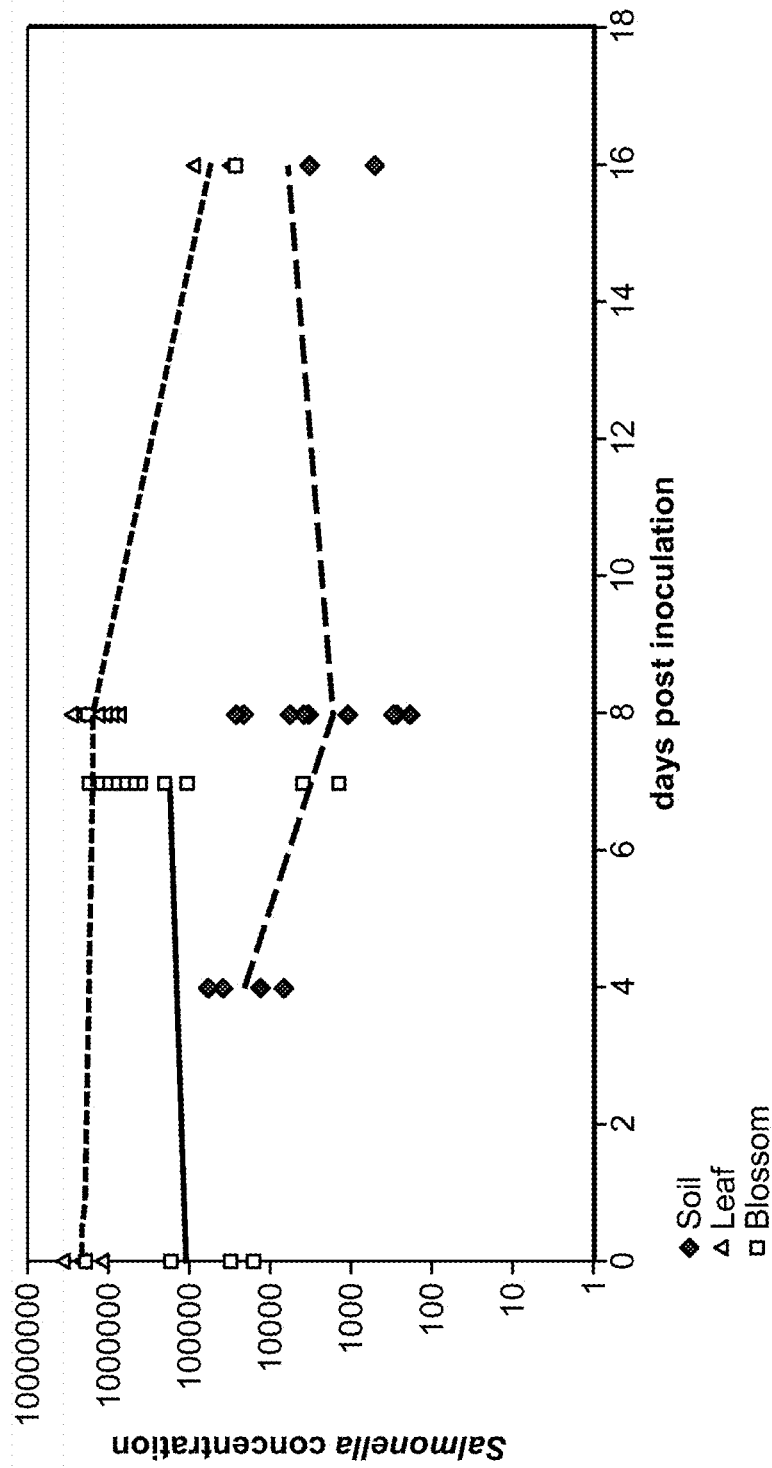
FIG. 16 shows Salmonella enterica populations in soil (♦, CFU/g), on leaves (▲, CFU/leaf), and blossoms (■, CFU/blossom) of tomato plants after inoculation. Average S. enterica populations are shown as lines: soil (--), leaves (----) and blossoms (-).

The ability of *S. enterica* to persist on tomato plants was indicated by the detection of *Salmonella* colony-forming units (cfu) in soil *rhizosphere*, leaflet, and blossom samples (FIG. 16). The trend of *Salmonella* growth varied across inoculation sites. For example, *Salmonella* actually grew in blossoms while average concentrations of *Salmonella* decreased in soil and on leaflets during the same time course. In addition, the decreasing slope in *Salmonella* survival was much steeper in soil than on leaflets. Average total numbers of *Salmonella* dropped to around $10^4$ cfu per gram in soil at 8 days post inoculation (dpi), while *Salmonella* counts held at around $10^6$ cfu per leaflet at 8 dpi.

*S. enterica* Serovar-Specific Niche Colonization of Tomato Plants.

Figure 17A:
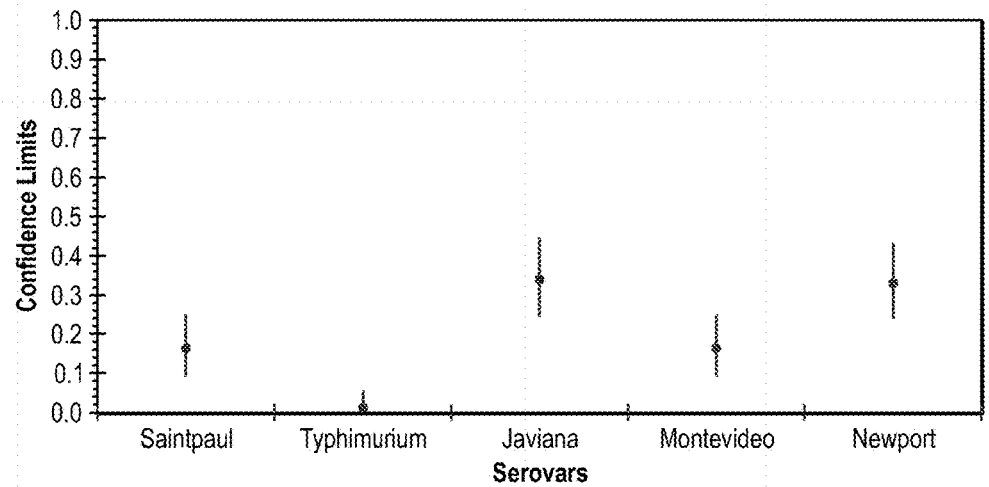
FIG. 17 shows the molecular serology prevalence per Salmonella enterica Sainpaul, Typhimurium, Javiana, Montevideo, and Newport in soil rhizosphere, on leaves, and on blossoms of tomato plants after inoculation. A five-stain cocktail was inoculated into soil and onto leaves, and flowers of tomato plant in corresponding experimental group. At day 8 and day 23 after soil inoculation (A, B), or leaf inoculation (C, D), or day 7 after blossom inoculation (E), around 100 Salmonella colonies with 6 to 10 colonies from each Salmonella positive sample were randomly picked for serological surveillance. Dot represents estimated percent for each of the five serovars in around 100 salmonellae colonies isolated from each sampling and line represents the 95% lower and upper confidence interval (CI).
Figure 17B:
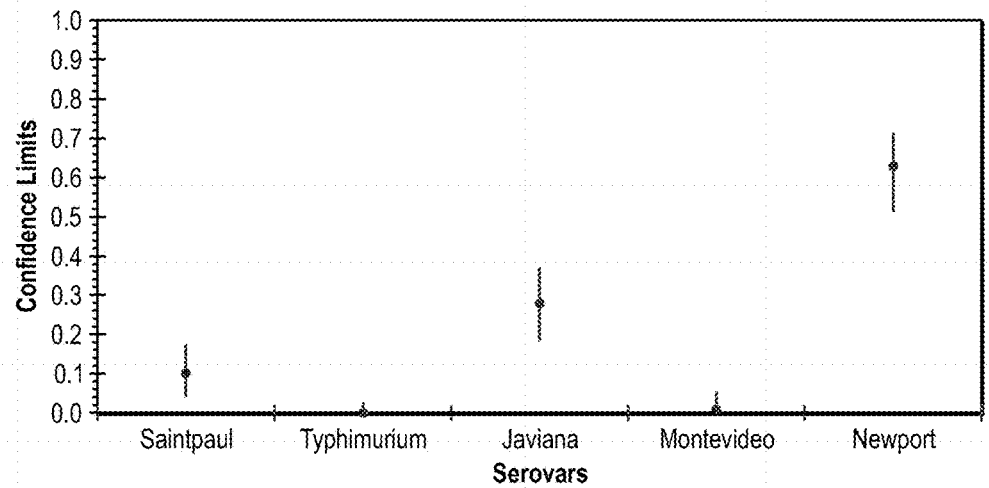
Figure 17C:
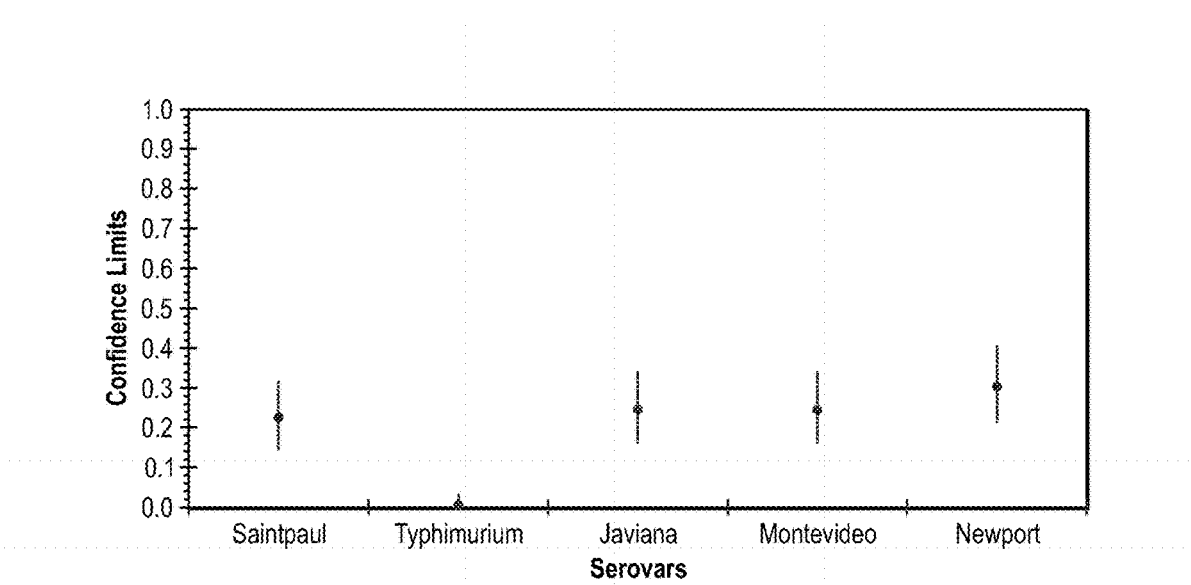
Figure 17D:
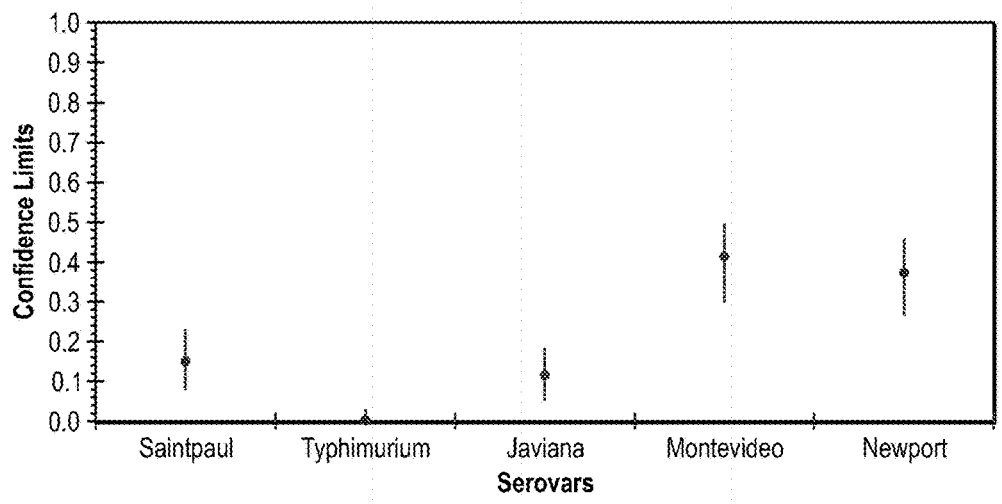
Figure 17E:
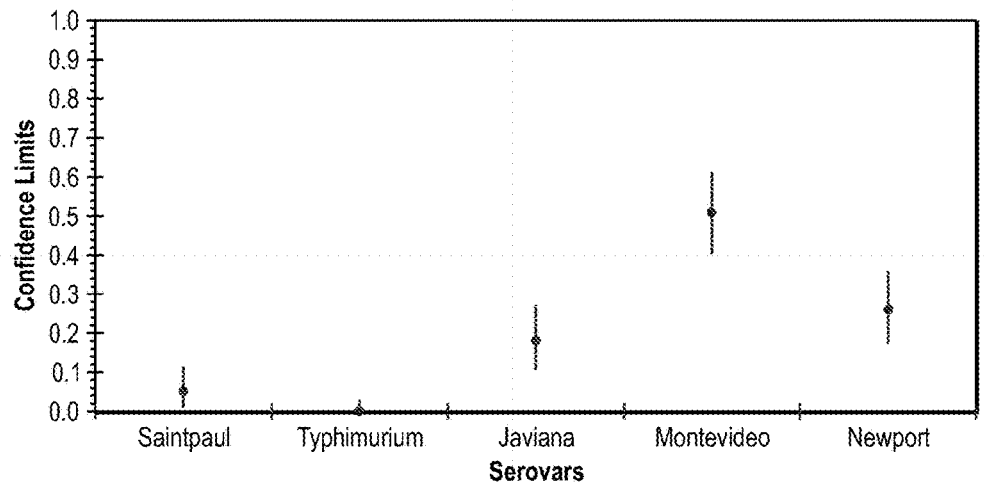

The number of *Salmonella* colonized plants was significantly affected by the *S. enterica* serovar added in soil *rhizosphere* ($\chi^2$=57.61; P<0.0001 at day 23 post inoculation), leaf ($\chi^2$=38.89; P<0.0001 at day 23 post inoculation) and blossom ($\chi^2$=36.98; P<0.0001 at day 7 post inoculation). Surprisingly, a different colonization pattern by the five *S. enterica* serovars comprising the *Salmonella* cocktail was observed based on molecular serology screening (FIGS. 17A-17E). In particular, *S. enterica* serovar Newport and Javiana colonized *rhizosphere* more easily than other serovars at both 8 dpi (Newport 33%, 95% confidence interval, 24%-43%; Javiana 34%, 95% confidence interval, 25%-44%) and 23 dpi (Newport 62%, 95% confidence interval, 52%-71%; Javiana 27%, 95% confidence interval, 19%-37%) (FIGS. 17A and 17B). On the other hand, serovars Montevideo and Newport showed greater fitness on leaves over time (FIG. 17D). Moreover, colonization was observed similarly among all serovars save for *S. Typhimurium* at 8 dpi (FIG. 17C). In blossoms, 51 colonies were identified as S. Montevideo (95% confidence interval, 41%-61%) out of the 100 *Salmonella* positive colonies sampled, indicating its superior fitness for this plant organ (FIG. 17E). It is interesting to note that almost no colonization of *S. Typhimurium* was observed on either of the plant organs studied here.

S. enterica Contamination of Fruit Via Blossom.

In total, 112 red/green cherry tomatoes were harvested and analyzed for the presence of *Salmonella* (Table 1).

TABLE 1

*Salmonella enterica* contamination of tomato fruits via blossom[a].

|  |  |  | *S. enterica* positive |  |  |
|---|---|---|---|---|---|
|  | # of tomato from | Positive rate | Surface only | Inside only | Both surface and inside |
| Experimental group | Inoculated blossom (71) | 70.4% | 21 | 1 | 28 |
|  | Uninoculated blossom (19) | 15.8% | 2 | 0 | 1 |
| Control group | Control blossom (22) | 0% | 0 | 0 | 0 |

[a]A five-strain cocktail was inoculated onto individual labeled blossoms of tomato plants. All the tomato fruits derived from inoculated and uninoculated flowers in experimental or control groups were harvested and screened for surface and internal populations of *Salmonella*.

Twenty-two of these tomatoes originated from control plants un-inoculated with *Salmonella*, and 90 from plants inoculated by flower brushing, with an unexpected 19 more from adjacent blossoms that were not inoculated with *Salmonella*. It is important to note that no *Salmonella* was detected on tomatoes from uninoculated control plants either by plating enriched samples of mBPW wash water or tomato pulp homogenates. However, *Salmonella* was detected on or in tomatoes that developed from experimentally inoculated blossoms as well as adjacent uninoculated blossoms (Table 1).

Figure 18:
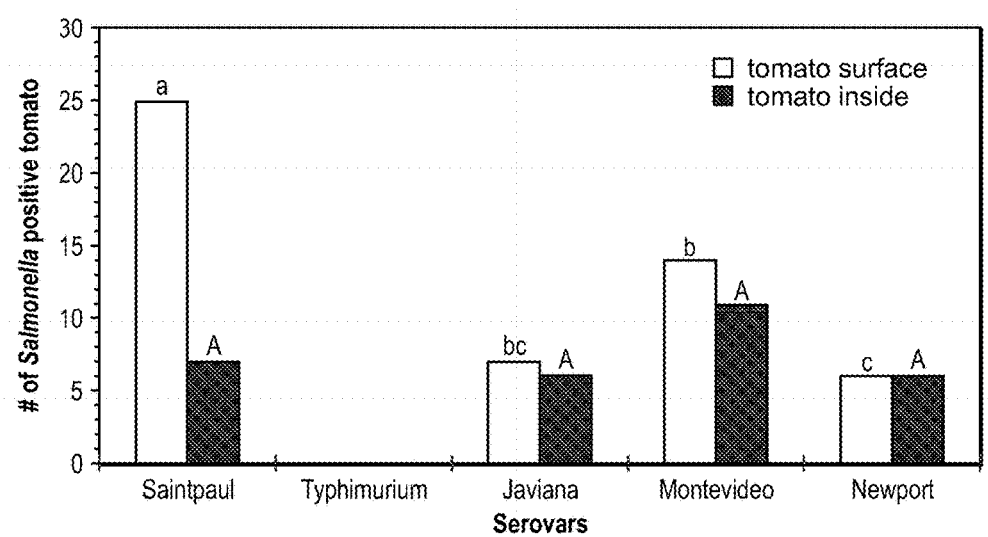
FIG. 18 shows the recovery of each Salmonella serovar on and within tomato fruit derived from inoculated blossoms. A five-strain cocktail was inoculated onto individual labeled blossoms of tomato plants. All the tomato fruits derived from inoculated and uninoculated flowers in the experimental group were harvested and screened for surface and internal populations of Salmonella. Molecular serotyping was used to determine the serovar of isolated Salmonella colonies. Different Capital letters or different lowercase letters represent significant differences between serovars ($P<0.05$).

Additionally, fifty of seventy-one tomatoes (70%) harvested from inoculated blossoms were positive for *Salmonella*. Of the fifty *Salmonella*-positive tomatoes, 21 contained the pathogen on the fruit surfaces only, as *Salmonella* was detected only in mBPW wash water but not whole tomato homogenate (Table 1). Twenty-eight tomatoes, however, were found to have *Salmonella* both on the surface and internally, and one tomato was found that harbored the pathogen internally only (Table 1). Interestingly, three out of 19 tomatoes harvested from adjacent uninoculated blossoms were positive for *Salmonella* as well, with two retaining *Salmonella* on surfaces only and one with *Salmonella* both on the surface and inside. Furthermore, 17 tomatoes were found to harbor more than one serotype. Consistent with previous observations above, *S. Typhimurium* was not found in or on tomatoes. While *S. enterica* serovar Saintpaul was the most prevalent serovar isolated on tomato surfaces (25/52, 48%), S. Montevideo was the most frequently isolated serovar inside tomatoes (11/30, 37%) (FIG. 18). Even though no significant difference between breaker and red ripe tomatoes was noted in terms of *Salmonella* positive rate, a significant interaction was indicated between fruit ripeness (Green vs. Red/breaker) with respect to *Salmonella* positivity (p<0.05) (Table 2).

TABLE 2

*Salmonella enterica* contamination of tomato fruits with respect to fruit ripeness.

|  |  | *Salmonella* positive (%) |  |  |  |
|---|---|---|---|---|---|
|  | Total tomatoes | On/in tomato | On tomato only | In tomato only | Total [a] |
| Green | 43 | 11 | 6 | 0 | 17 (39.5%) B |
| Breaker | 21 | 8 | 8 | 0 | 16 (76.2%) A |
| Red | 26 | 10 | 8 | 1 | 19 (73.1%) A |

[a] Values followed by different letter are significantly different (P < 0.05).

Internalization and Migration of *S. enterica* in Tomato Plants Via Soil.

In the first internalization experiment, a total of 48 plant samples were collected from inoculated plants with 6 stems collected at 7 days post transplant (PT) and 12 top and middle leaves and 30 fruits collected at early fruit stage for recovering endophytically colonized *Salmonella*. Eighteen plant samples were collected at early fruit stage from four control (i.e. un-inoculated) plants (4 stems, 4 leaves, and 10 fruits). All leaves or tomato fruits sampled were composited for each plant after surface disinfection. No samples from control plants were positive for presence of *Salmonella*. Of the tomato plants grown with *Salmonella* infested soil, 22% (4 out of 18) contained endophytically colonized *Salmonella* based on direct plating or enrichment procedures, including two stem samples, one leaf sample, and one fruit sample. *S. enterica* Saintpaul was isolated from the single positive leaf sample and S. Newport was found from the surface and inside the single positive tomato sample. More interestingly, *Salmonella* was able to move up to 10 cm inside the stem within a week after inoculation, and multiple serovars including Newport, Montevideo and Saintpaul were recovered from different stem segment pieces (FIG. 19).

In the second tier experiment, two of ten stem samples (20%) were positive for endophytically colonized *Salmonella* when the plant was inoculated right after PT (within 1-3 days) while no *Salmonella* was recovered from the plants inoculated 7 d PT (Table 3).

TABLE 3

Recovery of endophytically colonized *Salmonella enterica* from tomato plant (cultivar: Micro-Tom)[a].

| Inoculation time post transplant (PT) | plants analyzed in each experiment | No. of *Salmonella* positive (%) | No. of positive in total[e] |
|---|---|---|---|
| Right after PT (within 1-3 days) | 18[b] | 4 (22%) | 6/28 A |
|  | 10[c] | 2 (20%) |  |
| 7 d PT | 18[d] | 0 (0%) | 0/28 B |
|  | 10[e] | 0 (0%) |  |

[a]A five-strain cocktail was inoculated into the soil of tomato plants' root zone. The presence of *S. enterica* inside plant tissues was evaluated by sanitizing the exterior of the sample before direct plating or enrichment.
[b]Among 18 plants, only stems were sampled from 6 plants at 7 day post inoculation (dpi); top and middle leaves and tomato fruits were sampled from the remaining 12 plants at early fruit stage (plants had one or more green fruit). Leaves or fruits were composite for each plant after surface disinfection.
[c]Only stems were sampled from plants at 7 dpi.
[d]Only stems were sampled from plants at 23 dpi.
[e]Values followed by different letters are significantly different (P < 0.05).

Subce internalization of *Salmonella* in tomato plant (cv. Micro-Tom) was evidenced by recovery from stem and fruit, the time window when *Salmonella* internalization may occur was also investigated. By combining all stem data (Table 3), a significant interaction between inoculation time post-transplant and recovery of endophytic Salmonella ($\chi^2$=7.7; P<0.01) emerges. In other words, Salmonella appears more likely to invade root and stem systems right after transplanting compared to 7 d PT.

Conclusions:

Virginia ranks third in the nation, behind California and Florida, in fresh-market tomato production (USDA ERS, posting date. Vegetables and Melons: Tomatoes. USDA Economic Research Service. [Online.]). The majority of Virginia's tomato acreage is located on the Eastern Shore (VES). Almost annually, since 2002, a VES-grown tomato-associated outbreak or incident caused by Salmonella, specifically S. Newport, has been documented. Previous studies have shown the persistence of Salmonella in various ecological niches of this agricultural region (Barak, J. D., and A. S. Liang., PLoS One 2008 3:e1657; Gorski, L. et al., Appl Environ Microbiol 2011 77:2734-48; Hanning, I. B. et al. Foodborne Pathog Dis 2009 6:635-48; and Patchanee, P., B. et al. Foodborne Pathog Dis 2010 7:1113-20). Most recently, ecological surveillance data on VES tomato farms provided by Sapkota et al. (Micallef, S. A. et al., Environmental Research 2012 114:31-39) yielded further evidence that Salmonella is persists in this tomato growing microcosm. This was particularly noted in pond water, often used for irrigation, or creek water that flowed downstream of the pond, pond/creek sediment, and rhizosphere soil. The recent isolation of a S. Newport strain from an irrigation pond that matched an outbreak strain (Greene, S. K. et al., Epidemiol Infect 2005 136:157-65) demonstrated that it is still possible for pond water to contribute to Salmonella contamination of tomatoes even with the practice of using drip irrigation and plasticulture. Studies have been carried out experimentally to examine possible routes for S. enterica to contaminate preharvest tomatoes. Salmonella has been shown to internalize into tomato plants through roots (Hintz, L. D. et al., HortScience 2010 45:675-678), leaves (Gu, G., J. et al, PLoS One 2011 6:e27340), and blossoms (Guo, X., J. et al, Appl Environ Microbiol 2001 67:4760-4; and Shi, X. et al, J Food Prot 2007 70:2725-31). Here, the findings provided further evidence by showing with a Micro-Tom cultivar (Barak, J. D. et al., Appl Environ Microbiol 2011 77:498-504) grown in VES sandy loam soil, Salmonella was able to internalize into the tomato plants via roots from inoculated soil and blossoms, leading to contamination of developing tomato fruits. It is noteworthy that the fruit contamination rate was much higher with Salmonella introduction through flowers (70.4%). Equally remarkable was the observation that after Salmonella colonized the blossom, it not only proliferated but also persisted at least 35 more days to fruit development, accentuating the potentially high risk, for fresh tomato safety.

Contradictory opinions abound regarding whether or not Salmonella enterica can internalize tomato plants through the root system (Guo, X. et al., Appl Environ Microbiol 2002 68:3639-43; Hintz, L. D. et al., HortScience 2010 45:675-678; and Miles, J. M. et al., J Food Prot 2009 72:849-52). The findings described herein, however, revealed that, aside from cultivar, serovar type and introduction time post-transplant are two key factors affecting Salmonella internalization through the root system. Bernstein et al. (Bernstein, N. et al., Irrig. Sci. 2007 26:1-8) has shown that S. Newport is capable of persisting in potting medium for 4.7 to 10 weeks. In this study, serovars Newport and Javiana appeared to colonize sandy loam soil much better than other serovars including S. Montevideo, S. Saintpaul, and S. Typhimurium. Specifically, S. Newport was recovered from 100% of plant soil rhizosphere samples screened and 62% of the salmonellae isolated at 23 days post inoculation (dpi). Through recovery of endophytic Salmonella from stems, this study illustrated clearly that time-dependent factors are also important for Salmonella internalization via the root system. That is, inoculation within three days post transplanting (average 20%) yielded significantly higher recovery of endophytically colonized Salmonella than one week after transplantation (0%). Plant wounding or stress induced by abiotic factors (Hallmann, J. et al., Canadian Journal of Microbiology 1997 43:895-914) during transplantation probably underscores this bias observed for Salmonella entrance. In practice, tomato crop is grown from plants started in greenhouses, hotbeds, or cold frames. Seedlings are transplanted when they are about 2 inches high. Transplanting tends to promote the natural taproot system into a more fibrous one, permitting an earlier ripening of fruit and a longer season for growth (Weaver, J. E., and W. E. Bruner. 1927. Chapter XXVI: Tomato. Root Development of Vegetable Crops, First ed. McGraw-Hill Book Company, Inc., New York). However, interior root colonization may occur passively through wounds in roots damaged during transplantation (Hallmann, J. et al., Canadian Journal of Microbiology 1997 43:895-914). Moreover, methyl bromide has had a long history of use in tomato cultivation as a soil fumigant in the eastern United States, and a recent metagenomic study showed such practices have diminished overall soil microbial diversity, signalling increased potential risk for Salmonella colonization and persistence in the soil. Taken together these findings indicate that Salmonella can be introduced to soil via potentially contaminated irrigation water. In VES, certain serovars, such as S. Newport, are well adapted to soil and tomato crops. During the transplantation stage, a tomato plant is more susceptible to internalization, thereby increasing the occurrence of Salmonella internalization in the plant, and, subsequently, causing increased risk of Salmonella contamination of pre-harvest tomato fruits.

Not surprisingly, this study failed to recover Salmonella from tomato fruits via the inoculated leaf. No recovery of Salmonella from other leaf surfaces or tomato fruits may have been due to the usage of saucers as water reservoirs, thus avoiding splashing from direct plant water, and cross-contamination throughout the experiment. Salmonella internalization in the presence of carborundum or other surfactants, may not be significant for leaf surfaces as the rate of internal fruit contamination is significantly low in this regard (Gu, G. et al., PLoS One 2011 6:e27340). With the number of plants used in this study, any observation of Salmonella contamination of tomato fruits via the inoculated leaf may be a mere random event.

Multiple Salmonella serovars have been reported concurrently in the same freshwater (Haley, B. J. et al., Appl Environ Microbiol 2009 75:1248-55; and Patchanee, P. et al., Foodborne Pathog Dis 2010 7:1113-20) and sediment (Haley, B. J. et al., Appl Environ Microbiol 2009 75:1248-55; Micallef, S. A. et al., Environmental Research 2012 114:31-39; and Patchanee, P. et al., Foodborne Pathog Dis 2010 7:1113-20). However, only a few serovars of Salmonella are repeatedly linked to outbreaks associated with tomatoes suggesting that certain serovars are more adapted to the tomato plant environment. In light of serovar-specific niche adaptation, strains from different serovars that were previously associated with tomato or produce-linked outbreaks were selected, and a five-strain cocktail was introduced in this study as opposed to inoculating different serovars individually. Going further than a demonstration of basic serovar competition, this study demonstrated clearly specific serovar-tomato crop interactions in different parts of the tomato plant including soil rhizosphere, leaf, and blossom. S. Newport is the most persistent and dominant serovar over time in the soil rhizosphere. Conversely, no difference was noted among serovars on leaf in terms of prevalence with the exception of S. Typhimurium at 7 dpi. It was noteworthy, however, that over time, S. Montevideo and S. Newport appeared to be more adapted to survival in the leaf microcosm. Guo et al. (Guo, X. et al., Appl Environ Microbiol 2001 67:4760-4) and Shi et al. (Shi, X. et al., J Food Prot 2007 70:2725-31) both reported that S. Montevideo was the most persistent serovar recovered within tomatoes by introduction through blossoms of growing plants. In line with those findings, this study affirmed S. Montevideo adaptation to tomato blossom, followed by serovars Newport and Javiana. All *Salmonella* serovars introduced onto blossoms except S. Typhimurium were recovered within developing tomato fruits at a similar level (P>0.05) even though Montevideo was most frequently isolated within tomatoes. However, when one takes the factor of tomato ripeness into account, both S. Montevideo and S. Newport were more adapted (P<0.05) than other serovars. Consistent with Garcia's findings (Garcia, R. et al., Appl Environ Microbiol 2010 76:5025-31), it was noted here that S. Typhimurium survived poorly in all plant parts examined in this study, suggesting that tomato contamination by S. Typhimurium may be more post-harvest in its etiology.

As mentioned above, a significant difference was noted in recovery of *Salmonella* from tomatoes in terms of fruit ripeness. "Vine-holding" tomatoes in the red or middle/late breaker stage of development may allow a greater chance for *Salmonella* contamination, since during ripening in tomatoes, declines in acid levels are accompanied by increases in sugars and lycopene but loss of plant cell wall integrity (Anthon, G. E. et al., J Sci Food Agric 2011 91:1175-81). These changes favor enhanced bacterial survival and indicate that vine-holding tomatoes in the field too long may increase the pre-harvest contamination risk of fruits headed to the fresh-cut market.

In summary, this study sheds light on *Salmonella* internalization by root uptake into healthy tomato plants. The results described herein indicate that internalization through the root system is a function of serovar and plant stage. These data also demonstrate categorically that both infested soil and contaminated blossoms can lead to internal fruit contamination.

Figure 20:
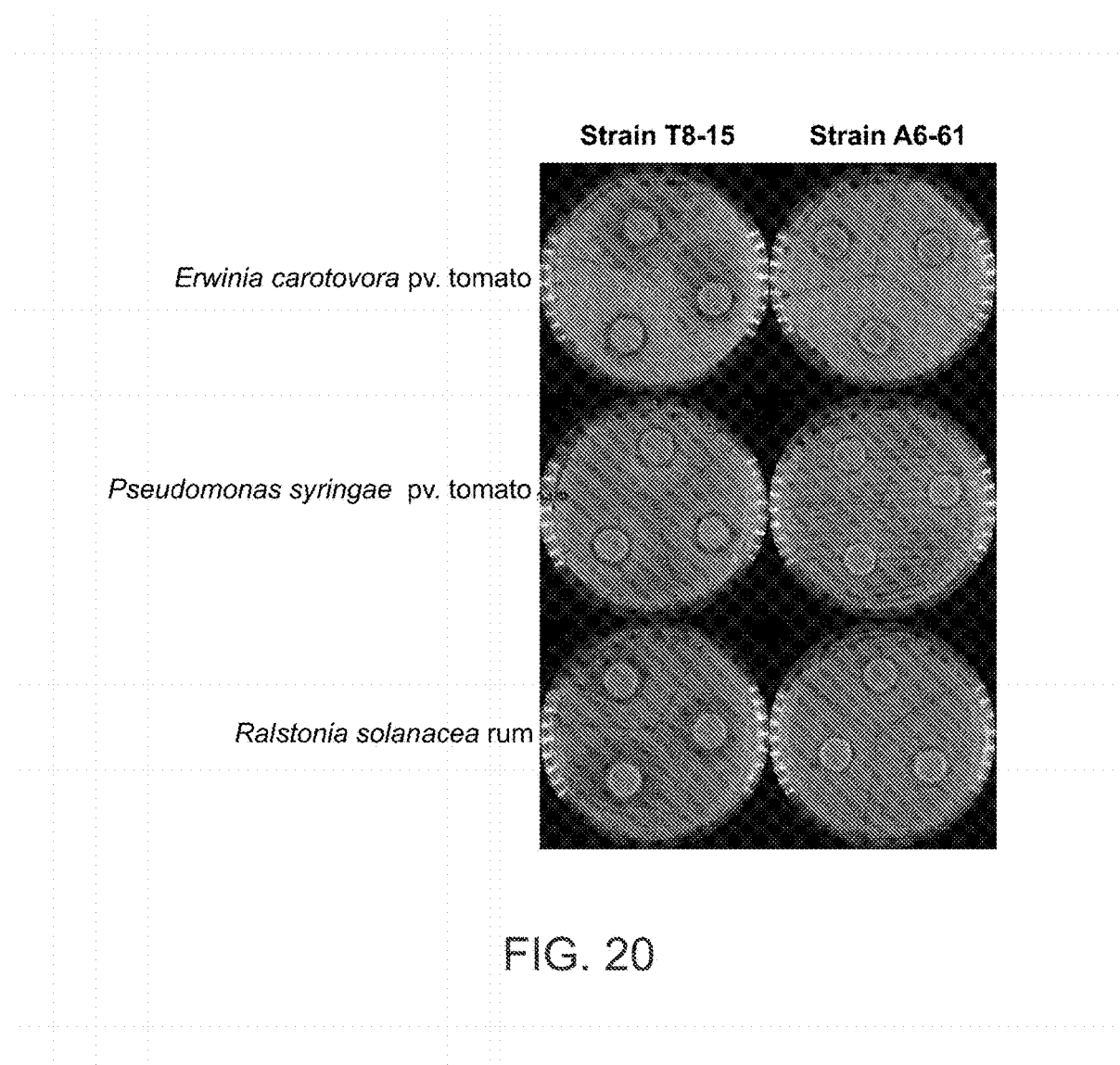
FIG. 20 shows the efficacy of TS-15 against three major plant pathogens associated with tomato plants.

Example 3: Efficacy of TS-15 Against Three Major Plant Pathogens Associated with Tomato/Pepper TS-15 and A6-6i were subjected to the in vitro agar plug method described previously to determine the efficacy against three major plant pathogens associated with tomato/pepper including *Pseudomonas syringae* pv. Tomato, *Ralstonia solanacearum*, and *Erwinia carotovora* subsp. *carotovora*. The zone of inhibition was measured at day 1, day 2, and day 4, respectively. Representative agar plates from day 1 are shown in FIG. 20. The results demonstrate that the control agent will not only control *Salmonella* and other enteric human foodborne pathogens, but will also control *Ralstonia solanacearum*, which causes bacterial wilt of tomato and pepper, and *Pseudomonas syringae* pv. tomato, which is the cause of bacterial speck on tomato and *Arabidopsis*. In addition, the control agent also inhibits *Erwinia carotovora* pv. tomato, which causes soft-rot of tomato stems.

Example 4: To Determine the Survival and Persistence of TS-15 in Tomato Field in Minimal Medium with Glucose and Yeast Extract as Carbon and Nitrogen Source, Respectively, for a 3-Month Period Survival of antagonist strain TS-15 for a 3-month period will be evaluated in a tomato field at The Virginia Eastern Shore Agricultural Research and Extension Center (AREC). In brief, rows of tomato cultivar BHN602 will be planted by hand with 1 m between rows. Fifteen plants randomly were selected for inoculation in each row. Two border rows of tomato plants will be maintained to surround an experimental row and a control row for each time point and will not treated. Biomass of antagonist TS-15 will be produced in minimal media with glucose and yeast extract as carbon and nitrogen source, respectively, in 500 ml flask and then transferred to sterile spray bottles, transported to the field on ice, and used within 24 h. A spray inoculation method will be used to mimic the industrial arrival of inoculum into the field. The survival of TS-15 at different inoculation sites including leaf, blossom, tomato, and bed soil will be observed on day 0 (3 hrs after inoculation), 1 month, 2 months, and 3 months post inoculation.

Example 5: To Determine the Survival and Persistence of TS-15 in Tomato Field in TSB:H2O (1:25) Diluent, for a 6-Month Period Additional survival of antagonist strain TS-15 for a 6-month period was evaluated in tomato field at The Virginia Eastern Shore Agricultural Research and Extension Center (AREC). In brief, rows of tomato cultivar BHN602 were planted by hand with 1 m between rows. Fifteen plants randomly were selected for inoculation in each row. Two border rows of tomato plants were maintained to surrounds an experimental row and a control row for each point and were not treated. Biomass of antagonist TS-15 was introduced in TSB:$H_2O$ (1:25) in 500 ml flask and then transferred to sterile spray bottles, transported to the field on ice, and used within 24 h. A spray inoculation method was used to mimic the industrial arrival of inoculum into the field. The survival of TS-15 at different inoculation sites including leaf, blossom, tomato, and bed soil were observed on day 0 (3 hrs after inoculation), day 1, day 4, day 30 and day 60 post inoculation.

Figure 21:
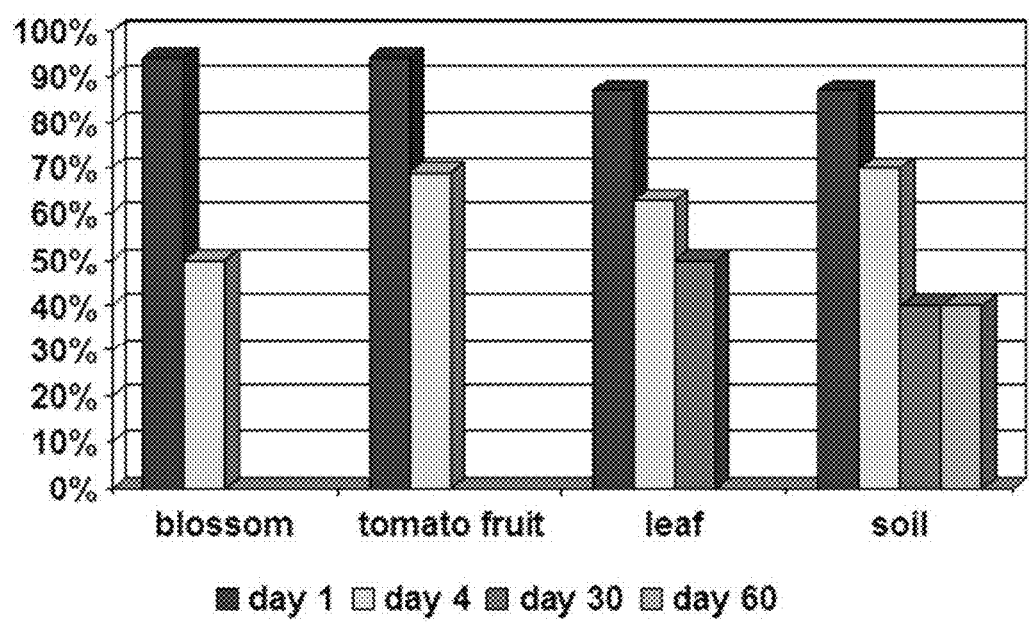
FIG. 21 is a graph that shows persistence of P. alvei TS-15 on tomato plants and soil environment. A spray inoculation method was used to inoculate tomato plant including leaves, blossoms and tomatoes, and soil from planting beds in a tomato field located in Painter, Va. The survival of TS-15 at different inoculation sites was observed on day 1, day 4, day 30 and day 60 post-inoculation. The number of samples with detectable TS-15 was counted.

Results:

At the end of the trial, *P. alvei* TS-15 persisted well through the first 4 days in the experiment in more than 50% (8 out of 15) samples taken from leaves, blossoms, tomatoes, and bed soil. While no detectable level of TS-15 was found on blossoms and tomatoes at day 30 post inoculation, at least 40% (6 out of 15) samples from leaf and bed soil were still positive for the presence of strain TS-15 (FIG. 21).

Example 6: To Develop a More Fit Mutant of TS-15 that Garners Greater Resistance to UV Radiation This is important since the control agent is applied in the field where it will be affected by UV and solar radiation, particularly near the unshaded crown areas of the tomato and pepper plants. This will involve a series of selection experiments in the laboratory based on set and sublethal exposure times to UV radiation sources of the same primary wavelength emitted by the Sun. Once mutants are found with increased vigor to UV assault, their performance as biocontrol strains against *Salmonella* will be evaluated. Ultimately their performance under actual sunlight conditions will be evaluated. An enhanced effect would be expected given that more cells would persist for longer periods of time on the crowns of plants and despite UV bombardment during the summer months of the growing season.

Example 7: Use of TS-15 as Biological Control Application with Other Members of the Nightshade (Solanaceae) Family and in Particular, Peppers in the Genus *Capsicum*

Bell pepper and several varieties of hot pepper will be subjected to similar laboratory and high tunnel trials with biocontrol strain TS-15 and *Salmonella enterica*. Given the similarities between tomato plants and fruits and the *Capsicum* plants and peppers, the effect is expected to be similar on pepper as to what was observed on all organs of tomato plants.

Example 8: Phenotyic Microarray Analysis

TS-15 and S. Newport were examined for cellular phenotypes using Biolog Phenotypic Microarray (PM) System (BIOLOG, INC., Hayward, Calif.), which allows for the simultaneous screening of approximately 1,200 phenotypes. All materials, media, and reagents for the PM system were purchased from Biolog. PM experiments were conducted using conditions recommended by the manufacturer. The PM plates were incubated at 37° C. in an Omnilog incubator and readings were recorded every 15 min for 48 h. Bacterial respiration was assessed within each well by monitoring color formation resulting from reduction of the tetrazolium violet (dye A), and color intensity was expressed in arbitrary units (AU). Kinetic data were analyzed with OmniLog-PM software from Biolog (OL_PM_Par1.20.02, Dec. 8, 2005). Carbon and nitrogen substrates showing±1.5-fold (≥15000 area under curve, arbitrary units) difference between TS-15 (green) and S. Newport (red) were considered as potential additives for future screening (yellow is the overlapping area). Carbon and nitrogen sources can then be evaluated to identify those that enable or boost the growth of TS-15, but are inhibitory or at least do not promote the growth of *Salmonella*. See FIG. 15A, FIG. 15B, FIG. 15C, FIG. 15D and FIG. 15E.

Example 9: To Determine the Effect of *P. Alvei* TS-15 Application on Tomato Quality and Quantity in Commercial Production A total of 11 inner rows (50 plants/row) in commercial farm setting will be used in this study, with 4 experimental rows and 4 control rows. Additional 3 rows will be used as border rows between control group and test group. One of the rows in experimental block will be randomly assigned to one of 4 treatments, including (1) application of *P. alvei* TS-15 in tryptic soy broth right before transplantation; (2) application of *P. alvei* TS-15 in Landy medium (salt medium) right before transplantation; (3) application of *P. alvei* TS-15 in tryptic soy broth during the early fruit stage; (4) application of *P. alvei* TS-15 in Landy medium during the early fruit stage. One of the rows in control block will be randomly assigned to one of 4 controls, including (1) application of tryptic soy broth only right before transplantation; (2) application of Landy medium only right before transplantation; (3) application of tryptic soy broth only during the early fruit stage; (4) application of Landy medium only during the early fruit stage. At commercial tomato picking stage, several randomly picked tomato plants in each row will be subjected to top-down stripping to assess the tomato quality and quantity under the treatment in general.

Application of TSB (no dilution) directly on seedlings right before transplantation was shown to be deadly to the plants. Therefore, the third treatment in the trial was changed to use TSB:H2O (1:25) as diluent to deliver *P. alvei* TS-15 during the early fruit stage.

Results

Five plants per each group (4 treatments, 4 controls and 1 border) were randomly selected and all the commercial green tomatoes on the plant were picked from top string down. A total of 2,130 commercial green tomatoes (704 lbs) were picked. Tomato size less than 6 cm in diameter was considered as small green. Counts and weights of small green tomatoes and market green tomatoes in each group were recorded. The number of market green and the number of small green tomatoes produced by the five plants in each group (i.e. 4 treatments and 4 controls) were compared with the single border row reported. This comparison used the Mann—Whitney test which is described in several statistic books including "Practical nonparametric statistics," 3$^{rd}$ edition 1999 Wiley pages 271-181 by W. J. Conover, and incorporated by reference in its entirety herein. This test orders all observations and judges whether one group is usually higher than the other. None of the treatment groups were significantly higher than the border group. The weight of market green and the weight of small green tomatoes produced by the five plants in each group were also compared with the single border row reported. None of the treatment groups were significantly higher than the border group.

Example 10: Animal Safety Study

To assess the safety of the biocontrol agents, a two phase animal safety study will be conducted. Phase 1 will assess gender specific sensitivity from oral exposure to the test organism *Paenibacillus alvei* TS-15 in adult animals, while Phase 2 will assess the effect of oral maternal exposure to the test organism *P. alvei* on fetal development.

A total of 224 animals will be utilized in Phase 1 of this study. Charles River Rats CD IGS VAF/+rats (n=112 females; n=112 males), at 8-10 weeks of age will be used in this phase. Male and female rats will be assigned to one of 4 experimental treatment groups by weight using a stratified random procedure. The test groups include: Group 1=Control Group (tryptic soy broth; TSB); Group 2=$1\times10^8$ *P. alvei* CFU/ml TSB; Group 3=$1\times10^4$ *P. alvei* CFU/ml TSB; Group 4=$1\times10^2$ *P. alvei* CFU/ml TSB. Each group will contain 28 male rats and 28 female rats. Each group will be administered the test organism by gavage at the volume and concentration stated above once, this time point will be considered exposure day 0. Animals from each of the treatment groups will be euthanized on post exposure days 7, 14, 21 or 28. During the course of the study, animal body weights, feed-cup weights, water bottle weights and temperature will be recorded daily. Animals from all experimental groups will be observed daily for signs of overt toxicity from *P. alvei* TS-15 exposure. Animals found in a morbid condition and animals showing sever pain and enduring signs of severe distress will be humanely euthanized. Animals euthanized for humane reasons are considered equivocal to animals that died on test.

A total of 120 animals will be utilized in Phase 2 of this study. Charles River Rats CD IGS VAF/+rats (n=60 females; n=30 males), at 8-10 weeks of age will be used in this phase. Male rats will be used as sires and will not be exposed to the test organism. Female rats will be assigned to one of 3 experimental treatment groups by weight using a stratified random procedure. The test groups include: Group 1=Control Group (TSB); Group 2=$1\times10^4$ *P. alvei* CFU/ml TSB; Group 3=$1\times10^2$ *P. alvei* CFU/ml TSB. Each group will contain 20 female rats. After mating, pregnant animals will be exposed to the control or test organism every $6^{th}$ day throughout the gestation period. The day a female is found to have mated (plug/sperm positive) will be considered day 0 of pregnancy. Each female will be weighed on this day and given a freshly filled feed cup and a fresh bottle of fluid. On gestation day 20 (GD-20) the pregnant animals will be euthanized and the gravid uterus will be removed in tow and weighed. The number of corpora lutea, the number of implantation sites, and the number and position of resorption sites and fetuses (dead or alive) will be reported. Each viable fetus will be examined individually and records will be kept as to its uterine position, sex, weight, externally visible abnormalities and crown rump length. Fetuses will be euthanized using dry ice and subsequently placed in Bouins Fixative for the assessment of soft tissue abnormalities or in ethanol for the assessment of skeletal abnormalities. Animals from all experimental groups will be observed daily for signs of overt toxicity from *P. alvei* TS-15 exposure. Animals found in a morbid condition and animals showing severe pain and enduring signs of severe distress will be humanely euthanized. Animals euthanized for humane reasons are considered equivocal to animals that died on test.

A particular set of experiments to assess safety is described below. The project was designed to assess the effect of: 1) oral exposure (gavage) to *P. alvei* in male, non pregnant females and pregnant animals and 2) maternal oral exposure to *P. alvei* on the developing fetus. To evaluate gender specific sensitivity, adult male and female rats received a single oral dose (gavage) of *P. alvei* and tissues were collected at post exposure days 0, 3 and 14. To evaluate the effect of the test organism on fetal development, sperm positive female rats received the test organism on gestation day 0 and every 3 days thereafter throughout gestation. As it is expected that exposure to humans would be no more than $1\times10^2$ or $1\times10^3$ CFU/ml the following dose levels were administered to study animals in both study phases: 0 CFU/ml tryptic soy broth (negative control); $1\times10^8$ CFU/ml; $1\times10^4$ CFU/ml or $1\times10^2$ CFU/ml. Neither gender specific dose-related toxic effects (feed or fluid consumption, body weight gain, and histopathology) nor developmental/reproductive effects were observed during the study. During gestation, feed consumption and maternal weight gain were not affected and dose-related changes were not observed in maternal clinical findings. At necropsy dose related changes were not observed in the number of implantations, fetal viability, or fetal size (weight and length). No gross pathology was observed in either the dams or the offspring. The test organism did not cross the placenta and was not found in the amniotic fluid. Fetuses are presently being examined for skeletal and soft tissue abnormalities and to date none have been identified. There were no histopathologic findings associated with the oral administration of *P. alvei*. Notable microscopic findings occurred at essentially comparable incidences and severity in control and treated rats and they were the usual number and type commonly observed in rats of this age.

Example 11. Genome Sequences of *Paenibacillus alvei* A6-6i and TS-15

Despite the increasing interest in *Paenibacillus* spp., genomic information for these bacteria is lacking. To date, only one whole genome sequence has been reported for *P. alvei* in GenBank (Djukic M. et al. 2012. J. Bacteriol. 194:6365; incorporated by reference). More extensive genome sequencing might lead to the discovery of a rich source of genes with biotechnological potential. Reported here is the availability of another two draft genomes of *P. alvei*. The two strains, *P. alvei* A6-6i and TS-15, were isolated from plant material and soil, respectively, in the Virginia Eastern Shore (VES) tomato growing area.

Genomic DNA was isolated from an overnight culture of each strain using a Qiagen DNeasy blood and tissue kit (Qiagen Inc., Valencia, Calif.). Genome sequencing was performed using 454 Titanium sequencing technology (Roche, Branford, Conn.), achieving >25×average genome coverage. A de novo assembly was created for each genome using the 454 Life Sciences Newbler software package v2.5.3 (Roche) and was annotated with the NCBI Prokaryotic Genomes Automatic Annotation Pipeline (www.ncbi.nlm.nih.gov/genome/annotation_prok/). Nucleotide sequence accession numbers. The draft genome sequences of strains A6-6i and TS-15 are available in DDBJ/EMBL/GenBank under GenBank accession no. ATMS00000000 and ATMT00000000, respectively, and incorporated by reference in their entirety herein.

Example 12. In Situ Evaluation of *Paenibacillus alvei* in Reducing Carriage of *Salmonella* Newport on Whole Tomato Plants The aim of this study was to isolate potential bacterial antagonists against *Salmonella*, to examine their modes of action, and to test the effectiveness in reducing carriage of *Salmonella* on whole tomato plants in a high tunnel setting.
Materials and Methods:
Isolation and Screening of Antagonistic Bacteria.
The native microflora of various plant organs (including leaves, shoots, roots, and blossoms) and soil from various Eastern Shore tomato growing locations were examined. Three grams of plant material or soil was mixed for 5 min in 1 ml of phosphate-buffered saline (PBS). An aliquot of one hundred microliters was plated onto Nutrient Yeast Glucose agar (NYGA). Ten colonies with unique morphologies that developed within 48 h at 30° C. under aerobic conditions were picked for further purification and a 3% KOH test. The KOH test is a rapid test for Gram differentiation without staining (Ryu E. et al., Kitasato Arch. Exp. Med. 17:58-63). The colony of pure cultures was then tested for antagonistic activity in vitro using an agar plug method (Visser R. et al., Appl Environ Microbiol 52:552-555). Briefly, pour plates were made containing one of the test organisms by mixing a 4 ml suspension of an overnight plate culture with sterile water in ca. 20 ml of Tryptic Soy agar (TSA). After overnight incubation at 35° C., agar plugs were punched from the agar with a sterile 10-mm stainless steel borer. The agar plugs were placed on TSA agar containing a lawn of $10^6$ cells of *Salmonella* Newport (Kuper K M. et al., Pharmacotherapy 29:1326-1343) and incubated at 35° C. The clear zones surrounding the plugs were measured at incubation period of 24, 48, and 96 h, respectively.
Bacterial Cultures.
Potential bacterial antagonist isolates were propagated on TSA at 35° C. For stock preparation, the cultures were cultivated overnight at 35° C. on TSA. The cells were resuspended in brain heart infusion broth (BHI) with 25% glycerol and stored at −80° C. Three tomato plant associated bacterial pathogens including *Erwinia carotovora* subsp. *Carotovora*, *Pseudomonas syringae* pv. tomato strain dc3000, and *Ralstonia solanacearum* race 5 were grown on TSA under 25° C. (Table 4, shown below). All the other indicator strains listed in Table 4 were grown on TSA at 35° C.

plus DNA polymerase kit (QIAGEN, Valencia, Calif.) under the following conditions: after an initial 5-min incubation at 95° C., the mixture was subjected to 30 cycles, each including 1 min at 95° C., 1 min at 58° C., and 1 min at 72° C. A final extension was performed at 72° C. for 10 min. Primers 4F, 27F, 357F, 578F, 1000R, and 1492R were used for sequencing. The BLAST algorithm was used for a homology search against Genbank. Only results from the highest-score

TABLE 4

Strains used in the study

| Strain | Reference or source |
| --- | --- |
| *Salmonella enterica* subsp. *enterica* serovar Newport #17 | CFSAN laboratory collection |
| *Salmonella enterica* subsp. *enterica* Saintpaul | CFSAN laboratory collection |
| *Salmonella enterica* subsp. *enterica* Montevideo 42N | CFSAN laboratory collection |
| *Salmonella enterica* subsp. *enterica* Javiana | CFSAN laboratory collection |
| *Salmonella enterica* subsp. *enterica* Typhimurium 368477 | CFSAN laboratory collection |
| *Salmonella enterica* subsp. *enterica* Typhimurium SAR C #1 | SGSC[a] |
| *Salmonella enterica* subsp. *enterica* Typhi SAR C #3 | SGSC |
| *Salmonella enterica* subsp. *arizonae* SAR C #5 | SGSC |
| *Salmonella enterica* subsp. *arizonae* SAR C #7 | SGSC |
| *Salmonella enterica* subsp. *arizonae* SAR C #9 | SGSC |
| *Salmonella bongori* SAR C #11 | SGSC |
| *Salmonella bongori* SAR C #13 | SGSC |
| *Salmonella bongori* SAR C #15 | SGSC |
| *Escherichia coli* O157:H7 IS O57 | CFSAN laboratory collection |
| *Escherichia coli* O157:H7 EDL933 | CFSAN laboratory collection |
| *Escherichia coli* ATCC 51434 | ATCC[b] |
| *Escherichia coli* ATCC BAA-179 | ATCC |
| *Shigella dysenteriae* 2457T | CFSAN laboratory collection |
| *Shigella dysenteriae* BS103 | CFSAN laboratory collection |
| *Cronobacter sakazakii* E932 | CFSAN laboratory collection |
| *Cronobacter sakazakii* E784 | CFSAN laboratory collection |
| *Listeria monocytogenes* NI-225 | CFSAN laboratory collection |
| *Listeria monocytogenes* R2-583 | CFSAN laboratory collection |
| Methicillin-resistant *Staphylococcus aureus* #9 | CFSAN laboratory collection |
| Methicillin-resistant *Staphylococcus aureus* #12 | CFSAN laboratory collection |
| Methicillin-resistant *Staphylococcus aureus* #28 | CFSAN laboratory collection |
| Methicillin-resistant *Staphylococcus aureus* #29 | CFSAN laboratory collection |
| Methicillin-resistant *Staphylococcus aureus* #30 | CFSAN laboratory collection |
| *Staphylococcus aureus* NRS70 | NARSA[c] |
| *Staphylococcus aureus* NRS106 | NARSA |
| *Staphylococcus aureus* NRS107 | NARSA |
| *Staphylococcus aureus* NRS271 | NARSA |
| *Salmonella enterica* Newport #17 ΔtolC::aph | CFSAN laboratory collection |
| *Erwinia carotovora* subsp. *carotovora* | Dr. Dilip Lakshman, ARS[d] |
| *Pseudomonas syringae* pv. tomato strain dc3000 | Dr. Dilip Lakshman, ARS |
| *Ralstonia solanacearum* race 5 | Dr. Dilip Lakshman, ARS |

[a]SGSC, *Salmonella* Genetic Stock Centre, University of Calgary, Canada
[b]ATCC, American Type Culture Collection, Manassas, VA, USA
[c]NARSA, Network on Antimicrobial Resistance in *Staphylococcus aureus*, Chantilly, VA, USA
[d]ARS, Agricultural Research Service, Department of Agriculture, Beltsville, MD, USA Phenotypic and Biochemical Characterizations of Potential Bacterial Antagonists.

The morphological characteristics of potential bacterial antagonists were observed by Gram staining and spore staining. These isolates were further tested with VITEK2 compact Biochemical Identification System (BioMerieux, Inc., Durham, N.C.) and Biolog Microbial Identification System (Biolog, Hayward, Calif.) with GEN III MicroPlates for biochemical properties according to manufactures' instructions.

16S rRNA Gene Amplification, and Sequencing.

Genomic DNA of potential bacterial antagonists was extracted using the WIZARD genomic DNA purification kit (Promega, Madison, Wis.). A pair of universal primers specific for bacterial 16S rRNA, Eubac27 and R1492 (DeLong E F. 1992. Proc Natl Acad Sci USA 89:5685-5689), were used to amplify the corresponding gene. PCR amplification of the 16S rRNA was performed with a Hotstart Taq queries were considered for phylotype identification, with 99% minimum similarity (Stackebrandt E. et al. Int. J. Syst. Bacteriol. 44:846-849).

Determination of Mode of Action and Spectrum of Antimicrobial Activities.

To determine mode of action and antimicrobial spectrum of the bacterial antagonists, both agar plug assay (using bacterial culture) and bioscreen assay (using culture supernatant) were performed against a broad spectrum of major foodborne pathogens and tomato plant associated bacterial pathogens (Table 4). In the agar plug assay, bactericidal effects against pathogenic bacterial strains in the zone of inhibition were confirmed when unable to be revived on TSA plates. In the bioscreen assay, the antagonist supernatant was filter sterilized with a 0.22 μm pore-size cellulose acetate (CA) membrane filter. Each 3 ml TS-15 cell-free culture supernatant (CFCS) was inoculated with 3 μl of $10^8$ cfu/mL bacterial culture (Table 4). Two hundred microliter aliquots were then dispensed into Bioscreen C (Growth Curves USA, Piscataway, N.J.) (a temperature-controlled automatic microtitre plate reader) wells and incubated as described for the respective bacterial strains. Bacterial growth was determined in five replicates by measuring O.D.$_{600}$ at 20-min intervals for 24 hrs.

Tomato Fruit Assay.

Red round ripe tomatoes (130±20 g each) were purchased from a local supermarket and refrigerated for no more than 3 days. Tomatoes were equilibrated to room temperature (RT) before testing and washed with 75% ethanol for surface sterilization and to remove waxy residue, if there was any present. After air drying in a laminar flow hood, tomatoes were aseptically placed onto sterile metal trays with the stem scars facing down. A twenty microliter drop of S. Newport overnight culture suspension (washed twice with PBS, and resuspended in 5 ml of PBS) was placed within a 3-cm-diameter circle on the side of the tomato, equidistant from both ends of the tomato. The Salmonella inoculum was allowed to dry before antagonist inoculation. A 40 µl drop of antagonist culture suspension (washed twice with PBS, and resuspended in 5 ml of fresh TSB) or 40 µl of TSB only was then placed on top of the Salmonella inoculum. After one and a half hours in the hood, completely air dried samples were placed in a humidity chamber, a closed container filled with 1.5 L of water in a 30° C. incubator. After 24 h incubation, each tomato was placed in a sterile Whirl-Pak™ filter bag containing 30 ml of PBS and hand rubbed for 5 min to dislodge surface inoculated Salmonella. The wash suspension was diluted 10-fold in PBS and 0.1 ml aliquots of the appropriate dilutions were spread onto XLD agar (Becton Dickinson and Company, Sparks, Md.) to determine the surviving Salmonella populations.

Field Trials in High Tunnel. (i) Plants.

Trials were performed in 2010 (July through September) on tomato cultivar BHN602 in an insect-screened high tunnel at the United States Department of Agriculture (USDA), Beltsville Agricultural Research Center (BARC) north farm, Beltsville, Md. Tomato plants were started from seeds in a BARC greenhouse. Seedlings were grown in commercial organic peat mix and fertilized with Neptune's Harvest Organic Fish/Seaweed Blend fertilizer before and after transplanting. In the high tunnel, fertilizer was supplied from a single injector through drip tape supplemented with an OMRI-approved calcium source to prevent blossom end rot. Black plastic mulch was used to cover the 8 planting beds (2'×20' each) over the drip tape. Planting slits were made in the black plastic at 15" intervals to accommodate 13 transplants per bed. Plants were staked and fitted with nylon support strings when 10" high. Plants were irrigated immediately after transplanting and at least weekly to achieve 1-1.5" water and meet fertility requirements. Soil moisture was monitored by irrometers and digitally on the Hobo weather station that is located in the center of the high tunnel. Temperature, RH (Relative Humidity), PAR (Photosynthetically Active Radiation), and total SR (Solar Radiation) were monitored and recorded as well at the same time.

(ii) Experimental Design.

A split-plot design was used with two treatments (Salmonella only and Salmonella with antagonist) as the first level sub-plot. Inoculation sites including leaf, blossom and tomato fruit were each assigned a second level sub-plot, with each inoculation site as an independent experimental unit; and day of harvest post-inoculation as a repeated measure. The second level corresponds to harvests used for 0 day (2 hrs after inoculation as a benchmark for % recovery), 1 day, 2 days, 3 days, and 5 or 6 days persistence trials. Thirteen plants were planted in each plot. One plant on each end of each bed served as an uninoculated border plant, leaving 11 replicates per plot.

(iii) Inoculum Preparation.

Because of concerns about the safe use of pathogens in the field, an attenuated S. Newport strain #17 ΔtolC::aph was constructed for the high tunnel study. The tolC gene on the S. Newport strain #17 chromosome was replaced by a cassette containing a kanamycin resistance gene using the one-step inactivation method described by Datsenko and Wanner (Datsenko K A et al. 2000. Proc Natl Acad Sci USA 97:6640-6645). TolC is an outer membrane protein not only important for the efflux of small compounds, but also for the export of large proteins. Disruption of tolC abolished the ability of S. Typhimurium to adhere, invade and survive in eukaryotic cells (Buckley A M et al. 2006. Cell Microbiol 8:847-856). S. Enteritidis tolC mutant was shown to be avirulent in the BALB/c mouse model as well (Stone B J et al. 1995. Mol Microbiol 17:701-712). TSB suspensions of S. Newport strain #17 ΔtolC::aph overnight culture were washed twice in PBS and then spot inoculated to three marked leaves (20 µl each), six to nine blossoms (10 µl each), and three breaker to red tomatoes (20 µl each) for a final concentration of ~$10^9$ CFU/ml per plant. The inoculation spots were allowed to air dry (~1 h) before applying the antagonist. Antagonist cell suspensions were made from a bacterial lawn. After twice washing with PBS, cells were resuspended in 10 ml of TSB. Forty microliters of antagonist cell suspension or sterile TSB were applied to the same inoculation spot on leaves and tomatoes, and 10 ul to Salmonella-inoculated blossoms, of each plant in the 'with' or 'without' antagonist group, respectively. Leaves, blossoms, and tomatoes were harvested at day 0, day 1, day 2, day 3, and day 5 (for blossoms) or day 6 (for leaves and tomatoes) post inoculation.

(iv) Sample Collection.

Inoculated leaves, blossoms, and tomatoes from each plant were removed with sterile scissors and placed in individual plastic zipper bags, which were sealed and transported in a cooler to the laboratory for analysis within 1 h. For leaves and blossoms, each sample bag was filled with 15 ml and 10 ml of PBS, respectively, and hand-rubbed for 3 min to dislodge surface populations of Salmonella. For tomatoes, each sample bag was filled with 30 ml of PBS and subjected to sonication at 55 Hz/min for 30 sec. The PBS was diluted or concentrated through filtration (at later time points of the experiment) and surface plated (0.1 ml in duplicate) on TSA-kan (50 µg/ml). Plates were incubated at 35° C. overnight and counted for kanamycin resistant colonies. Two colonies were randomly picked from each TSA-kan plate and confirmed by PCR using a set of verification primers.

(v) Statistical Analysis.

Estimates of the rate of reduction in bacterial counts were obtained by fitting a robust linear model of the log transformed CFU onto days (days after inoculation). The slopes of the fitted lines from antagonist treated and untreated surfaces were compared to look for differences in the rates of reduction. The analysis was performed using the R statistical software package, version 2.11.1, with the robust library. The results were tallied for each combination of plant location, antagonist, plant, and day. Within each plant location, both a regression and a rank test compared the effect of using the antagonist with that of not using it. The tally of the plates divided the sum of their counts by the sum of the masses of the original sample that they received. An imputation procedure, discussed by Blodgett et al. (2008. Food Microbiol 25:92-98), accounted for the TNTC plates.
Results:
Isolation and Identification of Antagonistic Bacteria.

A large number of environmental isolates from the tomato field were screened for antimicrobial activity against S. Newport. Two isolates, one from an epiphytic leaf surface of native Eastern Shore vegetation and the other from Eastern Shore tomato soil, showed distinct inhibition areas on basal TSA agar. These isolates formed pale colonies and swarmed vigorously on TSA. Morphologically, the isolates were rod-shaped, 0.7-0.95 cm by 3.18-3.42 cm, gram-positive bacteria. Upon prolonged incubation on an agar medium, cells produced central endospores.

The isolates were positive for oxidase, nitrate reduction, gelatin liquefaction, starch hydrolyzation, casein hydrolysis, glucose fermentation, and urease but negative for catalase, indole production, and $H_2S$ formation. The bacterium grew well in TSB broth under aerobic conditions. Genomic analysis showed the 16S rRNA gene of both isolates shares over 99.0% sequence similarity with that of *Paenibacillus alvei*. Biolog Gen III MicroPlate confirmed the high similarity of both isolates (>99%) with *P. alvei*. Thus, it was concluded that both isolates belong to *P. alvei*, and they were given strain designations of A6-6i and TS-15 respectively.

Broad Antimicrobial Spectrum of *P. alvei* Strains A6-6i and TS-15.

Figure 22:
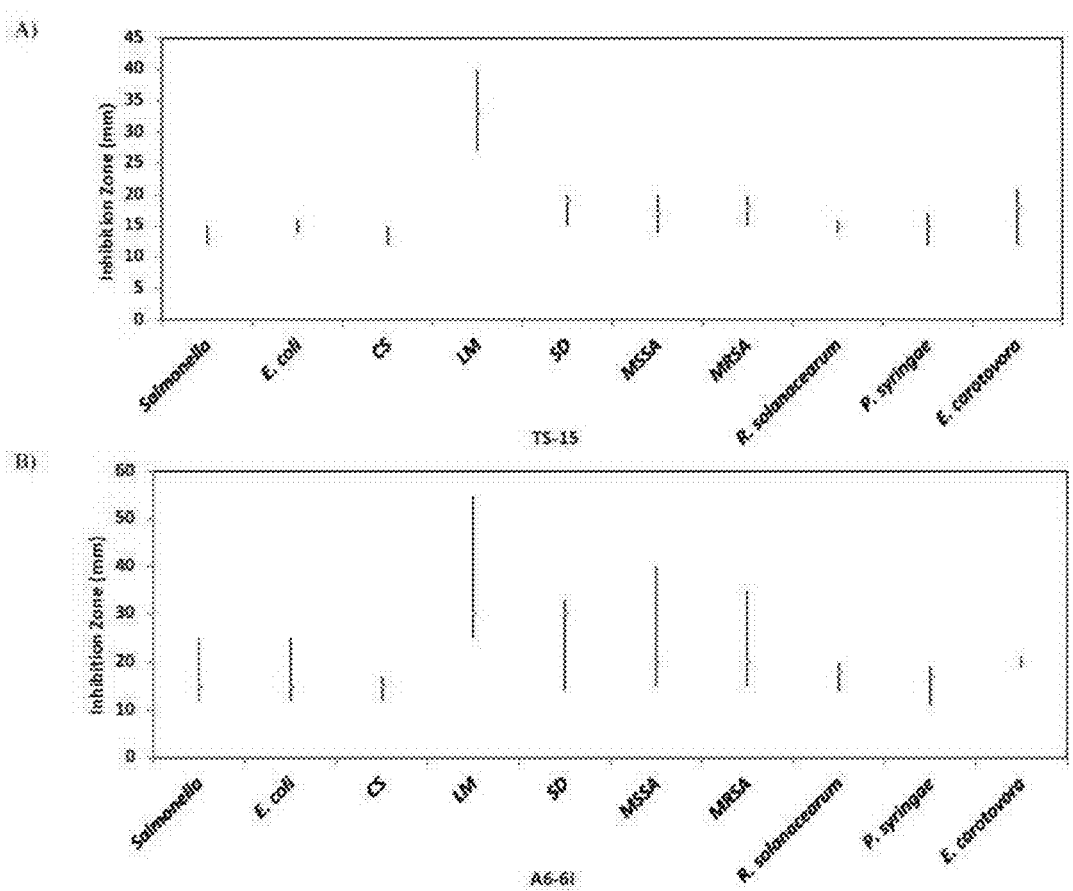
FIG. 22 (A and B) are graphs of the results of in vitro agar plug assays showed inhibition zones against all the indicator strains including six major foodborne pathogens and three major tomato plant associated bacterial pathogens when challenged with both P. alvei isolates.

In vitro agar plug assays showed inhibition zones against all the indicator strains including six major foodborne pathogens and three major tomato plant associated bacterial pathogens when challenged with both *P. alvei* isolates (FIGS. 22A and 22B). Notably, the antagonist migrated outward from the plug after forming the inhibition zone on SD (*S. dysenteriae*) or LM (*L. monocytogenes*), and the antagonistic growth ring expanded with time, especially in the case of *Listeria*. Both A6-6i and TS-15 had a wide range of inhibition against MRSA strains with zone diameters from 15 to 35 mm, and 15 to 20 mm, respectively. It is also interesting to note that strain A6-6i showed strong inhibitory effects on various MRSA strains tested despite the fact that some strains were resistant to up to 14 different antimicrobial drugs.

Figure 23:
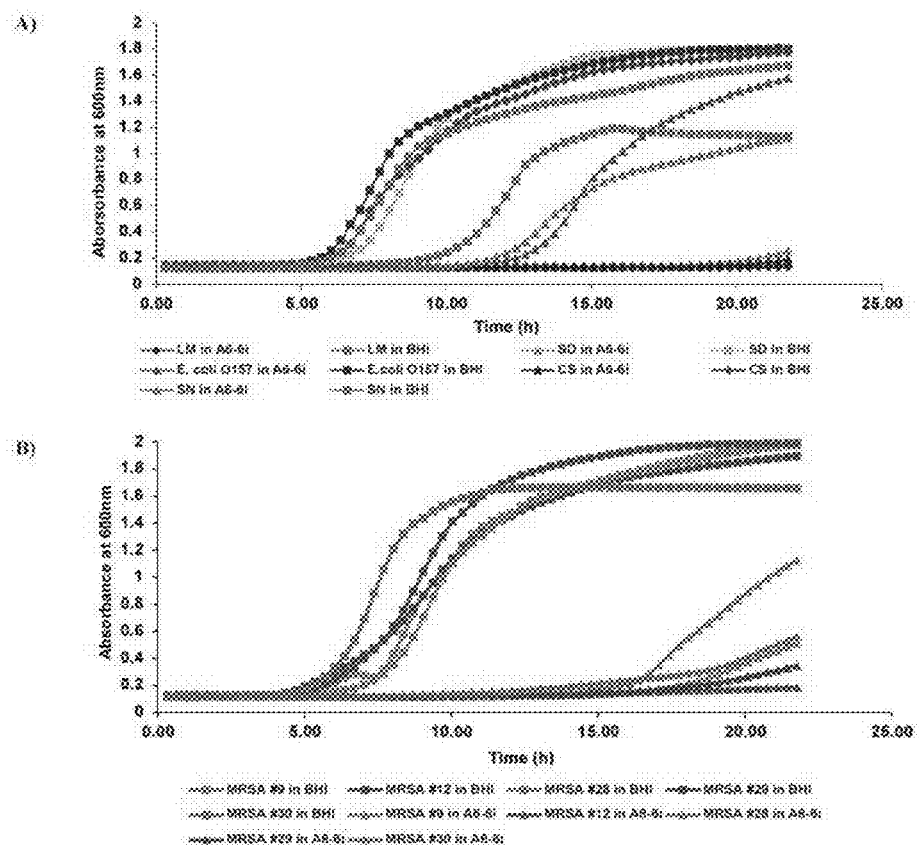
FIG. 23 (A and B) are graphs that show the results of experiments where supernatants were tested against the panel of gram-negative and gram-positive bacteria using the Bioscreen assay.

When supernatants were tested against the panel of gram-negative and gram-positive bacteria using the Bioscreen assay, both A6-6i (FIG. 23) and TS-15 (not shown) CFCS exhibited a broad spectrum of antimicrobial activity, in which the lag phase was significantly extended in all the pathogens tested and the cell density was largely reduced at the end of incubation. Furthermore, the lag phase in CS (*C. sakazakii*), SD (*S. dysenteriae*), LM (*L. monocytogenes*), and some MRSA strains were extended to almost 24 h in both A6-6i and TS-15 CFCS. Comparing to A6-6i, CFCS from TS-15 had much stronger inhibitory effect when tested against SN (*S. Newport*) (not shown).

Efficacy of *P. alvei* A6-6i and TS-15 on Tomato Fruit in Humidity Chambers.

Figure 24:
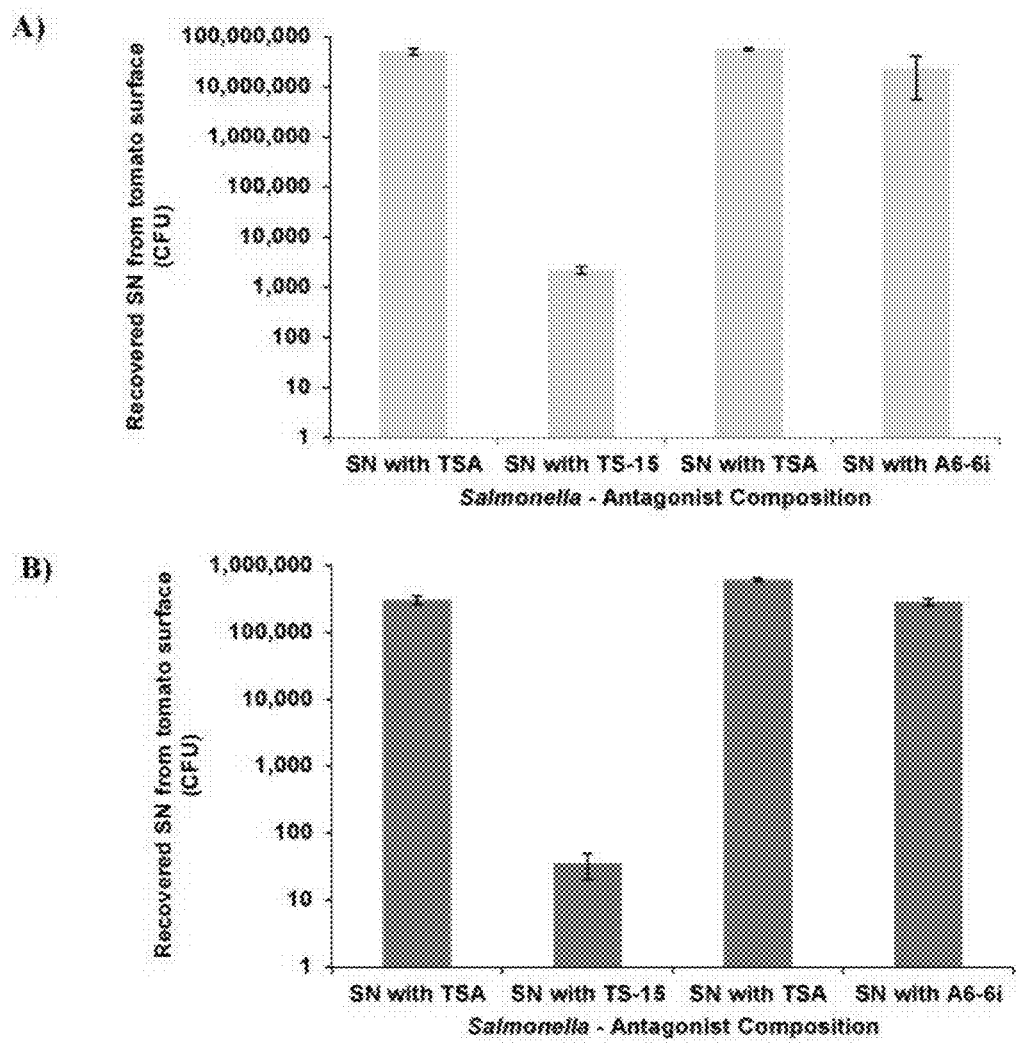
FIG. 24. (A and B) are graphs that show the efficacy of P. alvei A6-6i and TS-15 on tomato fruit in humidity chambers. No significant difference was found in the reduction rate regardless of whether or not the antagonist was inoculated before (FIG. 3A) or after S. Newport inoculation (FIG. 3B)

S. Newport showed significant reduction on the tomato fruit surface by both *P. alvei* strains A6-6i and TS-15. However, comparing an average of ½ log reduction by A6-6i, TS-15 had a 5 log reduction in the S. Newport population applied to tomato fruits (FIG. 24). Numbers of *S. Newport* recovered from tomato surfaces were 100 times less on average when the antagonist was added prior to *Salmonella* on the tomato surface. Nevertheless, no significant difference was found in the reduction rate regardless of whether or not the antagonist was inoculated before (FIG. 3A) or after S. Newport inoculation (FIG. 24B).

Field Trials in High Tunnel Using *P. alvei* TS-15.

Figure 25:
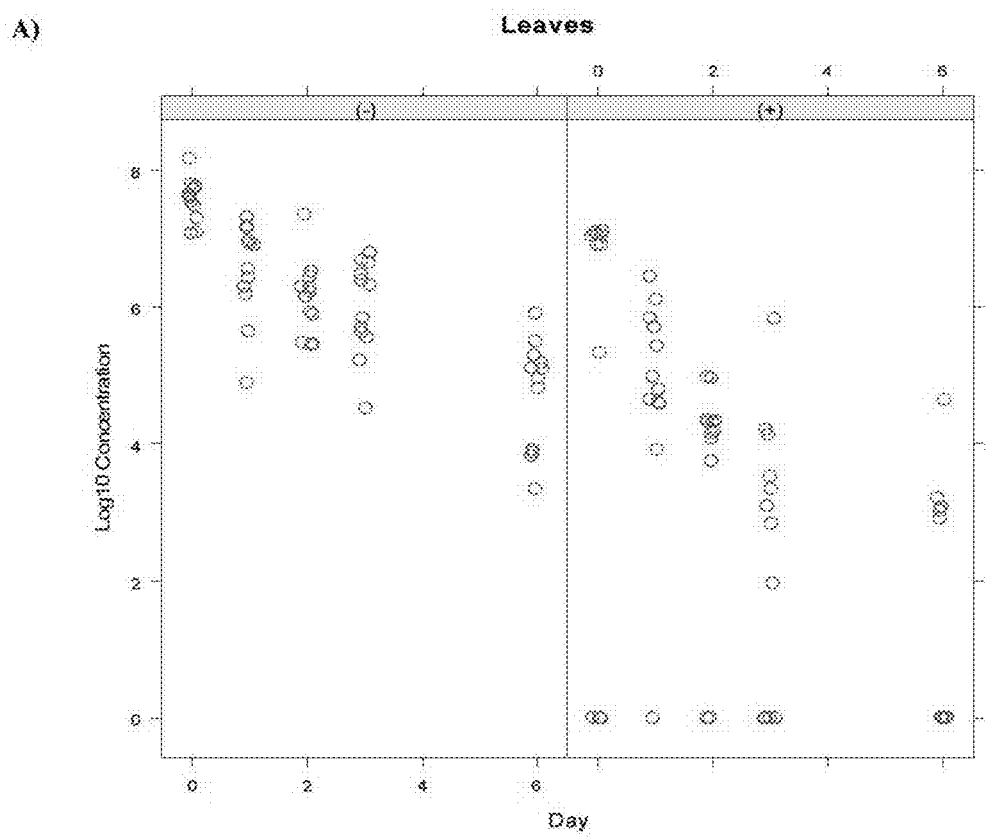
FIG. 25 shows the results of high tunnel field trials.
Figure 26:
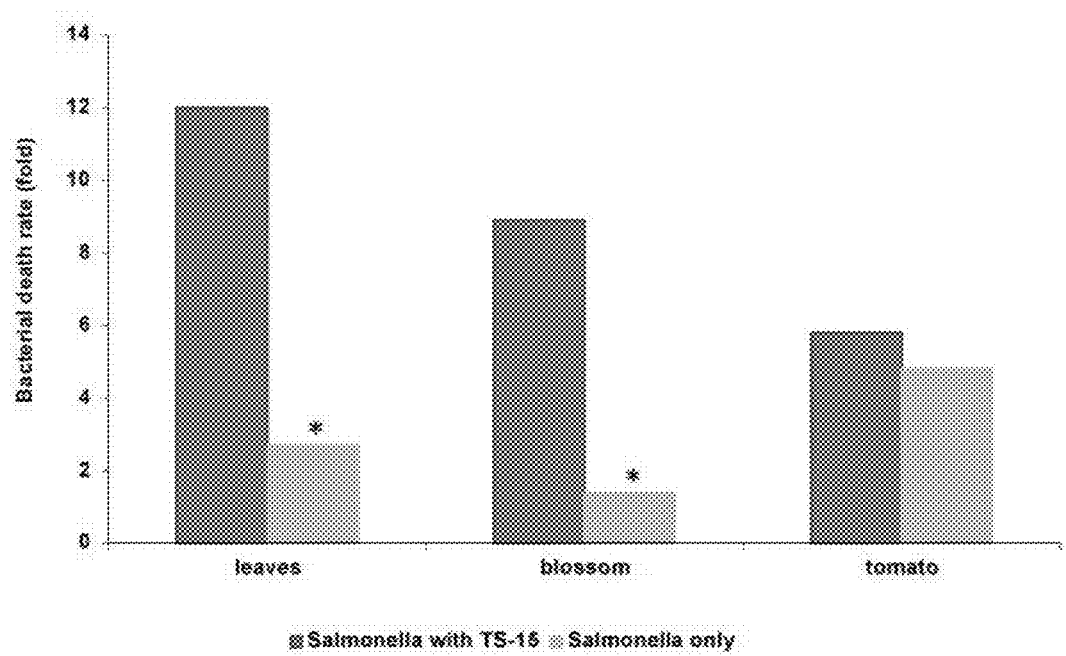
FIG. 26 is a graph that shows the rate of decrease in bacterial concentration.

Based on the results from tomato fruit assay, *P. alvei* strain TS-15 was selected for further high tunnel field trials. During field trials from July through September 2010, the maximum daily temperature and RH varied, respectively, between 26.7 and 37.8° C. and between 56% and 80% (available at www.wunderground.com/history/). At Day 0, variations were detected between the group without TS-15 and the group with TS-15 on leaf and blossom but not on tomato in terms of *Salmonella* population after inoculation (FIG. 25). Taking all the variations into effect, the concentration of *Salmonella* was significantly lower (p<0.05) on plants with TS-15 on leaves, blossoms, and tomatoes from day 1 to day 5 (for blossom) or day 6 (for leaf and tomato) (FIG. 25). Notably, close to 100% of the 'Salmonella only' plants still had detectable levels of *Salmonella* at the end of the blossom and leaf trials, whereas only 2 plants (<20%) had detectable levels of *Salmonella* in the 'antagonist group' in the blossom trial and 6 plants (~50%) in the leaf trial. Moreover, the rate of decrease in bacterial concentration was significantly higher (p≤0.05) on leaves and blossoms with TS-15 versus those without TS-15; Decreases were 12 fold per day versus 2.7 fold per day for leaves, and 8.9 fold versus 1.4 fold for blossoms, respectively (FIG. 26). Nevertheless, no statistically significant difference was found in the mortality rate of *Salmonella* on tomato fruits.

Discussion

Contaminated tomatoes have been implicated in several high profile outbreaks within North America (MMWR Morb Mortal Wkly Rep 56:909-911; MMWR Morb Mortal Wkly Rep 57:929-934). *Salmonella enterica* serovar Newport is amongst the recurring serovars implicated in foodborne outbreaks associated with tomatoes (Aronson S M. 2008. Med Health R I 91:267; Orozco L. et al., Journal of food protection 71:60-65). Extensive research has been done to show that *Salmonella* can contaminate the fruit at the primary production level through soil, irrigation water and blossoms (Zheng J. et al. 2013. Appl Environ Microb 79:2494-2502; Greene S K et al. 2008. Epidemiol Infect 136:157-165; Shi X. et al. 2007. Journal of food protection 70:2725-2731; Jablasone J. et al., 2004. J Sci Food Agr 84:287-289), allowing the pathogen to colonize the exterior and interior of developing fruit. Due to the risk of internalization, *Salmonella* needs to be controlled at the farm level. Biological control has been widely applied to suppress plant diseases caused by phytopathogens. However, few have been reported to control foodborne pathogens on produce especially at the preharvest level. With only 1- to 2-log reductions, limited success was achieved using bacteriophages as biocontrol agents (Kocharunchitt C. et al. 2009. Int J Food Microbiol 128:453-459; Ye J. et al. 2009. Journal of food protection 72:2284-2292). *Enterobacter asburiae* strain JX1demonstrated over a 5-log reduction in the growth of *Salmonella* in the rhizosphere of tomato plants and on the developing fruit (Ye J. et al. 2009), however, this bacterium can cause an array of diseases in humans (Brenner D J. Et al., 1986. J Clin Microbiol 23:1114-1120). Introduction of *E. asburiae* into produce might exacerbate the problem of foodborne pathogen growth on produce. In this study, two new bacterial strains, A6-6i and TS-15, exhibiting great antimicrobial efficacy against a broad range of foodborne pathogens and tomato plant associated bacterial pathogens, were identified as *P. alvei*, which is very rarely associated with human infections. Results of the in situ tomato plant trials further showed that *P. alvei* strain TS-15 is highly effective in reducing the carriage of S. Newport on tomato plants, indicating its potential use as a novel biocontrol agent to mitigate *Salmonella* contamination at the preharvest level.

The antagonist may exhibit competitive exclusion over certain foodborne pathogens; many *Paenibacillus* species are already part of the natural microbial community in soil, water, and rhizosphere of various plants (Gardener B B M. 2004. Phytopathology 94:1252-1258). Results from the bioscreen assay and agar plug assay, however, indicate that the inhibitory effect of this antagonist on foodborne pathogens can be mainly attributed to its antimicrobial activities. Whole genome sequencing was performed to help identification of diverse antibiotic biosynthetic genes present in these two isolates. A few novel antimicrobial agents, with activities against many foodborne pathogens including *Salmonella* spp., *E. coli* O157:H7, *L. monocytogenes, S. dysenteriae, C. sakazakii*, and multi-drug resistant *S. aureus*, were discovered in our laboratory (unpublished data).

In the high tunnel trial, *P. alvei* TS-15 was much more effective in suppressing the growth of *Salmonella* on blossoms and on leaves than on tomatoes. Provided that *Salmonella* mortality rate in control group was much higher on tomato fruits compared to those on leaves and blossoms, smooth, waxy surfaces of developing tomato fruits seemed to be harder for microbes to survive in general. This may also affect the application strategy for this biocontrol agent. However, the effectiveness of biological intervention has been shown to be greatly affected by the ratio of antagonist to pathogen in culture (Liao C H. 2009. Journal of food protection 72:85-92). Provided that the ratio of *P. alvei* TS-15 to S. Newport was only 1:1 in the fruit assay and high tunnel trial and the actual level of *Salmonella* on naturally contaminated produce is much lower than 6 log CFU/g of tissue, application of *P. alvei* TS-15 at 6 log CFU/g of tissue as used in this study should be sufficient to inhibit the growth of *Salmonella* on tomato to a clinically significant level.

In summary, the results of this study have demonstrated the efficacy of *P. alvei* TS-15 against *Salmonella* on the blossoms and leaves of tomato plants. In order to more successfully apply such an agent, studies will be conducted to determine the efficacy of *P. alvei* TS-15 in suppressing *Salmonella* in the rhizosphere of tomato plants, to develop formulation *P. alvei* TS-15 for use against *Salmonella* and other foodborne pathogens on produce crops, and to assess the safety due to environmental and human exposure to this organism.

REFERENCES

The following references are incorporated herein by reference and may be cited to as further background support of this specification.

(1) Visser R. Appl. Environ. Microbiol. 1986 552-555.
(2) Wanger, A. Antibiotic Susceptibility Testing. 2009 149-159. in Goldman E., and Green L. H. Practical handbook of Microbiology, $2^{nd}$ edition.
(3) DeLong, E. F. Proc. Natl. Acad. Sci. USA, 1992 (89): 5685-5689.
(4) Gonzalez-Escalona et al. 2005 Polymorphism and gene conversion of the 16S rRNA genes in the multiple rRNA operons of *Vibrio parahaemolyticus*. FEMS Microbiology Letters 246: 213-219.
(5) Turner, S., Pryer, K. M., Miao, V. P. W., and Palmer, J. D. 1999. Investigating deep phylogenetic relationships among cyanobacteria and plastids by small subunit rRNA sequence analysis. Journal of Eukaryotic Microbiology 46: 327-338.
(6) Blodgett, R. J., 2008 Mathematical treatment of plates with colony counts outside the acceptable range. Food Microbiology 25: 92-98.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All patents and publications mentioned in this specification are herein incorporated by reference to the same extent as if each independent patent and publication was specifically and individually indicated to be incorporated by reference.

What is claimed is:

1. A composition, comprising:

an effective amount of freeze-dried *Paenibacillus alvei* strain TS-15 deposited under ATCC Accession No. PTA-121756, at least one carbon-source booster selected from the group consisting of glucose and melezitose, and yeast extract as a nitrogen-source booster, wherein the *Paenibacillus alvei* strain TS-15 deposited under ATCC Accession No. PTA-121756 is capable of inhibiting or eliminating the growth of a bacterial human foodborne pathogen and a bacterial plant pathogen on a plant or plant organ.

2. The composition of claim 1, wherein the human foodborne pathogen is a species of *Salmonella, Escherichia, Listeria, Shigella, Enterobacter* and *Staphylococcus.*

3. The composition of claim 1, wherein the human foodborne pathogen is *Salmonella enterica* serovar Newport.

4. The composition claim 1, wherein the human foodborne pathogen is *E. coli* O157:H7.

5. The composition of claim 1, wherein the plant pathogen is *Clavibacter michiganensis* pv. *michiganensis, Pseudomonas syringae* pv. tomato, *Xanthomonas capesiris* pv. *vesicatoria, Ralstonia solanacearum*, or *Erwinia carotovora* subsp. *carotovora.*

6. The composition of claim 1, wherein the plant or plant organ is from the family Solanaceae.

7. The composition of claim 1, wherein the plant or plant organ is a tomato plant or organ thereof.

8. The composition of claim 1, wherein the plant or plant organ is a pepper plant or organ thereof.

9. The composition of claim 1, wherein the plant or plant organ is a fruit or vegetable produced by the plant.

10. A kit for treating a plant or plant organ in vitro or in situ, said plant or plant organ being contaminated with a bacterial human foodborne pathogen or a bacterial plant pathogen, wherein the kit comprises the composition of claim 1.

11. The composition of claim 1, wherein the carbon-source booster and/or the nitrogen-source booster accelerate growth and/or bactericidal activity of the *Paenibacillus alvei* strain TS 15.

12. The composition of claim 1, wherein the carbon-source booster and/or nitrogen-source booster does not boost the growth of the bacterial human foodborne pathogen or the bacterial plant pathogen.

13. The composition of claim 1, wherein the carbon-source booster and/or nitrogen-source booster inhibits the growth or proliferation of the bacterial human foodborne pathogen or the bacterial plant pathogen.

14. The composition of claim 1, further comprising culture supernatant from *Paenibacillus alvei* strain TS-15.

15. A method of inhibiting or eliminating the growth of a bacterial plant or human pathogen on the surface of a plant or plant organ comprising contacting the plant or plant organ with the composition of claim 1.

\* \* \* \* \*